United States Patent
Zhou et al.

(10) Patent No.: US 10,711,006 B2
(45) Date of Patent: Jul. 14, 2020

(54) SELECTIVE BRUTON'S TYROSINE KINASE INHIBITOR AND USE THEREOF

(71) Applicant: HANGZHOU HERTZ PHARMACEUTICAL CO., LTD., Hangzhou, Zhejiang Province (CN)

(72) Inventors: Xinglu Zhou, Hangzhou (CN); Xingguo Liu, Hangzhou (CN); Miao Hu, Hangzhou (CN)

(73) Assignee: HANGZHOU HERTZ PHARMACEUTICAL CO., LTD., Hangzhou (CN)

( * ) Notice: Subject to any disclaimer, the term of this patent is extended or adjusted under 35 U.S.C. 154(b) by 0 days.

(21) Appl. No.: 16/346,448

(22) PCT Filed: Oct. 24, 2017

(86) PCT No.: PCT/CN2017/107416
§ 371 (c)(1),
(2) Date: Apr. 30, 2019

(87) PCT Pub. No.: WO2018/090792
PCT Pub. Date: May 24, 2018

(65) Prior Publication Data
US 2019/0276461 A1  Sep. 12, 2019

(30) Foreign Application Priority Data

Nov. 15, 2016  (CN) .................. 2016 1 1014370
Sep. 5, 2017  (CN) .................. 2017 1 0789936

(51) Int. Cl.
A61K 31/519  (2006.01)
C07D 487/04  (2006.01)
(Continued)

(52) U.S. Cl.
CPC .......... *C07D 487/04* (2013.01); *A61K 31/519* (2013.01); *A61K 45/06* (2013.01);
(Continued)

(58) Field of Classification Search
CPC ........................ A61K 31/519; C07D 487/04
(Continued)

(56) References Cited

FOREIGN PATENT DOCUMENTS

| | | |
|---|---|---|
| CN | 105777759 A | 7/2016 |
| CN | 106146518 A | 11/2016 |

(Continued)

*Primary Examiner* — Jeffrey H Murray
(74) *Attorney, Agent, or Firm* — Jiwen Chen

(57) ABSTRACT

The present invention relates to a selective Bruton's tyrosine kinase (BTK) inhibitor compound, a pharmaceutical composition, preparation and use thereof in preparation of a drug. The compound of the present invention has a structure of Formula II or Formula II':

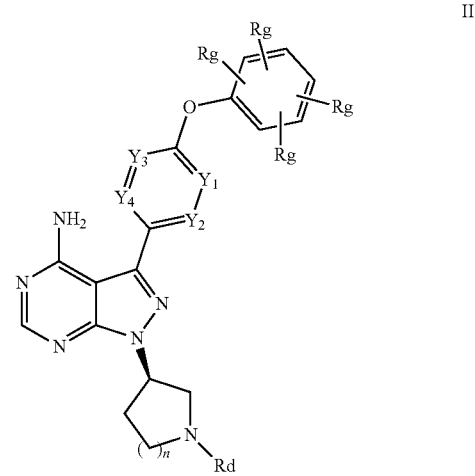

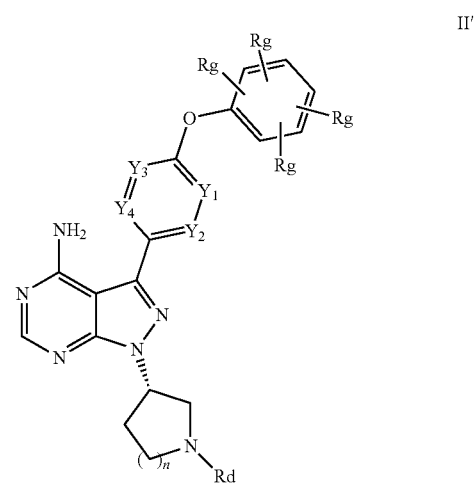

or their optical isomers, or pharmaceutically acceptable salts or solvates;

where each Rg is independently H, halogen, —CF$_2$H, —CF$_3$, —CN, C1-C3 alkyl, or C1-C3 alkoxy;

n is selected from 0, 1 and 2;

Rd is selected from

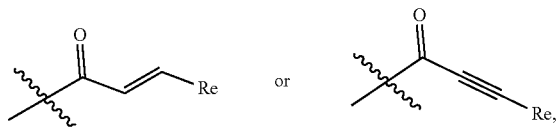

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl are further substituted with amino, hydroxyl, and C1-C3 alkyl;

(Continued)

$Y_1$, $Y_2$, $Y_3$ and $Y_4$ are independently selected from C(Rf) and N, and at least one of $Y_1$, $Y_2$, $Y_3$ and $Y_4$ is N, wherein Rf is selected from H, halogen, C1-C3 alkyl, —$CF_3$, and —$CF_2H$.

19 Claims, No Drawings

(51) Int. Cl.
    *A61P 37/06*     (2006.01)
    *A61P 19/02*     (2006.01)
    *A61P 35/00*     (2006.01)
    *A61P 21/04*     (2006.01)
    *A61K 45/06*     (2006.01)
    *A61P 1/00*     (2006.01)
    *A61P 17/00*     (2006.01)
    *A61P 35/02*     (2006.01)
    *A61P 37/02*     (2006.01)
    *A61P 3/10*     (2006.01)

(52) U.S. Cl.
CPC .................. *A61P 1/00* (2018.01); *A61P 3/10* (2018.01); *A61P 17/00* (2018.01); *A61P 19/02* (2018.01); *A61P 21/04* (2018.01); *A61P 35/00* (2018.01); *A61P 35/02* (2018.01); *A61P 37/02* (2018.01); *A61P 37/06* (2018.01)

(58) Field of Classification Search
USPC ........................................ 514/262.1; 544/262
See application file for complete search history.

(56) References Cited

FOREIGN PATENT DOCUMENTS

| WO | WO2014188173 A1 | 11/2014 |
| WO | WO2016145935 A1 | 9/2016 |

SELECTIVE BRUTON'S TYROSINE KINASE INHIBITOR AND USE THEREOF

This is a U.S. national stage application of PCT Application No. PCT/CN2017/107416 under 35 U.S.C. 371, filed Oct. 24, 2017 in Chinese, claiming priority of Chinese Application No. 201611014370.6 filed Nov. 15, 2016 and 201710789936.0 filed Sep. 5, 2017, all of which are hereby incorporated by reference.

TECHNICAL FIELD

The present invention belongs to the field of medicine, and in particular relates to a dual-site irreversible Bruton's tyrosine kinase inhibitory compound, and compositions, preparation and application thereof.

BACKGROUND

Small-molecule covalent inhibitors, also known as irreversible inhibitors, are a class of inhibitors that exert their biological functions by irreversible binding of covalent bonds to target protein residues. Covalent inhibitor drugs have made important contributions to human health over the past few decades. Relative to non-covalent inhibitors, covalent inhibitors enhance affinity to targets by covalent bonding to target proteins, which is the underlying cause of the high bioactivity of the covalent inhibitors. In recent years, due to generation of resistance to non-covalent targeting anti-tumor drugs, especially to a large number of kinase-targeted tinib drugs, people have paid more attention to covalent inhibitor drugs again. In recent years, many large pharmaceutical companies have developed covalent inhibitors for specific enzyme targets. Currently, some covalent inhibitors, including afatinib, canertinib, and neratinib, have entered clinical trials. Among them, Afatinib was officially approved by the US FDA on Jul. 12, 2013 for the treatment of metastatic non-small cell lung cancer with epidermal growth factor receptor (EGFR) gene mutation, becoming the first FDA-approved new irreversible inhibitor drug for treatment of lung cancer. In addition, antiviral covalent drugs have also been a research hotspot in recent years, and great progress has been made. For example, in 2011, FDA approved two anti-hepatitis C virus covalent inhibitory drugs, namely, Telaprevir and Boceprevir. These studies demonstrate that irreversible inhibitors are effective for the treatment of diseases.

Bruton's tyrosine kinase (Btk), a member of the Tec family of non-receptor tyrosine kinases, is a key signal kinase expressed in all hematopoietic cell types except T lymphocytes and natural killer cells. Btk plays a crucial role in the signaling pathways of B cells that link cell surface B-cell receptor (BCR) and stimulate the downstream cell responses. Btk is a key regulator, affecting B cell development, activation, signaling, and survival. In addition, Bkt plays a role in signaling pathways of numerous other hematopoietic cells, such as Toll like receptor (TLR)- and cytokine receptor-mediated TNF-α production in macrophages, Immunoglobulin E receptor (FcεR1) signaling in mast cells, signaling for inhibition of Fas/APO-1 apoptosis in B-lineage lymphoid cells, and collagen-stimulated platelet aggregation. For example, see in C. A. Jeffries et al, J. Bio. Chem. (2003) 278: 26258-26264, N. J. Horwood et al, J. Exp. Med. (2003) 197: 1603-1611. Recent studies have shown that the Btk signaling pathway is a new hotspot in the current clinical treatment researches of non-Hodgkin's lymphoma (NHL), especially chronic lymphocytic leukemia (CLL), B-cell lymphoma and autoimmune diseases. Small-molecule Btk inhibitors inhibit Btkautophosphorylation by binding to Btk by acting on the BCR signaling pathway, thereby preventing Btk activation and further blocking cell conduction and inducing apoptosis. The release of the Btk inhibitor, ibrutinib, has been considered as a "breakthrough" new drug by FDA, and its research and development prospects are broad. However, in recent year's treatment, it has gradually found that ibrutinib has bleeding-related side effects, and literature studies suggest that it may be related to the poor selectivity of ibutinib, especially the related activities of TEC kinases. In addition, in the FDA application documents of ibrutinib, some review experts stated that the $IC_{50}$ of its hERG channel blocking activity is low ($IC_{50}$=1 μM), and there is a risk of cardiac toxic and side effects. Therefore, there is an urgent need to develop a more efficient class of selective BTK inhibitors for the treatment of related diseases.

A class of BTK irreversible inhibitors and their optical isomers or pharmaceutically acceptable salts or solvates, are reported in the applicant's prior patent documents (Chinese Patent Application Nos.: 201510242552.8 and 201610286399.3), with I and II in the following formula as represent compounds. Through further research, we found a class of compounds with high kinase selectivity, low hERG inhibitory activity and BTK inhibitors with good pharmacokinetic properties, which are expected to further reduce the risk of bleeding, rash, cardiac toxic side effects and so on.

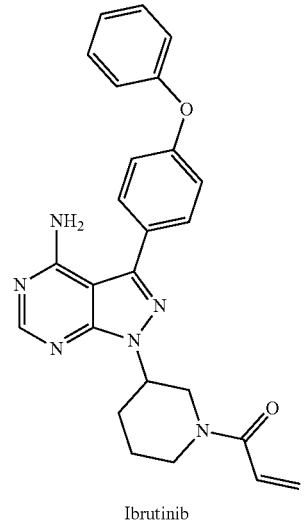

Ibrutinib

-continued

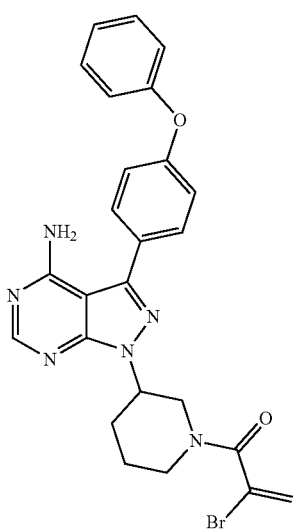

I

SUMMARY OF THE INVENTION

The object of the present invention is to provide a novel and unreported BTK inhibitory compound having efficient BTK inhibitory activity, high specificity (good kinase selectivity) and low HERG channel blocking activity, and their optical isomers thereof or pharmaceutically acceptable salts or solvates thereof.

The present invention further provides a pharmaceutical composition comprising the compound and their optical isomers, or the pharmaceutically acceptable salts or solvates.

The present invention further provides a pharmaceutical preparation comprising the compound and their optical isomers, or the pharmaceutically acceptable salts or solvates.

The present invention also provides use of the compound, and their optical isomers, or the pharmaceutically acceptable salts or solvates in the preparation of a drug for treating diseases, disorders or conditions benefiting from the inhibition of the Bruton's tyrosine kinase activity.

The present invention adopts the following technical solutions:

A Bruton's tyrosine kinase inhibitor provided by the present invention has a structure of Formula I or Formula I':

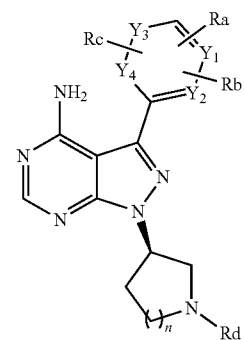

I

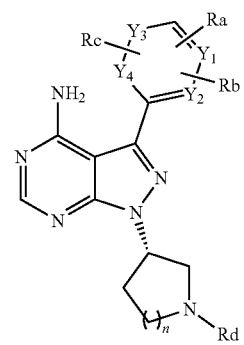

I' or their optical isomers, or pharmaceutically acceptable salts or solvates;

where Ra, Rb and Rc are independently selected from H, halogen, —CF$_2$H, —CF$_3$, —CN, C1-C3 alkyl, -L-substituted/unsubstituted C5-C12 heteroaryl, or -L-substituted/unsubstituted C5-C12 aryl, where L is a bond, O, S, —S(=O), —S(=O)$_2$, NH, C(O), CH$_2$, —NHC(O)O, —NHC(O) or —C(O)NH;

n is selected from 0, 1 and 2;

Rd is selected from

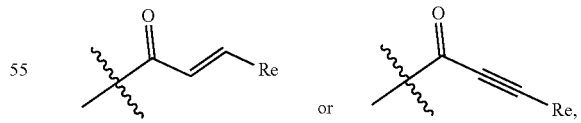

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl may be further substituted with amino, hydroxyl, or C1-C3 alkyl;

Y$_1$, Y$_2$, Y$_3$ and Y$_4$ are independently selected from C(Rf) and N, and at least one of Y$_1$, Y$_2$, Y$_3$ and Y$_4$ is N, wherein Rf is selected from H, halogen, C1-C3 alkyl, —CF$_3$, and —CF$_2$H.

Still further, the preferred compound of the present invention has a structure of Formula II or Formula II':

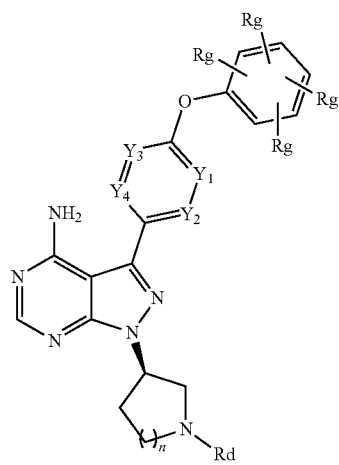

II

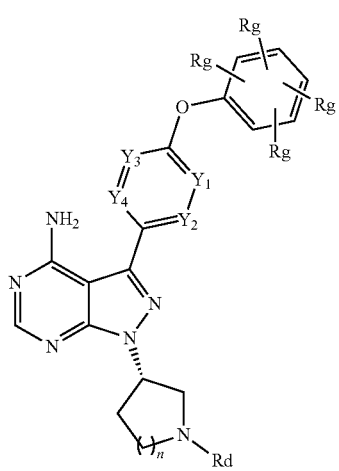

II' or their optical isomers, or pharmaceutically acceptable salts or solvates thereof;

where each Rg is independently H, halogen, —CF$_2$H, —CF$_3$, —CN, C1-C3 alkyl, or C1-C3 alkoxy;

n is selected from 0, 1 and 2;

Rd is selected from

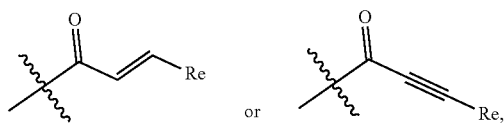

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl may be further substituted with amino, hydroxyl, and C1-C3 alkyl;

$Y_1$, $Y_2$, $Y_3$ and $Y_4$ are independently selected from C(Rf) and N, and at least one of $Y_1$, $Y_2$, $Y_3$ and $Y_4$ is N, wherein Rf is selected from H, halogen, C1-C3 alkyl, —CF$_3$, and —CF$_2$H.

Still further, the preferred compound of the present invention has a structure of Formula III or Formula III' or Formula III":

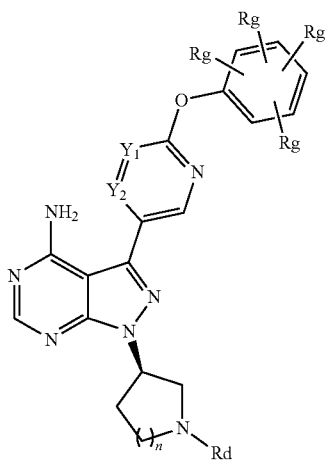

III

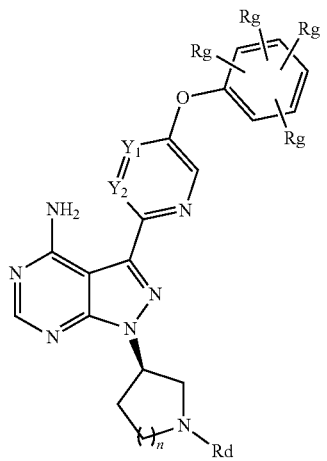

III'

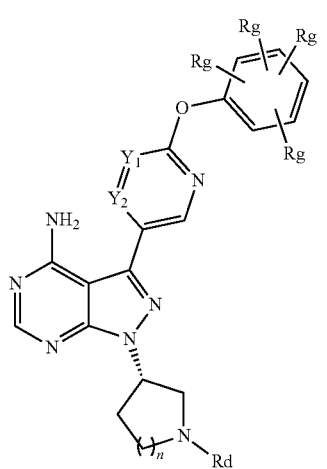

III"

and their optical isomers, or pharmaceutically acceptable salts or solvates thereof;

where each Rg is independently H, halogen, —CF$_2$H, —CF$_3$, C1-C3 alkyl, or C1-C3 alkoxy;

n is selected from 0, 1 and 2;

Rd is selected from

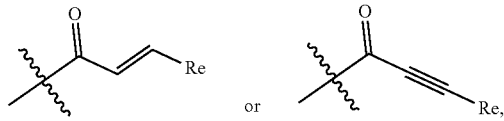

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl may be further substituted with amino, hydroxyl, and C1-C3 alkyl;

Y$_1$ and Y$_2$ are independently selected from C(Rf) and N, wherein Rf is selected from H, halogen, C1-C3 alkyl, —CF$_3$, and —CF$_2$H.

Still further, the preferred compound of the present invention has a structure of Formula IV or Formula IV' or Formula IV":

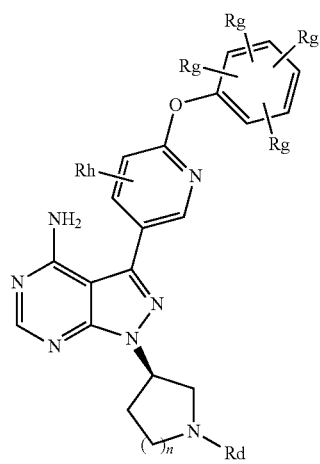

IV

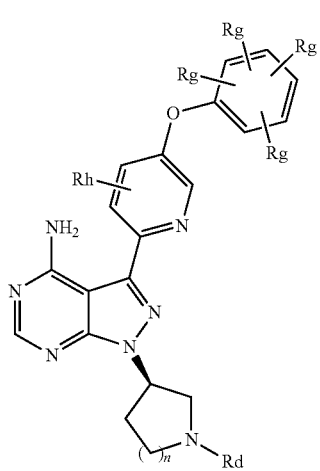

IV'

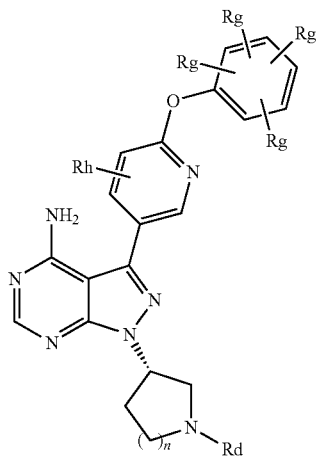

IV"

and optical isomers thereof, or pharmaceutically acceptable salts or solvates of the compound and the optical isomers thereof;

where each Rg is independently H, halogen, —CF$_2$H, —CF$_3$, C1-C3 alkyl, or C1-C3 alkoxy;

n is selected from 0, 1 and 2;

Rd is selected from

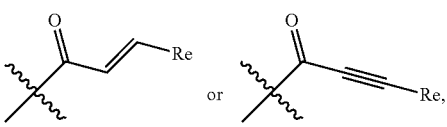

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl may be further substituted with amino, hydroxyl, and C1-C3 alkyl;

Rh is selected from H, halogen, C1-C3 alkyl, —CF$_3$, and —CF$_2$H; and Rh represents a substituent at any position on a benzene ring.

Still further, the preferred compound of the present invention has a structure of Formula V or Formula V' or Formula V":

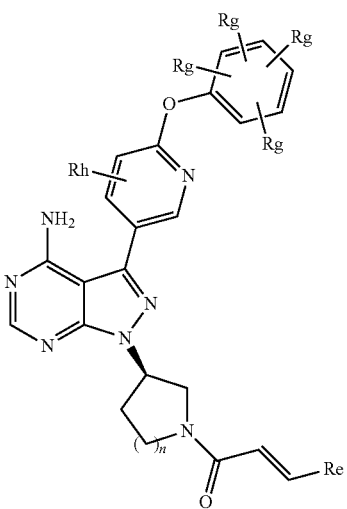

V

-continued

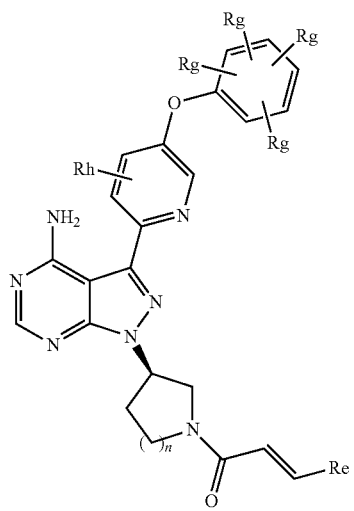

V'

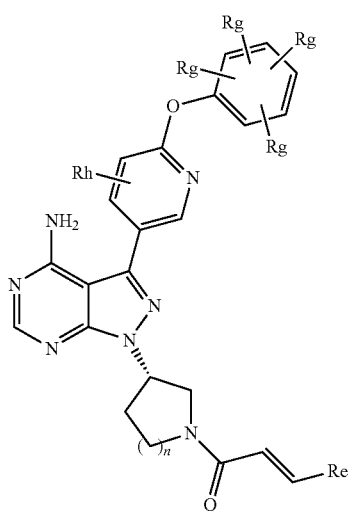

V''

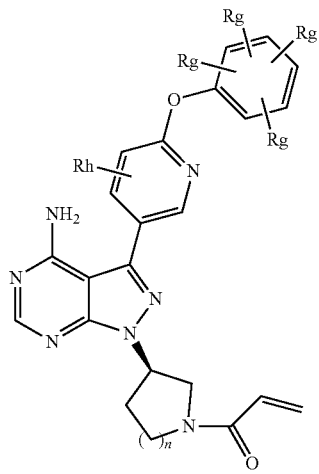

VI

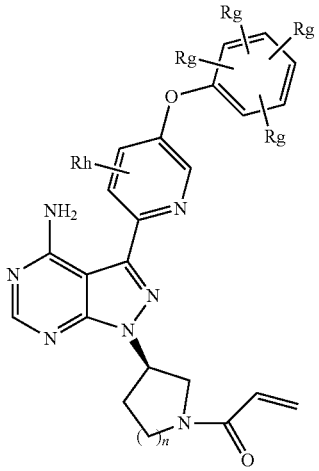

VI'

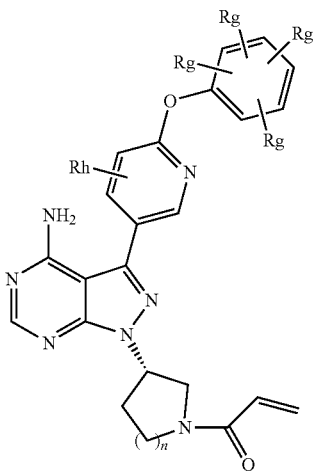

VI'' and their optical isomers, or pharmaceutically acceptable salts or solvates thereof;

where each Rg is independently H, halogen, —CF$_2$H, —CF$_3$, C1-C3 alkyl, or C1-C3 alkoxy;

n is selected from 0, 1 and 2;

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl may be further substituted with amino, hydroxyl, and C1-C3 alkyl;

Rh is selected from H, halogen, C1-C3 alkyl, —CF$_3$, and —CF$_2$H.

Still further, the preferred compound of the present invention has a structure of Formula VI or Formula VI' or Formula VI'':

and their optical isomers, or pharmaceutically acceptable salts or solvates thereof;

where each Rg is independently H, halogen, —CF$_2$H, —CF$_3$, C1-C3 alkyl, or C1-C3 alkoxy;

n is selected from 0, 1 and 2; Rh is selected from H, halogen, C1-C3 alkyl, —CF$_3$, and —CF$_2$H.

Still further, the preferred compound has a structure of Formula VI-a or Formula VI-a' or Formula VI-a'':

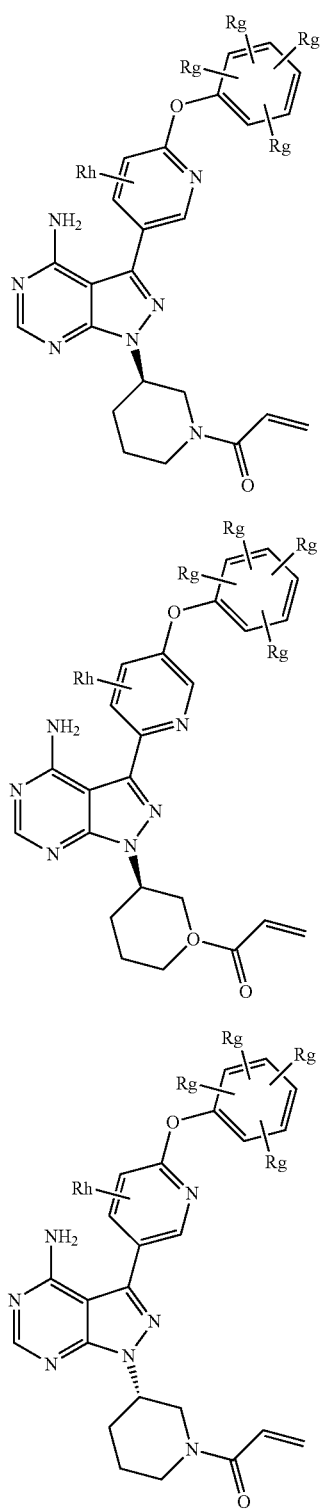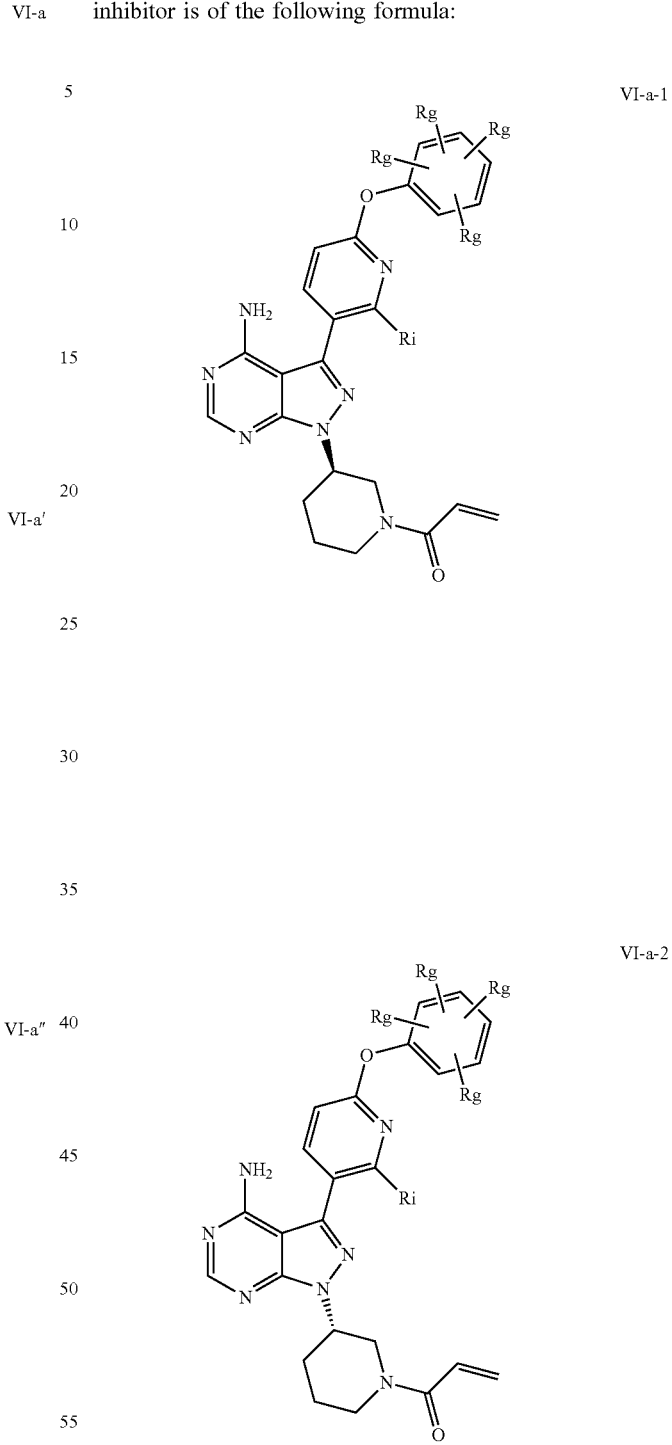

and their optical isomers, or pharmaceutically acceptable salts or solvates thereof;

where each Rg is independently H, halogen, CF₂H, —CF₃, C1-C3 alkyl, or C1-C3 alkoxy;

Rh is selected from H, halogen, C1-C3 alkyl, —CF₃, and —CF₂H.

As a further preference, the Bruton's tyrosine kinase inhibitor is of the following formula:

where each Rg is independently H, halogen, —CF₂H, —CF₃, C1-C3 alkyl, or C1-C3 alkoxy, preferably H, F, Cl, methyl, or methoxy; Ri is independently selected from H, halogen, C1-C3 alkyl, —CF₃, or —CF₂H, preferably from H or F.

Still further, according to the structure of Formula VI or Formula VI' or Formula VI", the preferred compound of the present invention has a structure of Formula VII or Formula VII' or Formula VII":

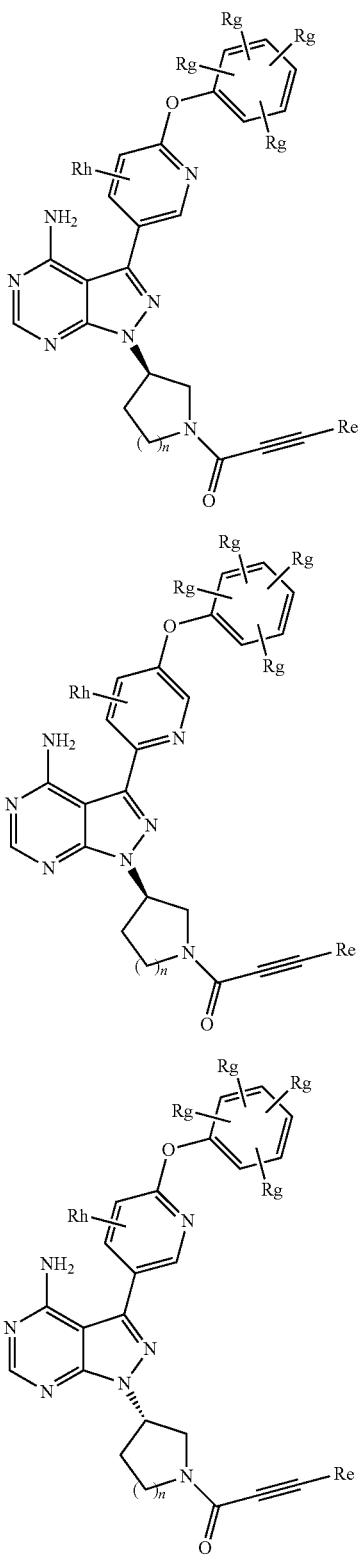

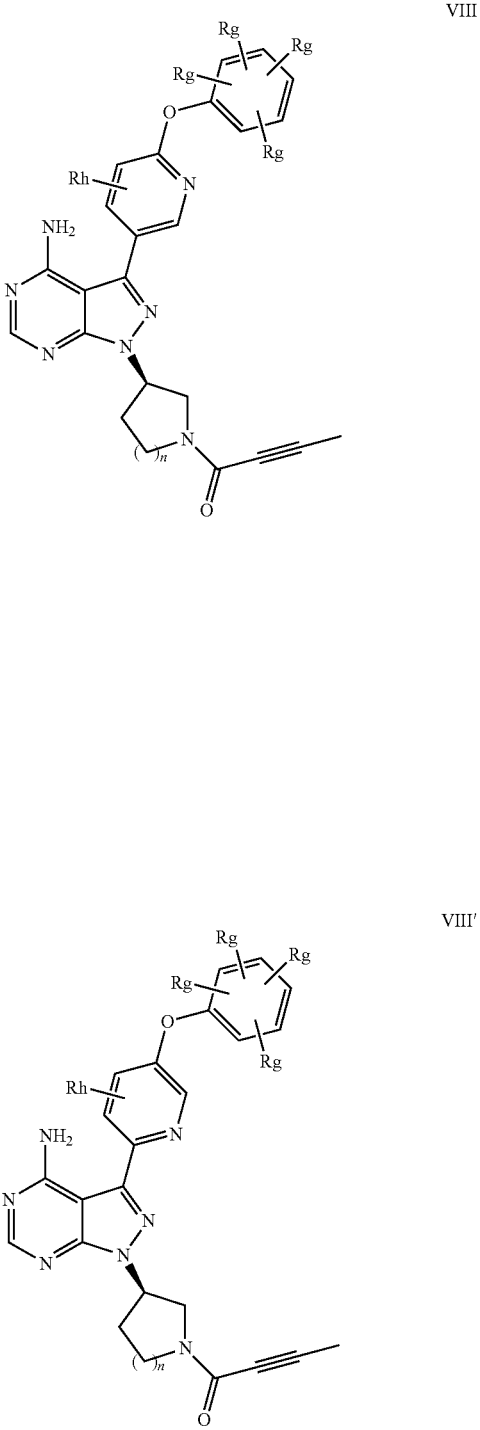

and their optical isomers, or pharmaceutically acceptable salts or solvates thereof;

where each Rg is independently H, halogen, —CF$_2$H, —CF$_3$, C1-C3 alkyl, or C1-C3 alkoxy;

n is selected from 0, 1 and 2;

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl may be further substituted with amino, hydroxyl, and C1-C3 alkyl;

Rh is selected from H, halogen, C1-C3 alkyl, —CF$_3$, and —CF$_2$H.

Still further, the preferred compound of the present invention has a structure of Formula VIII or Formula VIII' or Formula VIII":

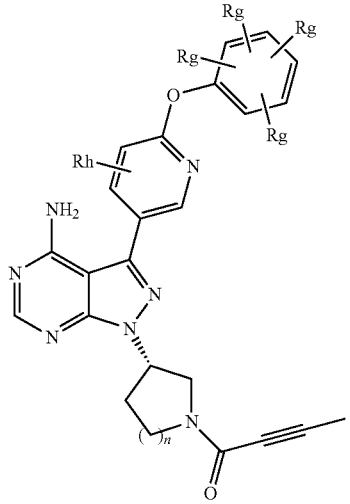
and their optical isomers, or pharmaceutically acceptable salts or solvates thereof;
where each Rg is independently H, halogen, —CF$_2$H, —CF$_3$, C1-C3 alkyl, or C1-C3 alkoxy;
n is selected from 0, 1 and 2;
Rh is selected from H, halogen, C1-C3 alkyl, —CF$_3$, and —CF$_2$H.
Preferably, the Bruton's tyrosine kinase inhibitors are preferably the following specific compounds:
| No. | Structure |
|---|---|
| 15a | 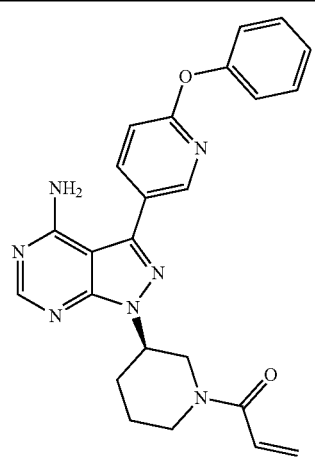 |
| 15b | 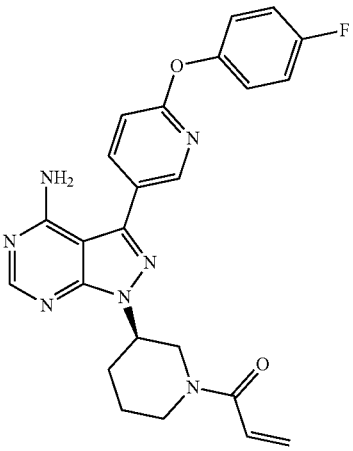 [SMILES: C=CC(=O)N1CCC[C@@H](n2nc(-c3ccc(Oc4ccc(F)cc4)nc3)c3c(N)ncnc32)C1] |
| 15c | 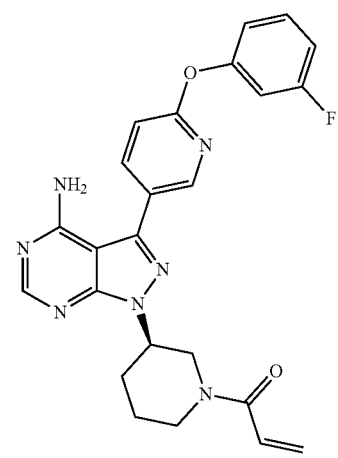 [SMILES: C=CC(=O)N1CCC[C@@H](n2nc(-c3ccc(Oc4cccc(F)c4)nc3)c3c(N)ncnc32)C1] |
| 15d | 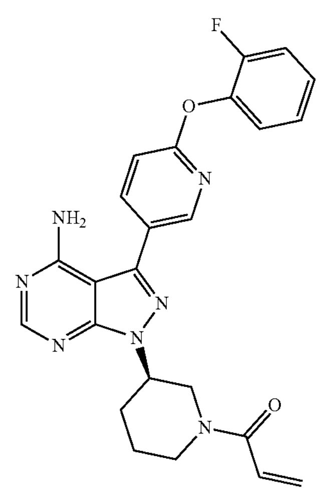 [SMILES: C=CC(=O)N1CCC[C@@H](n2nc(-c3ccc(Oc4ccccc4F)nc3)c3c(N)ncnc32)C1] |

| No. | Structure |
|---|---|
| 15e | 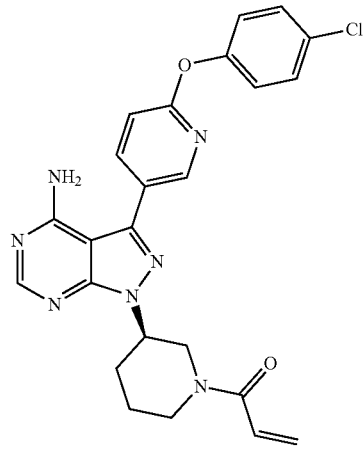 [SMILES: C=CC(=O)N1CCC[C@@H](n2nc(-c3ccc(Oc4ccc(Cl)cc4)nc3)c3c(N)ncnc32)C1] |
| 15f | 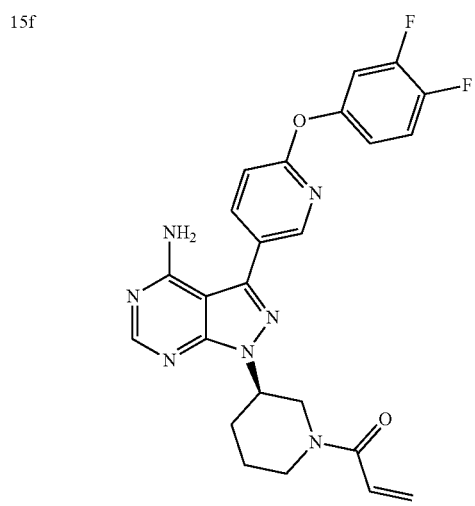 |
| 15g | 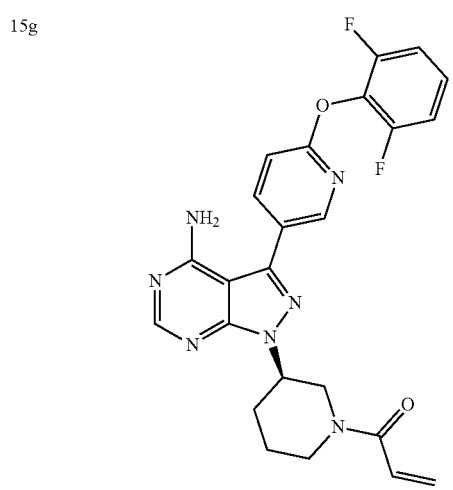 |
| No. | Structure |
|---|---|
| 15h | 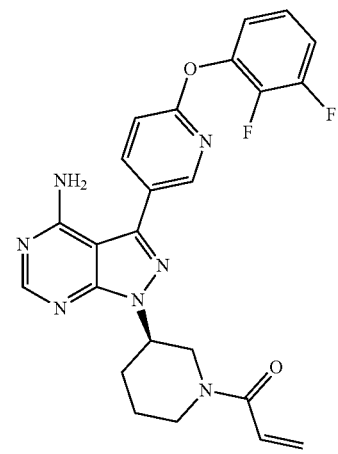 [SMILES: C=CC(=O)N1CCC[C@@H](n2nc(-c3ccc(Oc4cccc(F)c4F)nc3)c3c(N)ncnc32)C1] |
| 15i | 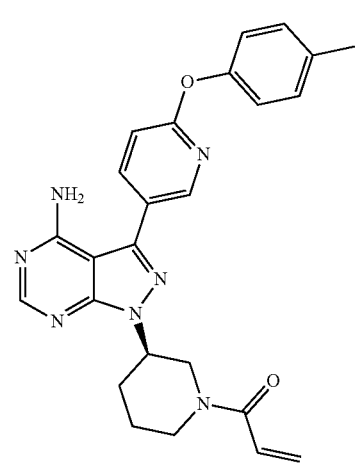 [SMILES: C=CC(=O)N1CCC[C@@H](n2nc(-c3ccc(Oc4ccc(C)cc4)nc3)c3c(N)ncnc32)C1] |
| 15j | 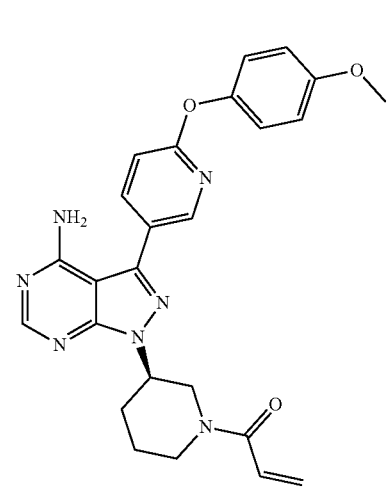 [SMILES: C=CC(=O)N1CCC[C@@H](n2nc(-c3ccc(Oc4ccc(OC)cc4)nc3)c3c(N)ncnc32)C1] |

| No. | Structure |
|---|---|
| 15k | 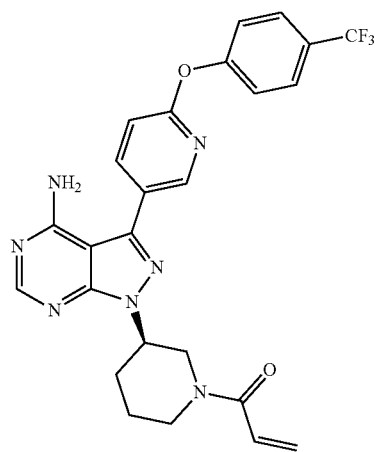 [SMILES: C=CC(=O)N1CCC[C@@H](n2nc(-c3ccc(Oc4ccc(C(F)(F)F)cc4)nc3)c3c(N)ncnc32)C1] |
| 16a | 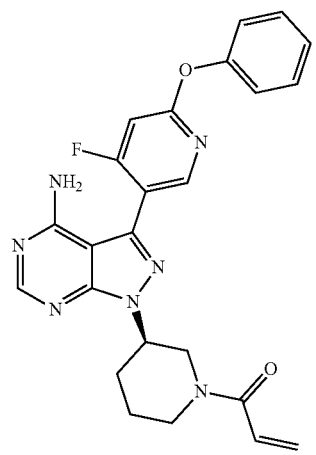 [SMILES: C=CC(=O)N1CCC[C@@H](n2nc(-c3cnc(Oc4ccccc4)cc3F)c3c(N)ncnc32)C1] |
| 16b | 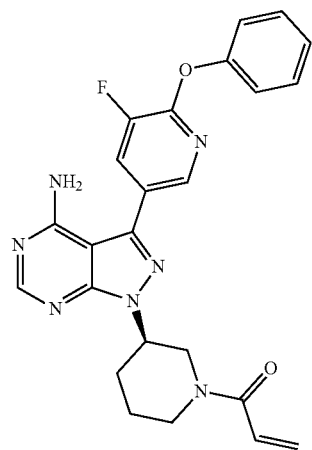 [SMILES: C=CC(=O)N1CCC[C@@H](n2nc(-c3cnc(Oc4ccccc4)c(F)c3)c3c(N)ncnc32)C1] |
| No. | Structure |
|---|---|
| 16c | 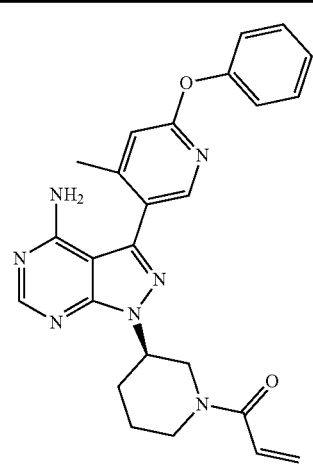 |
| 16d | 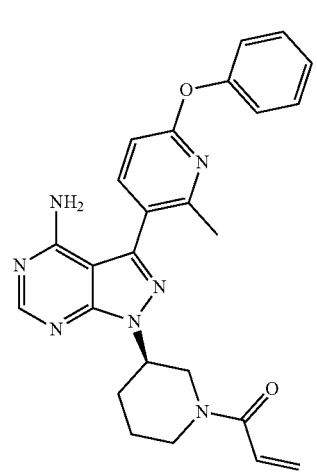 [SMILES: C=CC(=O)N1CCC[C@@H](n2nc(-c3ccc(Oc4ccccc4)nc3C)c3c(N)ncnc32)C1] |
| 17a | 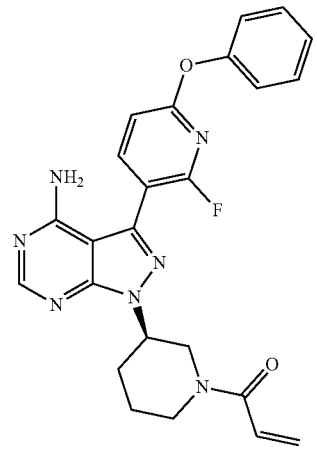 [SMILES: C=CC(=O)N1CCC[C@@H](n2nc(-c3ccc(Oc4ccccc4)nc3F)c3c(N)ncnc32)C1] |

| No. | Structure |
|---|---|
| 17b | 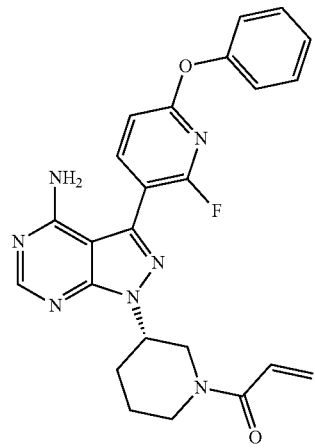 [SMILES: C=CC(=O)N1CCC[C@H](n2nc(-c3ccc(Oc4ccccc4)nc3F)c3c(N)ncnc32)C1] |
| 17c | 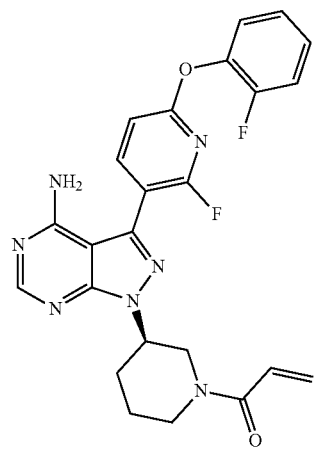 [SMILES: C=CC(=O)N1CCC[C@@H](n2nc(-c3ccc(Oc4ccccc4F)nc3F)c3c(N)ncnc32)C1] |
| 17d | 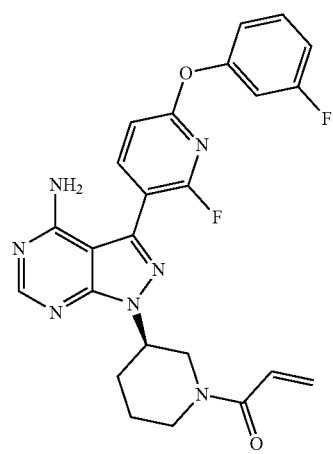 [SMILES: C=CC(=O)N1CCC[C@@H](n2nc(-c3ccc(Oc4cccc(F)c4)nc3F)c3c(N)ncnc32)C1] |
| No. | Structure |
|---|---|
| 17e | 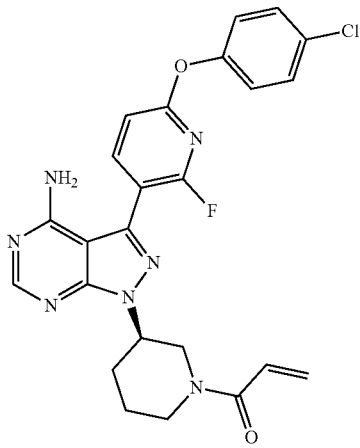 [SMILES: C=CC(=O)N1CCC[C@@H](n2nc(-c3ccc(Oc4ccc(Cl)cc4)nc3F)c3c(N)ncnc32)C1] |
| 17f | 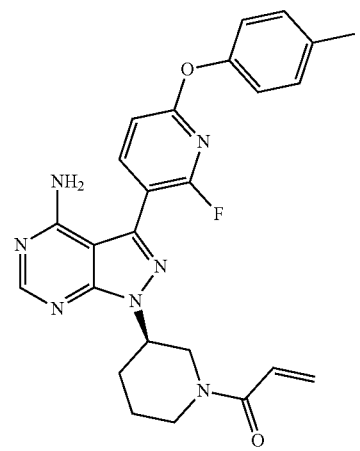 [SMILES: C=CC(=O)N1CCC[C@@H](n2nc(-c3ccc(Oc4ccc(C)cc4)nc3F)c3c(N)ncnc32)C1] |
| 17g | 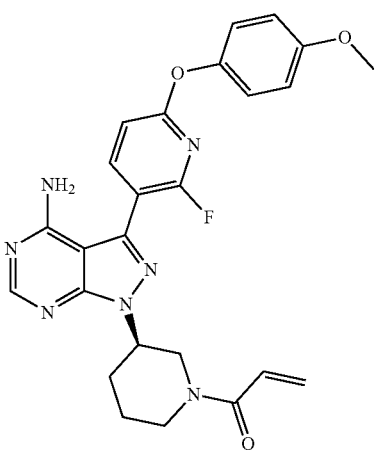 [SMILES: C=CC(=O)N1CCC[C@@H](n2nc(-c3ccc(Oc4ccc(OC)cc4)nc3F)c3c(N)ncnc32)C1] |

| No. | Structure |
|---|---|
| 17h | 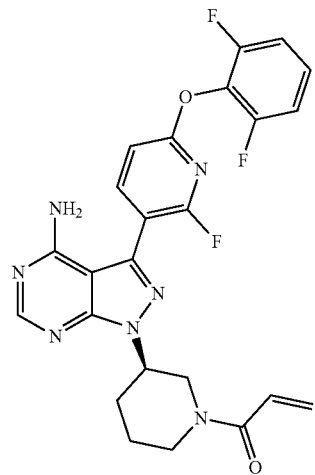 [SMILES: C=CC(=O)N1CCC[C@@H](n2nc(-c3ccc(Oc4c(F)cccc4F)nc3F)c3c(N)ncnc32)C1] |
| 17i | 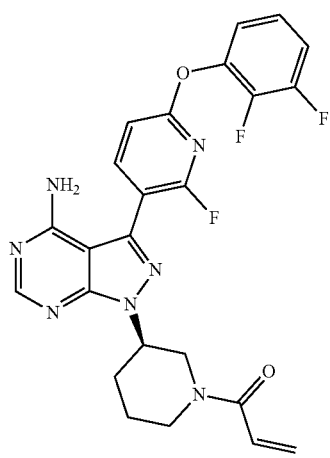 [SMILES: C=CC(=O)N1CCC[C@@H](n2nc(-c3ccc(Oc4cccc(F)c4F)nc3F)c3c(N)ncnc32)C1] |
| 18 | 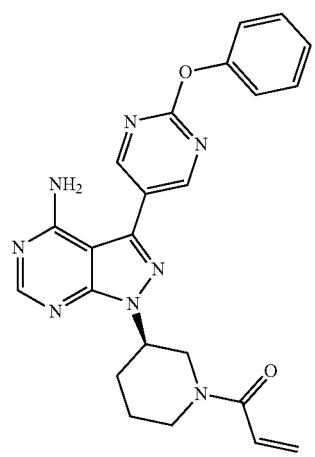 [SMILES: C=CC(=O)N1CCC[C@@H](n2nc(-c3cnc(Oc4ccccc4)nc3)c3c(N)ncnc32)C1] |
| 19 | 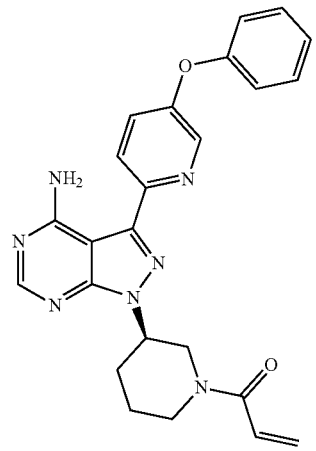 [SMILES: C=CC(=O)N1CCC[C@@H](n2nc(-c3ccc(Oc4ccccc4)cn3)c3c(N)ncnc32)C1] |
| 20a | 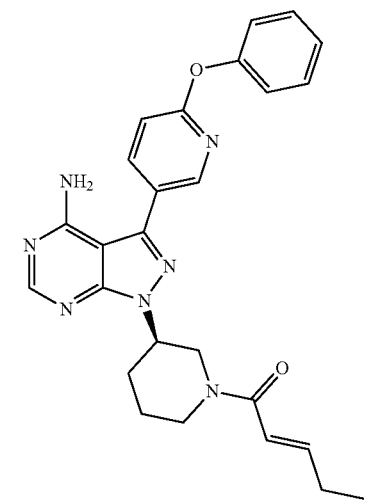 [SMILES: CC/C=C/C(=O)N1CCC[C@@H](n2nc(-c3ccc(Oc4ccccc4)nc3)c3c(N)ncnc32)C1] |
| 20b | 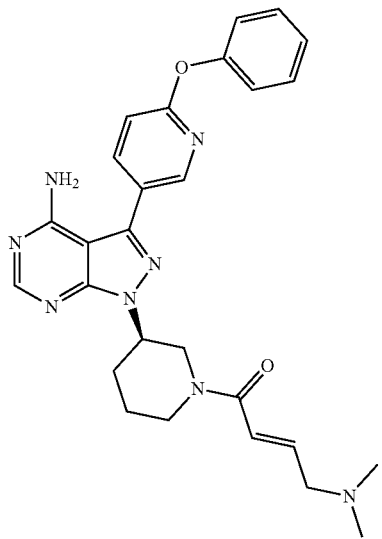 [SMILES: CN(C)C/C=C/C(=O)N1CCC[C@@H](n2nc(-c3ccc(Oc4ccccc4)nc3)c3c(N)ncnc32)C1] |

| No. | Structure |
|---|---|
| 20c | 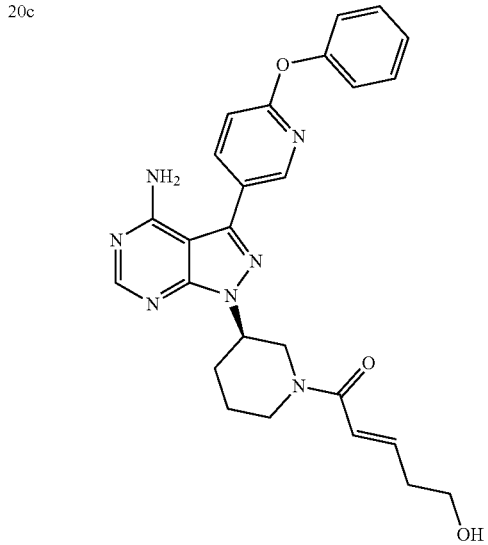 |
| 21a | 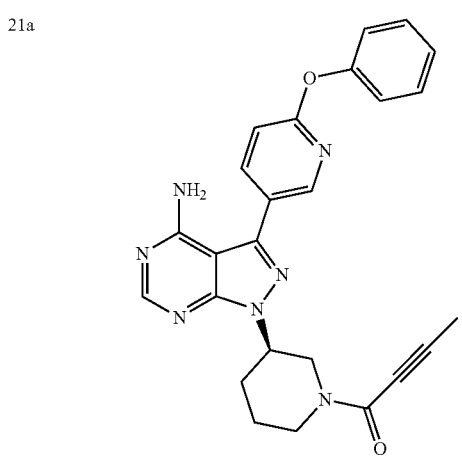 |
| 21b | 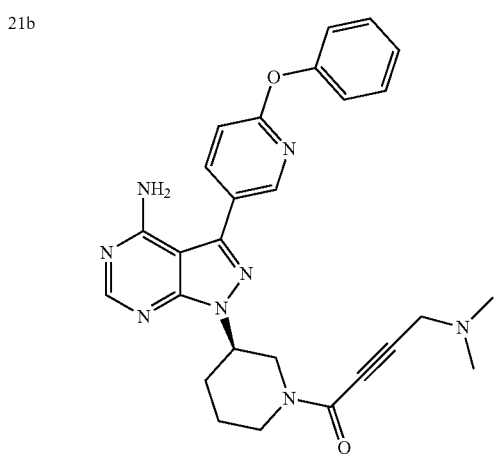 |
| No. | Structure |
|---|---|
| 21c | 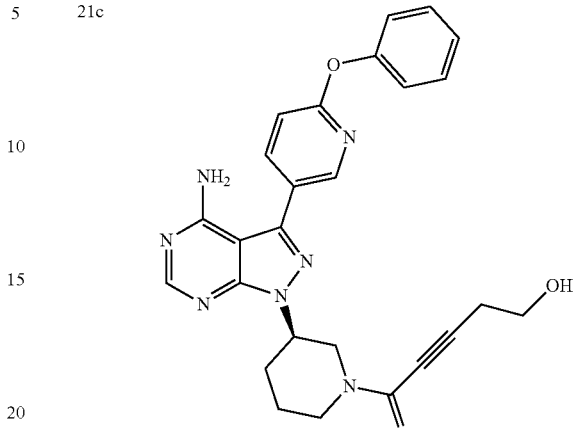 |
| 22 | 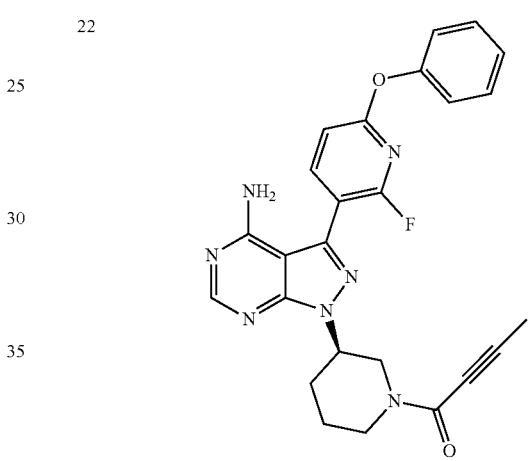 |
| 23a |  |

-continued
| No. | Structure |
|---|---|
| 23b | 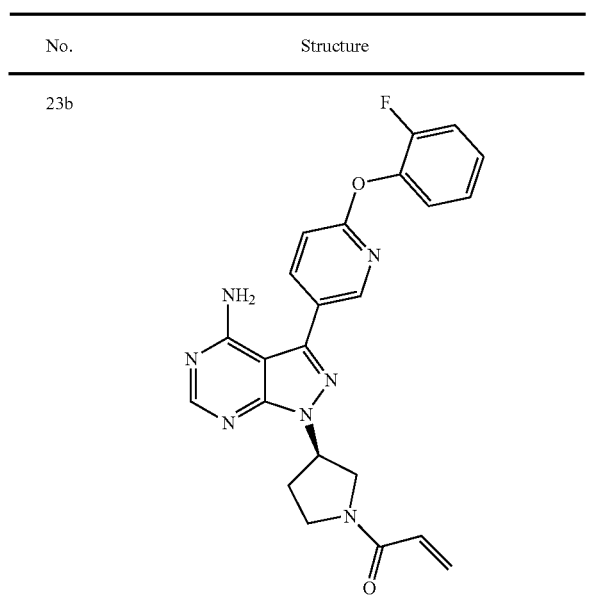 |
| 23c | 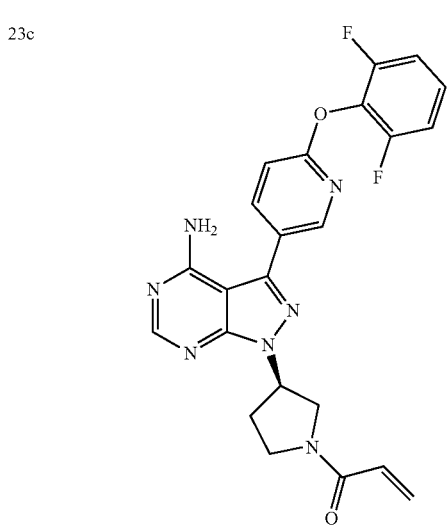 |
| 23d | 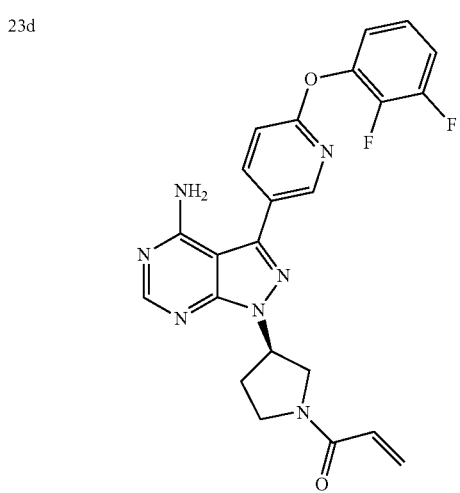 |
-continued
| No. | Structure |
|---|---|
| 24a | 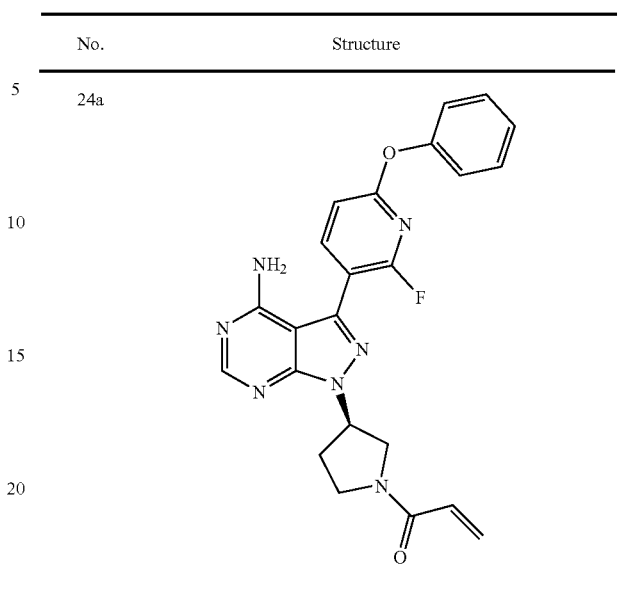 |
| 24b | 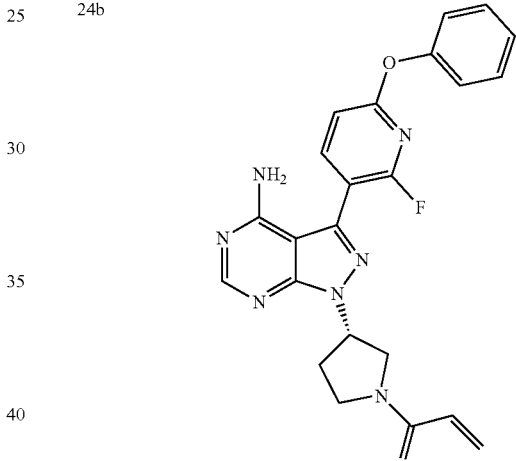 |
| 24c | 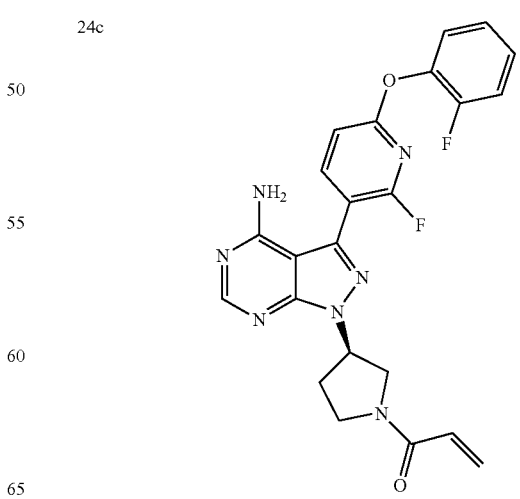 |

| No. | Structure |
|---|---|
| 24d | (structure) |
| 24e | (structure) |
| 25a | (structure) |
| 25b | (structure) | and their optical isomers, or pharmaceutically acceptable salts or solvates. Preferably, the compounds and representative numerals are as follows:

(R)-1-(3-(4-amino-3-(6-phenoxypyridin-3-yl)-1H-pyrazolo[3,4-d]pyrimidin-1-yl)piperidin-1-yl) prop-2-en-1-one (15a)

(R)-1-(3-(4-amino-3-(6-(4-fluorophenoxypyridine)-3-yl)-1H-pyrazolo[3,4-d]pyrimidin-1-yl)piperidin-1-yl)prop-2-en-1-one (15b)

(R)-1-(3-(4-amino-3-(6-(3-fluorophenoxypyridine)-3-yl)-1H-pyrazolo[3,4-d]pyrimidin-1-yl)piperidin-1-yl)prop-2-en-1-one (15c)

(R)-1-(3-(4-amino-3-(6-(2-fluorophenoxypyridine)-3-yl)-1H-pyrazolo[3,4-d]pyrimidin-1-yl)piperidin-1-yl)prop-2-en-1-one (15d)

(R)-1-(3-(4-amino-3-(6-(4-chlorophenoxypyridine)-3-yl)-1H-pyrazolo[3,4-d]pyrimidin-1-yl) piperidin-1-yl)prop-2-en-1-one (15e)

(R)-1-(3-(4-amino-3-(6-(3,4-difluorophenoxypyridine)-3-yl)-1H-pyrazolo[3,4-d]pyrimidin-1-yl)piperidin-1-yl) prop-2-en-1-one (15f)

(R)-1-(3-(4-amino-3-(6-(2,6-difluorophenoxypyridine)-3-yl)-1H-pyrazolo[3,4-d]pyrimidin-1-yl)piperidin-1-yl) prop-2-en-1-one (15g)

(R)-1-(3-(4-amino-3-(6-(2,3-difluorophenoxypyridine)-3-yl)-1H-pyrazolo[3,4-d]pyrimidin-1-yl)piperidin-1-yl) prop-2-en-1-one (15h)

(R)-1-(3-(4-amino-3-(6-(4-methylphenoxypyridine)-3-yl)-1H-pyrazolo[3,4-d]pyrimidin-1-yl piperidin-1-yl)prop-2-en-1-one (15i)

(R)-1-(3-(4-amino-3-(6-(4-methoxyphenoxypyridine)-3-yl)-1H-pyrazolo[3,4-d]pyrimidin-1-piperidin-1-yl)prop-2-en-1-one (15j)

(R)-1-(3-(4-amino-3-(6-(4-trifluoromethylphenoxypyridine)-3-yl)-1H-pyrazolo[3,4-d]pyrimidin-1-yl)piperidin-1-yl)prop-2-en-1-one (15k)

(R)-1-(3-(4-amino-3-(4-fluoro-6-phenoxypyridin-3-yl)-1H-pyrazolo[3,4-d]pyrimidin-1-yl)piperidin-1-yl)prop-2-en-1-one (16a)

(R)-1-(3-(4-amino-3-(5-fluoro-6-phenoxypyridin-3-yl)-1H-pyrazolo[3,4-d]pyrimidin-1-yl)piperidin-1-yl)prop-2-en-1-one (16b)

(R)-1-(3-(4-amino-3-(4-methyl-6-phenoxypyridin-3-yl)-1H-pyrazolo[3,4-d]pyrimidin-1-yl) piperidin-1-yl)prop-2-en-1-one (16c)

(R)-1-(3-(4-amino-3-(2-methyl-6-phenoxypyridin-3-yl)-1H-pyrazolo[3,4-d]pyrimidin-1-yl) piperidin-1-yl)prop-2-en-1-one (16d)

(R)-1-(3-(4-amino-3-(2-fluoro-6-phenoxypyridin-3-yl)-1H-pyrazolo[3,4-d]pyrimidin-1-yl)piperidin-1-yl)prop-2-en-1-one (17a)

(S)-1-(3-(4-amino-3-(2-fluoro-6-phenoxypyridin-3-yl)-1H-pyrazolo[3,4-d]pyrimidin-1-yl)piperidin-1-yl)prop-2-en-1-one (17b)

(R)-1-(3-(4-amino-3-(2-fluoro-6-(2-fluorophenoxy)pyridin-3-yl)-1H-pyrazolo[3,4-d]pyrimidin-1-yl)piperidin-1-yl)prop-2-en-1-one (17c)

(R)-1-(3-(4-amino-3-(2-fluoro-6-(3-fluorophenoxy)pyridin-3-yl)-1H-pyrazolo[3,4-d]pyrimidin-1-yl)piperidin-1-yl)prop-2-en-1-one (17d)

(R)-1-(3-(4-amino-3-(2-fluoro-6-(4-chlorophenoxy)pyridin-3-yl)-1H-pyrazolo[3,4-d]pyrimidin-1-yl)piperidin-1-yl)prop-2-en-1-one (17e)

(R)-1-(3-(4-amino-3-(2-fluoro-6-(4-methylphenoxy)pyridin-3-yl)-1H-pyrazolo[3,4-d]pyrimidin-1-yl)piperidin-1-yl)prop-2-en-1-one (17f)

(R)-1-(3-(4-amino-3-(2-fluoro-6-(4-methoxyphenoxy)pyridin-3-yl)-1H-pyrazolo[3,4-d]pyrimidin-1-yl)piperidin-1-yl)prop-2-en-1-one (17g)

(R)-1-(3-(4-amino-3-(6-(2,6-difluorophenoxy)-2-fluoropyridin-3-yl)-1H-pyrazolo[3,4-d]pyrimidin-1-yl)piperidin-1-yl)prop-2-en-1-one (17h)

(R)-1-(3-(4-amino-3-(6-(2,3-difluorophenoxy)-2-fluoropyridin-3-yl)-1H-pyrazolo[3,4-d]pyrimidin-1-yl)piperidin-1-yl)prop-2-en-1-one (17i)

(R)-1-(3-(4-amino-3-(2-phenoxypyrimidin-5-yl)-1H-pyrazolo[3,4-d]pyrimidin-1-yl)piperidin-1-yl)prop-2-en-1-one (18)

(R)-1-(3-(4-amino-3-(5-phenoxypyridin-2-yl)-1H-pyrazolo[3,4-d]pyrimidin-1-yl)piperidin-1-yl)prop-2-en-1-one (19)

(R)-1-(3-(4-amino-3-(6-phenoxypyridin-3-yl)-1H-pyrazolo[3,4-d]pyrimidin-1-yl)piperidin-1-yl) pent-2-en-1-one (20a)

(R)-1-(3-(4-amino-3-(6-phenoxypyridin-3-yl)-1H-pyrazolo[3,4-d]pyrimidin-1-yl)piperidin-1-yl)-4-(dimethylamino)but-2-en-1-one (20b)

(R)-1-(3-(4-amino-3-(6-phenoxypyridin-3-yl)-1H-pyrazolo[3,4-d]pyrimidin-1-yl)piperidin-1-yl)-5-hydroxypent-2-en-1-one (20c)

(R)-1-(3-(4-amino-3-(6-phenoxypyridin-3-yl)-1H-pyrazolo[3,4-d]pyrimidin-1-yl)piperidin-1-yl) but-2-yn-1-one (21a)

(R)-1-(3-(4-amino-3-(6-phenoxypyridin-3-yl)-1H-pyrazolo[3,4-d]pyrimidin-1-yl)piperidin-1-yl)-4-(dimethylamino)but-2-yn-1-one (21b)

(R)-1-(3-(4-amino-3-(6-phenoxypyridin-3-yl)-1H-pyrazolo[3,4-d]pyrimidin-1-yl)piperidin-1-yl)-5-hydroxypent-2-yn-1-one (21c)

(R)-1-(3-(4-amino-3-(2-fluoro-6-phenoxypyridin-3-yl)-1H-pyrazolo[3,4-d]pyrimidin-1-yl)piperidin-1-yl)but-2-yn-1-one (22)

(R)-1-(3-(4-amino-3-(6-phenoxypyridin-3-yl)-1H-pyrazolo[3,4-d]pyrimidin-1-yl)pyrrolidin-1-yl)prop-2-en-1-one (23a)

(R)-1-(3-(4-amino-3-(6-(2-fluorophenoxy)pyridin-3-yl)-1H-pyrazolo[3,4-d]pyrimidin-1-yl) pyrrolidin-1-yl)prop-2-en-1-one (23b)

(R)-1-(3-(4-amino-3-(6-(2,6-difluorophenoxy)pyridin-3-yl)-1H-pyrazolo[3,4-d]pyrimidin-1-yl) pyrrolidin-1-yl)prop-2-en-1-one (23c)

(R)-1-(3-(4-amino-3-(6-(2,3-difluorophenoxy)pyridin-3-yl)-1H-pyrazolo[3,4-d]pyrimidin-1-yl) pyrrolidin-1-yl)prop-2-en-1-one (23d)

(R)-1-(3-(4-amino-3-(2-fluoro-6-phenoxypyridin-3-yl)-1H-pyrazolo[3,4-d]pyrimidin-1-yl)pyrrolidin-1-yl)prop-2-en-1-one (24a)

(S)-1-(3-(4-amino-3-(2-fluoro-6-phenoxypyridin-3-yl)-1H-pyrazolo[3,4-d]pyrimidin-1-yl)pyrrolidin-1-yl)prop-2-en-1-one (24b)

(R)-1-(3-(4-amino-3-(2-fluoro-6-(2-fluorophenoxy)pyridin-3-yl)-1H-pyrazolo[3,4-d]pyrimidin-1-yl) pyrrolidin-1-yl)prop-2-en-1-one (24c)

(R)-1-(3-(4-amino-3-(6-(2,6-difluorophenoxy)-2-fluoropyridin-3-yl)-1H-pyrazolo[3,4-d]pyrimidin-1-yl) pyrrolidin-1-yl)prop-2-en-1-one (24d)

(R)-1-(3-(4-amino-3-(6-(2,3-difluorophenoxy)-2-fluoropyridin-3-yl)-1H-pyrazolo[3,4-d]pyrimidin-1-yl) pyrrolidin-1-yl)prop-2-en-1-one (24e)

(R)-1-(3-(4-amino-3-(6-phenoxypyridin-3-yl)-1H-pyrazolo[3,4-d]pyrimidin-1-yl)pyrrolidin-1-yl)but-2-yn-1-one (25a)

(S)-1-(3-(4-amino-3-(6-phenoxypyridin-3-yl)-1H-pyrazolo[3,4-d]pyrimidin-1-yl)pyrrolidin-1-yl)but-2-yn-1-one (25b)

and their optical isomers, or pharmaceutically acceptable salts or solvates.

Description of Terms

The term "aryl", as used in the present invention, refers to an all-carbon monocyclic or fused polycyclic group with 5 to 12 carbon atoms, having a fully conjugated π electron system. Non-limiting examples of an aromatic ring are: benzene ring, naphthalene ring, and anthracene ring. The aromatic ring may be unsubstituted or substituted. The substituent of the aromatic ring is selected from halogen (preferably fluoro, chloro, bromo, iodo), nitro, amino, C1-C6 alkyl (preferably methyl, ethyl, propyl, isopropyl, butyl, isobutyl, sec-butyl, tert-butyl, etc.), C1-C6 alkoxy (preferably methoxy, ethoxy, propoxy, isopropyloxy, butoxy, isobutyloxy, sec-butoxy, tert-butyloxy, etc.), halogenated C1-C6 alkyl (preferably methyl, ethyl, propyl, isopropyl, butyl, isobutyl, sec-butyl, tert-butyl, etc.), halogenatedC1-C6alkoxy (preferably methoxy, ethoxy, propoxy, isopropyloxy, butoxy, isobutyloxy, sec-butyloxy, tert-butoxy, etc.), C3-C6cycloalkyl (preferably cyclopropyl, cyclopentyl, cyclohexyl, etc.), and halogenated C3-C6cycloalkyl (preferablycyclopropyl, cyclopentyl, cyclohexyl, etc.). The substitution of the aromatic ring may be a mono-substitution (such as an ortho, meta or para substitution), or a di- or tri-substitution.

The term "heteroaryl", as used in the present invention, refers to an unsaturated cyclic group with 5 to 12 cyclic atoms, having a fully conjugated π-electron system, equivalent to one or more carbon atoms in the above "aryl" being replaced by heteroatoms such as oxygen atoms, nitrogen atoms and sulfur atoms. The heteroaryl ring may be a single ring or a bicycloring, that is, fused by two rings. Specifically, the heterocyclic aryl (heteroaryl) may be pyridyl, pyrimidinyl, pyrazinyl, isoxazolyl, isothiazolyl, pyrazolyl, thiazolyl, oxazolyl, imidazolyl, etc. The heterocyclic aryl may be unsubstituted or substituted. The substituent of the heterocyclic aryl is selected from halogen, nitro, amino, C1-C6 alkyl, C1-C6alkoxy, halogenated C1-C6 alkyl, halogenated C1-C6alkoxy, C3-C6cycloalkyl, and halogenated C3-C6cycloalkyl;

The term "halogen", as used in the present invention, refers to fluoro, chloro, bromo, iodo, preferably fluoro, chloro or bromo;

The term "C1-C3 alkyl", as used in the present invention, is preferably methyl, ethyl, etc.;

The term "C2-C6 alkyl", as used in the present invention, is preferably ethyl, propyl, isopropyl, etc.;

The term "n", as used in the present invention, is preferably 1 or 2;

The term "azaalkyl", as used in the present invention, refers to that one or more carbon atoms of C1-C6 alkyl are substituted by nitrogen atoms and preferably refers to

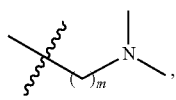

m=1, 2, 3,

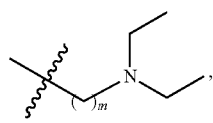

m=1, 2,

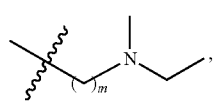

m=1, 2, 3 etc.

The term "oxaalkyl", as used in the present invention, refers to that one or more carbon atoms of C1-C6 alkyl are substituted by oxygen atoms and preferably refers to

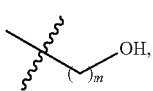

m=1, 2, 3,

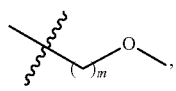

m=1, 2, 3, etc.

The term "alkoxy", as used in the present invention, refers to an —O-alkyl group where the alkyl is as defined above. Examples of "alkoxy" as used in the present invention include, but are not limited to, methoxy, ethoxy, n-propoxy, isopropoxy, n-butoxy and tert-butoxy. "Alkoxy" also includes substituted alkoxy. The alkoxy may be optionally substituted once or more times with a halogen.

The term "solvates", as used in the present invention, refers to variable stoichiometric complexes formed from solutes (e.g., the compounds of Formula I to Formula VIII of the present invention and the compounds of Formula IV' to Formula VIII') and solvents. For the object of the present invention, the solvents do not interfere with the biological activity of the solutes. The examples of suitable solvents include, but are not limited to, water, methanol, ethanol, and acetic acid. The preferred solvents are pharmaceutically acceptable solvents. The suitable pharmaceutically acceptable solvents include, but are not limited to, water, ethanol, and acetic acid. More preferably, the solvent used is water.

The salts of the compounds of the present invention may be prepared by the present invention using methods well known to those skilled in the art. The salts may be organic acid salts, inorganic acid salts, etc. The organic acid salts include citrates, fumarates, oxalates, malates, lactates, camphor sulfonates, p-toluenesulfonates, and mesylates. The inorganic acid salts include hydrohalides, sulfates, phosphates, and nitrates. For example, with lower alkylsulfonic acids such as methanesulfonic acid or trifluoromethanesulfonic acid, mesylate salts or triflate salts of the compounds may be formed; with arylsulfonic acids such as benzenesulfonic acid or p-toluenesulfonic acid, p-toluenesulfonates or besylates of the compounds may be formed; with organic carboxylic acids such as acetic acid, fumaric acid, tartaric acid, oxalic acid, maleic acid, malic acid, succinic acid or citric acid, corresponding salts of the compounds may be formed; with amino acids such as glutamic acid or aspartic acid, glutamates or aspartates of the compounds may be formed. Corresponding salts of the compounds may also be formed with inorganic acids such as hydrohalic acids (e.g., hydrofluoric acid, hydrobromic acid, hydroiodic acid, hydrochloric acid), nitric acid, carbonic acid, sulfuric acid or phosphoric acid.

The second object of the present invention is to provide a pharmaceutical composition, comprising one or more of the compounds of any one of the above-mentioned technical solutions. The pharmaceutical composition of the present invention may comprise one or more of the compounds described in any one of the above technical solutions and other compounds, or may comprise one or more of the compounds of any one of the above-mentioned technical solutions.

The present invention provides a pharmaceutical preparation comprising at least one active component, and the active component(s) is/are one or more of the compounds of any one of the above-mentioned technical solutions. The pharmaceutical preparation comprises at least one active component and one or more pharmaceutically acceptable carriers or excipients. The active component(s) may be any one or more of the BTK inhibitor compounds of the present invention, optical isomers of the compounds, pharmaceutically acceptable salts of the compounds or the optical isomers, and solvates of the compounds or the optical isomers.

The carriers include conventional diluents, excipients, fillers, binders, wetting agents, disintegrating agents, absorption enhancers, surfactants, adsorption carriers, and lubricants in the pharmaceutical field, and an odorant, a sweetener and the like may also be added if necessary.

The drug of the present invention may be prepared into various forms such as tablets, powders, granules, capsules, oral liquids and injectable preparations, and all the drugs in the above forms can be prepared according to a conventional method in the pharmaceutical field.

In another aspect, the present invention provides use of the compounds of Formula I to Formula VIII, Formula I' to Formula VIII', Formula III" to Formula VIII", and Formula VI-a Formula VI-a' and Formula VI-a" and optical isomers of the compounds, or pharmaceutically acceptable salts or solvates of the compounds and the optical isomers for inhibiting Bruton's tyrosine kinase (Btk) activity or treating diseases, disorders or conditions benefiting from the inhibition of the Bruton's tyrosine kinase activity.

In a further preferred solution, provided by the present invention is a method for inhibiting Bruton's tyrosine kinase activity of a subject by administering to the subject in need of a composition comprising a therapeutically effective amount of at least one of the compounds, where the compounds has a structure of Formula I to Formula III and Formula I' to Formula VIII, Formula III" to Formula VIII", and Formula VI-a, Formula VI-a' and Formula VI-a". In some embodiments, the subject in need is suffering from an autoimmune disease, such as inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjögren's syndrome, multiple sclerosis, Guillain-Barré syndrome, acute disseminated encephalomyelitis, Addison's disease, visual ocular palsy-myoclonus Syndrome, mandatory spondylitis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, generalized hair removal, Behçet's disease, chronic fatigue, familial dysautonomia, endometriosis, interstitial cystitis, neuromuscular rigidity, scleroderma or vulvar pain, and chronic graft-versus-host disease.

In a further embodiment, the subject in need has a cancer. In an implementation manner, the cancer is a B cell proliferation related disease, such as diffuse large B-cell lymphoma, follicular lymphoma, chronic lymphocytic lymphoma, chronic lymphocytic leukemia, B-cell pro-lymphocytic leukemia, Lymphocyte lymphoma/Waldenstrommacroglobulinemia, splenic marginal lymphoma, plasma cell myeloma, plasmacytoma, extranodal marginal zone B-cell lymphoma, lymph node marginal zone B cell lymphoma, mantle cell lymphoma, mediastinum (thymus) large B-cell lymphoma, intravascular large B-cell lymphoma, primary exudative lymphoma, Burkitt lymphoma/leukemia or lymphomatoid granulomatous disease.

The present invention further provides use of the compounds of the present invention or pharmaceutically acceptable salts thereof in preparation of a BTK inhibitor, in particular for the preparation of a drug for treatment of cell proliferation related diseases. The cell proliferation related diseases include cancers. In other words, the present invention also provides use of the compounds of Formula I to Formula VIII, Formula I' to Formula VIII', Formula III" to Formula VIII", and Formula VI-a Formula VI-a' and Formula VI-a" and optical isomers of the compounds, or pharmaceutically acceptable salts or solvates of the compounds and the optical isomers alone or in combination with other drugs for treating proliferation related diseases such as cancers. Antitumor drugs which may be used in combination with the compounds provided by the present invention or pharmaceutically acceptable salts of the compound include, but are not limited to, at least one of the following classes: mitotic inhibitors (such as vinblastine, vindesine, and vinorelbine); tubulin decomposition inhibitors (such as Taxol); alkylating agents (such as cisplatin, carboplatin and cyclophosphamide); antimetabolites (such as 5-fluorouracil, tegafur, methotrexate, cytarabine and Hydroxyurea); insertable antibiotics (such as arrhenone, mitomycin and bleomycin); enzymes (such as aspartate); topoisomerase inhibitors (such as etoricin and camptothecin); and biological response modifier (such as interferon).

It is demonstrated through experiments by the inventors of the present invention that the compounds of the present invention have anti-proliferation and inhibitory effects on tumor cell strains such as A549, MINO, OCI-LY10 and TMD-8, and shows an excellent anti-tumor activity in tumor models such as Mino subcutaneous xenografts, and can be applied to drugs for treating solid tumors or leukemia associated with cell proliferation in humans or animals.

It is demonstrated through experiments by the inventors of the present invention that the compounds of the present invention have excellent kinase selectivity.

It is demonstrated through experiments by the inventors of the present invention that the compounds of the present invention have low hERG channel blocking activity.

It is demonstrated through experiments by the inventors of the present invention that the compounds of the present invention have good pharmacokinetic properties and can be applied to the oral treatment of solid tumors or leukemia associated with cell proliferation or autoimmune diseases in humans or animals.

DETAILED DESCRIPTION OF THE INVENTION

The embodiments of the present invention are described below by way of examples, and those skilled in the art will understand that modifications or substitutions of the corresponding technical features, made according to the teachings of the prior art, are still within the scope of the present invention.

Example 1: Preparation of Intermediate 1a

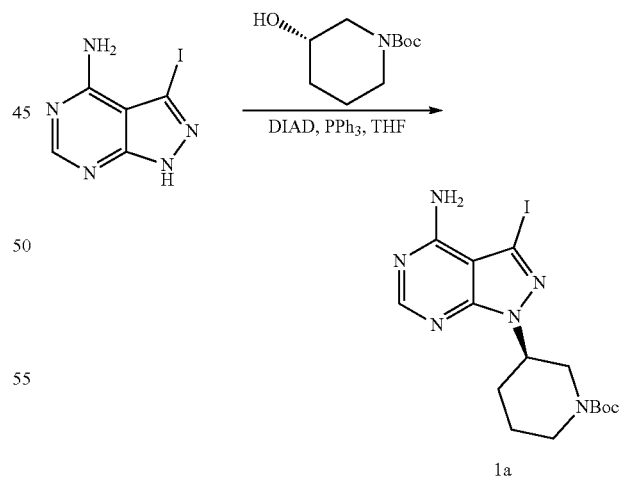

Operation Steps: 3-Iodo-4-Amino-1H-Pyrazolo[3,4-d]Pyrimidine (6.45 g, 24.7 Mmol), (S)-1-Boc-3-hydroxypiperidine (9.93 g, 49.4 mmol), and triphenylphosphine PPh3 (9.73 g, 37.1 mmol) were placed in a 250 mL round-bottom flask, a magnet was placed, 130 mL of THF was added, and the solution was stirred at room temperature in a nitrogen atmosphere; diisopropylazodicarboxylate DIAD (7.5 g, 37.1 mmol) was dissolved in about 30 mL of THF, and the solution was slowly added dropwise to the reaction system, and then the reaction was further carried out for about 12 hours. According to the results of TLC (thin layer chromatography), the reaction was stopped and reduced-pressure concentration was carried out; and purification was carried out by silica gel column chromatograph with petroleum ether-ethyl acetate as an eluting agent to obtain white solid 1a with a yield of 70%. 1H NMR (δ, CDCl₃): 1.45 (s, 9H), 1.54-1.76 (m, 1H), 181-1.97 (m, 1H), 2.05-2.26 (m, 1H), 2.75-2.96 (m, 1H), 3.48-3.61 (m, 1H), 4.13 (q, J=7.0 Hz, 2H), 4.65-4.88 (m, 1H), 6.45 (brs, 2H), 8.31 (s, 1H). LC-ESI-MS: 445 [M+H]. Chiral HPLC: 99% ee.

Example 2: Preparation of Intermediate 1b

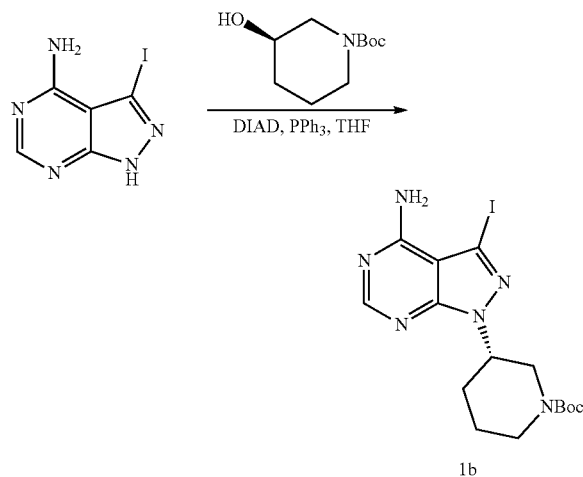

Operation steps: 3-iodo-4-amino-1H-pyrazolo[3,4-d]pyrimidine (6.45 g, 24.7 mmol), (R)-1-Boc-3-hydroxypiperidine (9.93 g, 49.4 mmol), and triphenylphosphine PPh3 (9.73 g, 37.1 mmol) were placed in a 250 mL round-bottom flask, a magnet was placed, 130 mL of THF was added, and the solution was stirred at room temperature in a nitrogen atmosphere. DIAD (7.5 g, 37.1 mmol) was dissolved in about 30 mL of THF, and the solution was slowly added dropwise to the reaction system, and then the reaction was further carried out for about 12 hours. According to the results of TLC, the reaction was stopped and reduced-pressure concentration was carried out; and purification was carried out by silica gel column chromatograph with petroleum ether-ethyl acetate as an eluting agent to obtain white solid 1b with a yield of 68%. LC-ESI-MS: 445 [M+H]. Chiral HPLC: 99% ee.

Example 3: Preparation of Intermediate 2a

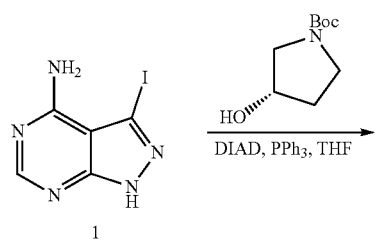

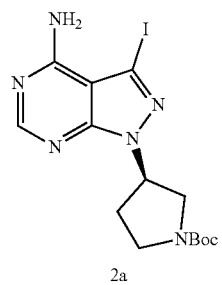

Operation steps: 3-iodo-4-amino-1H-pyrazolo[3,4-d]pyrimidine (5.1 g, 19.5 mmol), (S)-1-Boc-3-hydroxytetrahydropyrrole (7.3 g, 39 mmol), and triphenylphosphine PPh3 (7.7 g, 29.3 mmol) were placed in a 250 mL round-bottom flask, a magnet was placed, 100 mL of THF was added, and the solution was stirred at room temperature in a nitrogen atmosphere; DIAD (5.9 g, 29.3 mmol) was dissolved in about 25 mL of THF, and the solution was slowly added dropwise to the reaction system, and then the reaction was further carried out for about 12 hours. According to the results of TLC, the reaction was stopped and reduced-pressure concentration was carried out; and purification was carried out by silica gel column chromatograph with petroleum ether-ethyl acetate as an eluting agent to obtain white solid 2a with a yield of 35%. LC-ESI-MS: 431 [M+H]. Chiral HPLC: 98% ee.

Example 4: Preparation of Intermediate 2b

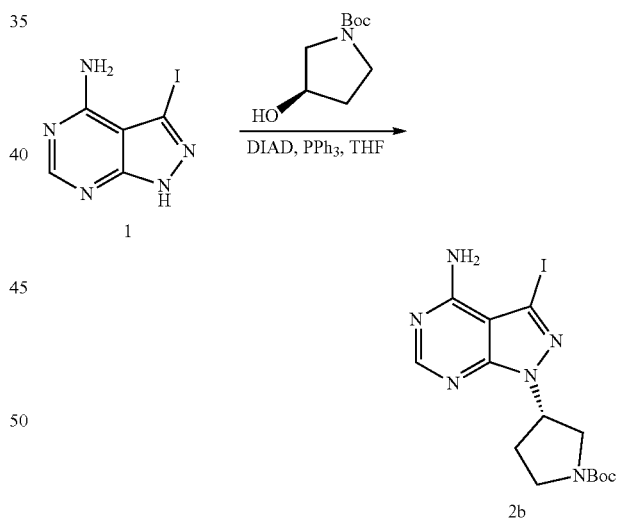

Operation steps: 3-iodo-4-amino-1H-pyrazolo[3,4-d]pyrimidine (5.1 g, 19.5 mmol), (R)-1-Boc-3-hydroxytetrahydropyrrole (7.3 g, 39 mmol), and triphenylphosphine PPh3 (7.7 g, 29.3 mmol) were placed in a 250 mL round-bottom flask, a magnet was placed, 100 mL of THF was added, and the solution was stirred at room temperature in a nitrogen atmosphere. DIAD (5.9 g, 29.3 mmol) was dissolved in about 25 mL of THF, and the solution was slowly added dropwise to the reaction system, and then the reaction was further carried out for about 12 hours; according to the results of TLC, the reaction was stopped and reduced-pressure concentration is carried out; and purification was carried out by silica gel column chromatograph with petroleum ether-ethyl acetate as an eluting agent to obtain white solid 2b with a yield of 32%. LC-ESI-MS: 431 [M+H]. Chiral HPLC: 98% ee.

Example 5. Preparation of Key Intermediates 3a-3k

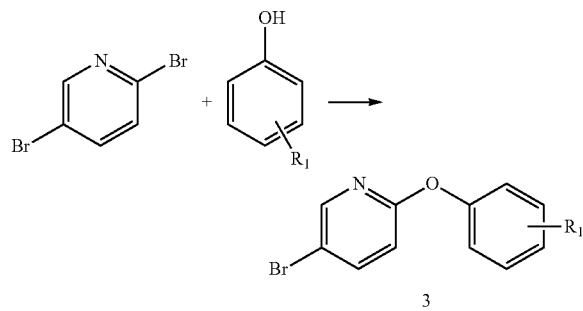

Operation steps (with intermediate 3a as an example): 2,5-dibromopyridine (61.5 mmol), phenol (64.6 mmol), CuI (6.15 mmol) and $Cs_2CO_3$ (92 mmol) were placed in a 250 mL dried flask; 150 mL of DMSO was added; TMEDA (6.15 mmol) was then added; and the solution was heated to 110° C. (the temperature unit in the present invention was in degree Celsius (° C.) unless otherwise specified) in an Ar atmosphere to carry out a reaction for about 20 hours until TLC transformation was complete. After the reaction system was cooled to room temperature, a large amount of ethyl acetate was added, rinsing with water was carried out four times, extraction with ethyl acetate was carried out twice, EA (ethyl acetate) phases were combined and rinsed with a saturated NaCl solution, and an organic phase was then dried, filtered and spin-dried, thus obtaining a brown oily product.

Intermediate 5-bromo-2-phenoxypyridine 3a ($R_1$=H), yield 92%, $^1$H NMR (400 MHz, $CDCl_3$): δ 8.22 (d, J=2.4 Hz, 1H), 7.76 (dd, J=8.7, 2.5 Hz, 1H), 7.41 (t, J=7.9 Hz, 2H), 7.22 (t, J=7.4 Hz, 1H), 7.12 (d, J=7.7 Hz, 2H), 6.83 (d, J=8.7 Hz, 1H). LC-ESI-MS: 250 [M+H].

Intermediate 3b (5-bromo-2-(4-fluoro-phenoxy)pyridine, $R_1$=4-fluoro): reagent: 2,5-dibromopyridine (6.15 mmol), 4-fluorophenol (6.46 mmol), CuI (0.62 mmol), $Cs_2CO_3$ (9.2 mmol), TMEDA (0.62 mmol), yield 82%, LC-ESI-MS: 268 [M+H].

Intermediate 3c (5-bromo-2-(3-fluoro-phenoxy)pyridine, $R_1$=3-fluoro): reagent: 2,5-dibromopyridine (6.15 mmol), 3-fluorophenol (6.46 mmol), CuI (0.61 mmol), $Cs_2CO_3$ (9.2 mmol), TMEDA (0.62 mmol), yield 70%, LC-ESI-MS: 268 [M+H].

Intermediate 3d (5-bromo-2-(2-fluoro-phenoxy)pyridine, $R_1$=2-fluoro): reagent: 2,5-dibromopyridine (6.15 mmol), 2-fluorophenol (6.46 mmol), CuI (0.61 mmol), $Cs_2CO_3$ (9.2 mmol), TMEDA (0.62 mmol), yield 65%, LC-ESI-MS: 268 [M+H].

Intermediate 3e (5-bromo-(4-chloro-phenoxy)pyridine, $R_1$=4-chloro): reagent: 2,5-dibromopyridine (6.15 mmol), 4-chlorophenol (6.46 mmol), CuI (0.61 mmol), $Cs_2CO_3$ (9.2 mmol), TMEDA (0.62 mmol), yield 72%. $^1$H NMR (400 MHz, $CDCl_3$): δ 8.25 (d, J=2.5 Hz, 1H), 7.79 (dd, J=8.7, 2.5 Hz, 1H), 7.35 (d, J=9.2 Hz, 2H), 7.08 (d, J=9.2 Hz, 2H), 6.85 (d, J=8.5 Hz, 1H). LC-ESI-MS: 284 [M+H].

Intermediate 3f (5-bromo-2-(3,4-difluoro-phenoxy)pyridine, $R_1$=3,4-difluoro): reagent: 2,5-dibromopyridine (6.15 mmol), 3,4-difluorophenol (6.46 mmol), CuI (0.61 mmol), $Cs_2CO_3$ (9.2 mmol), TMEDA (0.62 mmol), yield 82%, LC-ESI-MS: 286 [M+H].

Intermediate 3g (5-bromo-(2,6-difluoro-phenoxy)pyridine, $R_1$=2,6-difluoro): reagent: 2,5-dibromopyridine (6.15 mmol), 2,6-difluorophenol (6.46 mmol), CuI (0.61 mmol), $Cs_2CO_3$ (9.2 mmol), TMEDA (0.62 mmol), yield 82%, LC-ESI-MS: 286 [M+H].

Intermediate 3h (5-bromo-(2,3-difluoro-phenoxy)pyridine, $R_1$=2,3-difluoro): reagent: 2,5-dibromopyridine (6.15 mmol), 2,3-difluorophenol (6.46 mmol), CuI (0.61 mmol), $Cs_2CO_3$ (9.2 mmol), TMEDA (0.62 mmol), yield 88%, LC-ESI-MS: 286 [M+H].

Intermediate 3i (5-bromo-(4-methyl-phenoxy)pyridine, $R_1$=4-methyl): reagent: 2,5-dibromopyridine (6.15 mmol), 4-methylphenol (6.46 mmol), CuI (0.61 mmol), $Cs_2CO_3$ (9.2 mmol), TMEDA (0.62 mmol), yield 61%, LC-ESI-MS: 264 [M+H].

Intermediate 3j (5-bromo-(4-methoxy-phenoxy)pyridine, $R_1$=4-methoxy): reagent: 2,5-dibromopyridine (6.15 mmol), 4-methoxyphenol (6.46 mmol), CuI (0.61 mmol), $Cs_2CO_3$ (9.2 mmol), TMEDA (0.62 mmol), yield 59%. $^1$H NMR (400 MHz, $CDCl_3$): δ 8.22 (d, J=2.4 Hz, 1H), 7.76 (dd, J=8.4, 2.4 Hz, 1H), 6.93 (d, J=8.4 Hz, 1H), 6.75 (m, 4H), 3.68 (s, 3H). LC-ESI-MS: 280 [M+H].

Intermediate 3k (5-bromo-(4-trifluoromethyl-phenoxy)pyridine, $R_1$=4-trifluoromethyl): reagent: 2,5-dibromopyridine (6.15 mmol), 4-trifluoromethylphenol (6.46 mmol), CuI (0.61 mmol), $Cs_2CO_3$ (9.2 mmol), TMEDA (0.62 mmol), yield 66%, LC-ESI-MS: 318 [M+H].

Example 6: Preparation of Intermediates 4a-4d

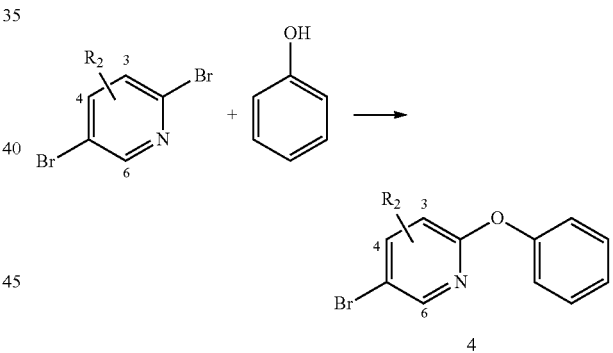

Operation steps: substituted 2,5-dibromopyridine (6.15 mmol), phenol (6.46 mmol), CuI (0.62 mmol) and $Cs_2CO_3$ (9.2 mmol) were placed in a 25 mL dried flask; 15 mL of DMSO is added; TMEDA (0.62 mmol) was then added; and the solution was heated to 110° C. in an Ar atmosphere to carry out a reaction for about 20 hours until TLC transformation was complete. After the reaction system was cooled to room temperature, a large amount of ethyl acetate was added, rinsing with water is carried out four times, extraction with ethyl acetate was carried out twice, EA phases were combined and rinsed with a saturated NaCl solution, and an organic phase was then dried, filtered and spin-dried, thus obtaining a brown oily product.

Intermediate 5-bromo-4-fluoro-2-phenoxypyridine 4a ($R_2$=4-fluoro), reagent: 2,5-dibromo-4-fluoropyridine (6.15 mmol), phenol (6.46 mmol), other reagents and dosages being the same as above, yield 78%, LC-ESI-MS: 268 [M+H].

Intermediate 5-bromo-3-fluoro-2-phenoxypyridine 4b ($R_2$=3-fluoro), reagent: 2,5-dibromo-3-fluoropyridine (6.15 mmol), phenol (6.46 mmol), other reagents and dosages being the same as above, yield 80%, LC-ESI-MS: 268 [M+H].

Intermediate 5-bromo-4-methyl-2-phenoxypyridine 4c ($R_2$=4-methyl), reagent: 2,5-dibromo-4-methylpyridine (6.15 mmol), phenol (6.46 mmol), other reagents and dosages being the same as above, yield 85%, LC-ESI-MS: 264 [M+H].

Intermediate 5-bromo-6-methyl-2-phenoxypyridine 4d ($R_2$=6-methyl), reagent: 2,5-dibromo-6-methylpyridine (6.15 mmol), phenol (6.46 mmol), other reagents and dosages being the same as above, yield 51%, LC-ESI-MS: 264 [M+H].

Example 7: Preparation of Intermediates 5a-5h

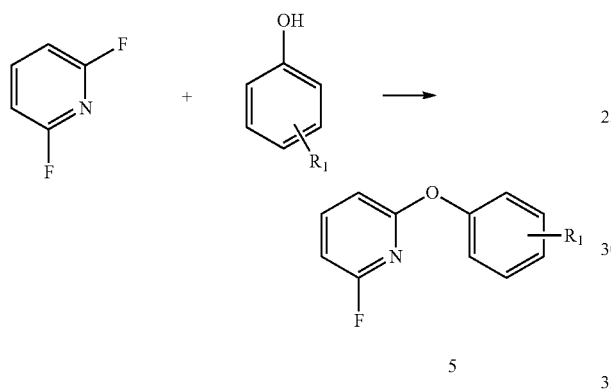

Operation steps: 2,6-difluoropyridine (6.15 mmol), substituted phenol (6.46 mmol) were placed in a 25 mL dried flask; 15 mL of DMSO was added; NaH (6.77 mmol) was then added; and the solution was heated to 30° C. in an Ar atmosphere to carry out a reaction for about 20 hours until TLC transformation was complete. After the reaction system was cooled to room temperature, a large amount of ethyl acetate was added, rinsing with water was carried out four times, extraction with ethyl acetate was carried out twice, EA phases were combined and rinsed with a saturated NaCl solution, and an organic phase was then dried, filtered and spin-dried, thus obtaining a brown oily product.

Intermediate 2-fluoro-6-phenoxypyridine 5a ($R_1$=H), reagent: 2,6-difluoro-pyridine (6.15 mmol), phenol (6.46 mmol), other reagents and dosages being the same as above, yield 65%, LC-ESI-MS: 190 [M+H].

Intermediate 2-fluoro-6-(2-fluorophenoxypyridine) 5b ($R_1$=2-fluoro), reagent: 2,6-difluoro-pyridine (6.15 mmol), 2-fluorophenol (6.46 mmol), other reagents and dosages being the same as above, yield 55%, LC-ESI-MS: 208 [M+H].

Intermediate 2-fluoro-6-(3-fluorophenoxypyridine) 5c ($R_1$=3-fluoro), reagent: 2,6-difluoro-pyridine (6.15 mmol), 3-fluorophenol (6.46 mmol), other reagents and dosages being the same as above, yield 58%, LC-ESI-MS: 208 [M+H].

Intermediate 2-fluoro-6-(4-chlorophenoxypyridine) 5d ($R_1$=4-chloro), reagent: 2,6-difluoro-pyridine (6.15 mmol), 4-chlorophenol (6.46 mmol), other reagents and dosages being the same as above, yield 62%, LC-ESI-MS: 224 [M+H].

Intermediate 2-fluoro-6-(4-methylphenoxypyridine) 5e ($R_1$=4-methyl), reagent: 2,6-difluoro-pyridine (6.15 mmol), 4-methylphenol (6.46 mmol)), other reagents and dosages being the same as above, yield 59%, LC-ESI-MS: 204 [M+H].

Intermediate 2-fluoro-6-(4-methoxyphenoxypyridine) 5f ($R_1$=4-methoxy), reagent: 2,6-difluoro-pyridine (6.15 mmol), 4-methoxyphenol (6.46 mmol)), other reagents and dosages being the same as above, yield 59%, LC-ESI-MS: 220 [M+H].

Intermediate 2-(2,6-difluorophenoxy)-6-fluoropyridine 5g ($R_1$=2,6-difluoro), reagent: 2,6-difluoro-pyridine (6.15 mmol), 2,6-difluorophenol (6.46 mmol), other reagents and dosages being the same as above, yield 50%, LC-ESI-MS: 226 [M+H].

Intermediate 2-(2,3-difluorophenoxy)-6-fluoropyridine 5h ($R_1$=2,3-difluoro), reagent: 2,6-difluoro-pyridine (6.15 mmol), 2,3-difluorophenol (6.46 mmol), other reagents and dosages being the same as above, yield 52%, LC-ESI-MS: 226 [M+H].

Example 8: Preparation of Intermediate 6

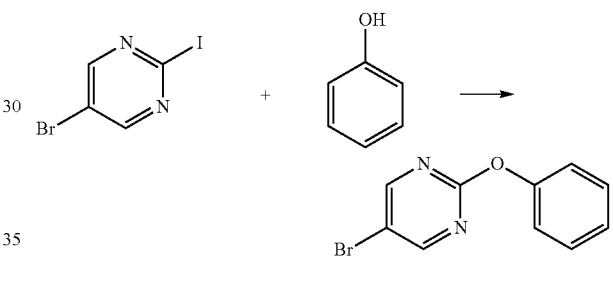

Operation steps: 5-bromo-2-iodopyrimidine (3 mmol), phenol (3.2 mmol), 2-picolinic acid (0.3 mmol), CuI (0.3 mmol), potassium phosphate (4.5 mmol) were placed in a 25 mL dried flask; 15 mL of DMSO was added; and the solution was heated to 110° C. in an Ar atmosphere to carry out a reaction for about 20 hours until TLC transformation was complete. After the reaction system was cooled to room temperature, a large amount of ethyl acetate was added, rinsing with water was carried out four times, extraction with ethyl acetate was carried out twice, EA phases were combined and rinsed with a saturated NaCl solution; an organic phase was then dried, filtered and spin-dried; and purification was carried out by silica gel column chromatograph, thus obtaining 1.1g of a white product, with a yield of 87%. $^1$H NMR (400 MHz, CDCl$_3$): δ 8.56 (s, 2H), 7.48-7.39 (m, 2H), 7.31-7.25 (m, 1H), 7.22-7.14 (m, 2H). LC-ESI-MS: 251 [M+H].

Example 9: Preparation of Intermediate 7

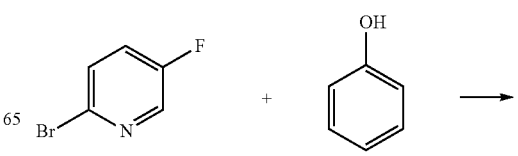

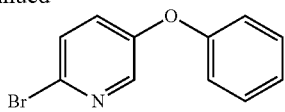

Operation steps: In an Ar atmosphere, 15 mL of DMF solution was placed in an ice water bath, and sodium hydride (5.1 mmol) and phenol (4.6 mmol) were carefully added. The solution was then stirred at room temperature for about 1 hour, and 2-bromo-5-fluoropyridine (4.6 mmol) was then added and the reaction was further performed at room temperature overnight. After completion of the TLC reaction, the reaction was quenched with an aqueous solution of ammonium chloride and extraction with ethyl acetate was carried out three times. The organic phases were combined and dried over anhydrous sodium sulfate, and then filtering and reduced-pressure concentration were carried out to obtain an oily product which was directly used in the next step. LC-ESI-MS: 250 [M+H].

Example 10: Preparation of Key Intermediate 8

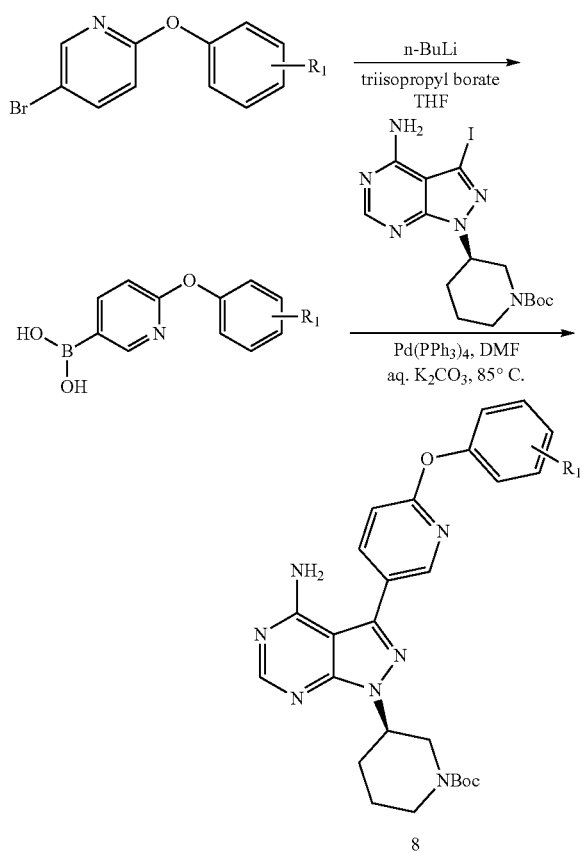

Operation Steps:
Step 1: Corresponding compounds 3a-3k were dissolved in dried THF and cooled to −78° C. in an Ar atmosphere, and then n-butyllithiumwasgradually added dropwise. The reaction system was further continued for 1 hour at this temperature while stirring, and then triisopropyl borate was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product of the previous step was added to 70 mL of DMF which had just been bubbled with Ar, the Compound 1a and tetrakis (triphenylphosphine) palladium were stirred in an Ar atmosphere, and then 2N aq. $K_2CO_3$ aqueous solution was added. The reaction system was heated to 85° C. in an Ar atmosphere for keeping reaction overnight until the reaction was complete under the tracking of TLC. The reaction system was cooled to room temperature, filtering was carried out with kieselguhr, and rinsing with ethyl acetate was carried out for several times. Rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent.

Chemical Reagents and Data Characterization:
Intermediate 8a ($R_1$=H), reagent: Compound 3a (30 mmol), n-butyllithium (33.3 mmol), triisopropyl borate (39.4 mmol), Compound 1a (17.3 mmol), tetrakis(triphenylphosphine)palladium (0.78 mmol), 2N aq. $K_2CO_3$ (26 mL); product: white solid, yield: 60% (two steps), $^1$H NMR (400 MHz, CDCl$_3$): δ 8.51 (d, J=2.1 Hz, 1H), 8.37 (s, 1H), 8.04 (dd, J=8.5, 2.4 Hz, 1H), 7.44 (t, J=7.9 Hz, 2H), 7.29-7.22 (m, 1H), 7.19 (d, J=7.7 Hz, 2H), 7.08 (d, J=8.5 Hz, 1H), 5.75 (brs, 2H), 4.91-4.82 (m, 1H), 4.25 (brs, 1H), 4.12 (dd, J=14.2, 7.0 Hz, 1H), 3.43 (brs, 1H), 2.87 (dd, J=13.0, 10.0 Hz, 1H), 2.33-2.10 (m, 2H), 1.90 (brs, 1H), 1.76-1.66 (m, 1H), 1.44 (s, 9H). LC-ESI-MS: 488 [M+H].

Intermediate 8b ($R_1$=4-fluoro), reagent: Compound 3b (3 mmol), n-butyllithium (3.33 mmol), triisopropyl borate (3.94 mmol), Compound 1a (1.73 mmol), tetrakis(triphenylphosphine)palladium (0.078 mmol), 2N aq. $K_2CO_3$ (2.6 mL); product: white solid, yield: 45% (two steps), LC-ESI-MS: 506 [M+H].

Intermediate 8c ($R_1$=3-fluoro), reagent: Compound 3c (3 mmol), n-butyllithium (3.33 mmol), triisopropyl borate (3.94 mmol), Compound 1a (1.73 mmol), tetrakis(triphenylphosphine)palladium (0.078 mmol), 2N aq. $K_2CO_3$ (2.6 mL); product: white solid, yield: 42% (two steps), LC-ESI-MS: 506 [M+H].

Intermediate 8d ($R_1$=2-fluoro), reagent: Compound 3d (3 mmol), n-butyllithium (3.33 mmol), triisopropyl borate (3.94 mmol), Compound 1a (1.73 mmol), tetrakis(triphenylphosphine)palladium (0.078 mmol), 2N aq. $K_2CO_3$ (2.6 mL); product: white solid, yield: 52% (two steps), LC-ESI-MS: 506 [M+H].

Intermediate 8e ($R_1$=4-chloro), reagent: Compound 3e (3 mmol), n-butyllithium (3.33 mmol), triisopropyl borate (3.94 mmol), Compound 1a (1.73 mmol), tetrakis(triphenylphosphine)palladium (0.078 mmol), 2N aq. $K_2CO_3$ (2.6 mL); product: white solid, yield: 41% (two steps), LC-ESI-MS: 522 [M+H].

Intermediate 8e ($R_1$=3,4-difluoro), reagent: Compound 3f (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 26% (two steps), LC-ESI-MS: 524 [M+H].

Intermediate 8g (R$_1$=2,6-difluoro), reagent: Step 1, Compound 3g (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 36% (two steps), LC-ESI-MS: 524 [M+H].

Intermediate 8h (R$_1$=2,3-difluoro), reagent: Step 1, Compound 3h (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 24% (two steps), LC-ESI-MS: 524 [M+H].

Intermediate 8i (R$_1$=4-methyl), reagent: Compound 3i (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 57% (two steps), $^1$H NMR (400 MHz, CDCl$_3$): δ8.48 (d, J=2.3 Hz, 1H), 8.33 (s, 1H), 8.02 (dd, J=8.5, 2.3 Hz, 1H), 7.15-7.03 (m, 3H), 6.96-6.90 (m, 2H), 5.71 (brs, 2H), 4.92-4.80 (m, 1H), 4.19 (brs, 1H), 4.08 (dd, J=13.9, 6.9 Hz, 1H), 3.41 (brs, 1H), 2.90-2.81 (m, 1H), 2.32-2.11 (m, 2H), 2.27 (s, 3H), 1.88 (brs, 1H), 1.77-1.65 (m, 1H), 1.45 (s, 9H). LC-ESI-MS: 502 [M+H].

Intermediate 8j (R$_1$=4-methoxy), reagent: Compound 3j (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 38% (two steps), LC-ESI-MS: 518 [M+H].

Intermediate 8k (R$_1$=4-trifluoromethyl), reagent: Step 1, Compound 3k (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 35% (two steps), LC-ESI-MS: 556 [M+H].

Example 11: Preparation of Intermediate 9

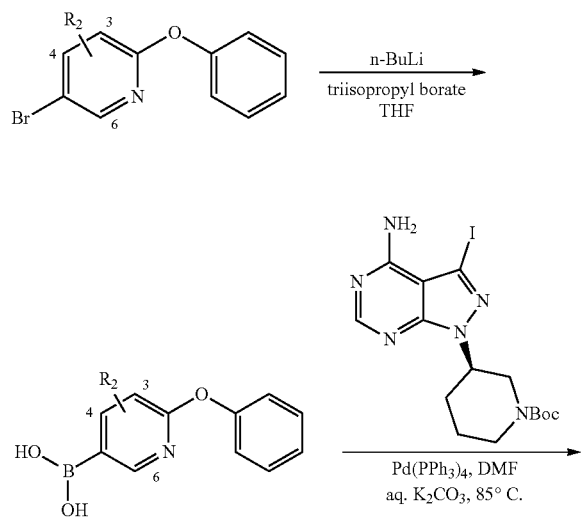

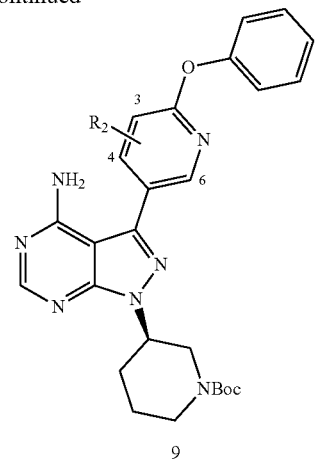

Operation Steps:

Step 1: Corresponding compounds 4a-4d were dissolved in 15 mL of dried THF and cooled to −78° C. in an Ar atmosphere, and then n-butyllithium was gradually added dropwise. The reaction system was further continued for 1 hour at this temperature while stirring, and then triisopropyl borate was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product of the previous step was added to 7 mL of DMF which had just been bubbled with Ar, the Compound 1a and tetrakis(triphenylphosphine)palladium were stirred in an Ar atmosphere, and then 2N aq. K$_2$CO$_3$ aqueous solution was added. The reaction system was heated to 85° C. in an Ar atmosphere for keeping reaction overnight until the reaction was complete under the tracking of TLC. The reaction system was cooled to room temperature, filtering was carried out with kieselguhr, and rinsing with EA was carried out for several times. Extraction with EA was then carried out, rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent.

Chemical Reagents and Data Characterization:

Intermediate 9a (R$_2$=4-fluoro), reagent: Compound 4a (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 33% (two steps), LC-ESI-MS: 506 [M+H].

Intermediate 9b (R$_2$=3-fluoro), reagent: Compound 4b (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 52% (two steps), LC-ESI-MS: 506 [M+H].

Intermediate 9c (R$_2$=4-methyl), reagent: Compound 4c (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 45% (two steps), LC-ESI-MS: 502 [M+H].

Intermediate 9d (R$_2$=6-methyl), reagent: Compound 4d (3 mmol), n-butyllithium (3.33 mmol), triisopropyl borate (3.94 mmol), Compound 1a (1.73 mmol), tetratrikis(phenylphosphine)palladium (0.078 mmol), 2N aq. K$_2$CO$_3$ (2.6 mL); product: white solid, yield: 66% (two steps), LC-ESI-MS: 502 [M+H].

Example 12: Preparation of Intermediates 10a and 10c-i

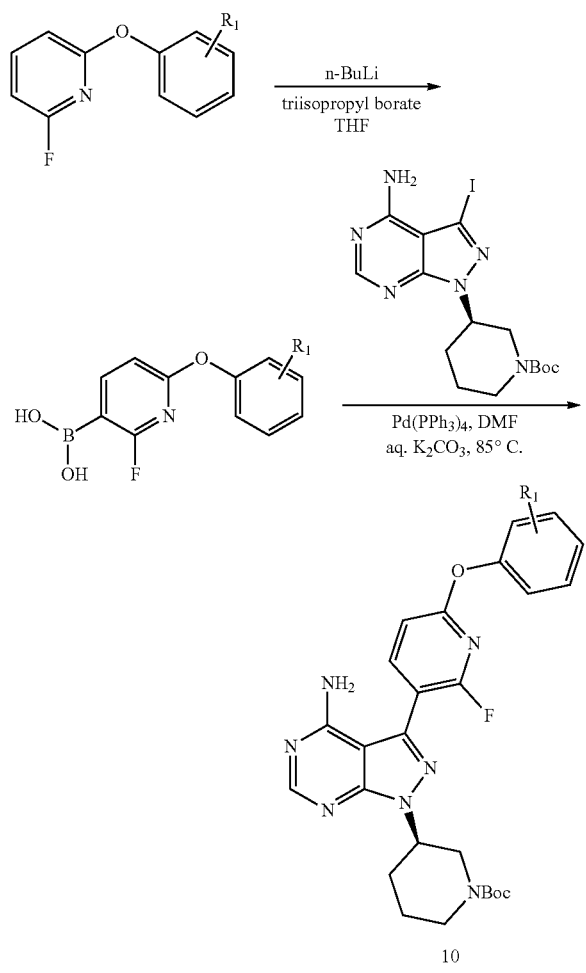

Operation Steps:

Step 1: Corresponding compounds in Compounds 5a-5h were dissolved in dried THF and cooled to −78° C. in an Ar atmosphere, and then n-butyllithium was gradually added dropwise. The reaction system was further continued for 1 hour at this temperature while stirring, and then triisopropyl borate was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product of the previous step was added to 70 mL of DMF which had just been bubbled with Ar, the Compound 1a and tetrakis(triphenylphosphine)palladium were stirred in an Ar atmosphere, and then 2N aq. K$_2$CO$_3$ aqueous solution was added. The reaction system was heated to 85° C. in an Ar atmosphere for keeping reaction overnight until the reaction was complete under the tracking of TLC. The reaction system was cooled to room temperature, filtering was carried out with kieselguhr, and rinsing with ethyl acetate was carried out for several times. Rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent, thus obtaining a white solid product.

Intermediate 10a (R$_1$=H), reagent: Compound 5a (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 30% (two steps), LC-ESI-MS: 506 [M+H].

Intermediate 10c (R$_1$=2-fluoro), reagent: Compound 5b (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 25% (two steps), LC-ESI-MS: 524 [M+H].

Intermediate 10d (R$_1$=3-fluoro), reagent: Compound 5c (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 28% (two steps), LC-ESI-MS: 524 [M+H].

Intermediate 10e (R$_1$=4-chloro), reagent: Compound 5d (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 21% (two steps), LC-ESI-MS: 541 [M+H].

Intermediate 10f (R$_1$=4-methyl), reagent: Compound 5e (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 20% (two steps), LC-ESI-MS: 520 [M+H].

Intermediate 10g (R$_1$=4-methoxy), reagent: Compound 5f (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 18% (two steps), LC-ESI-MS: 536 [M+H].

Intermediate 10h (R$_1$=2,6-difluoro), reagent: Compound 5g (3 mmol), n-butyllithium (3.33 mmol), triisopropyl borate (3.94 mmol), Compound 1a (1.73 mmol), tetrakis(triphenylphosphine)palladium (0.078 mmol), 2N aq. K$_2$CO$_3$ (2.6 mL); product: white solid, yield: 20% (two steps), LC-ESI-MS: 542 [M+H].

Intermediate 10i (R$_1$=2,3-difluoro), reagent: Compound 5h (3 mmol), n-butyllithium (3.33 mmol), triisopropyl borate (3.94 mmol), Compound 1a (1.73 mmol), tetrakis (triphenylphosphinepalladium (0.078 mmol), 2N aq. $K_2CO_3$ (2.6 mL); product: white solid, yield: 21% (two steps), LC-ESI-MS: 542 [M+H].

Example 13: Preparation of Intermediate 10b

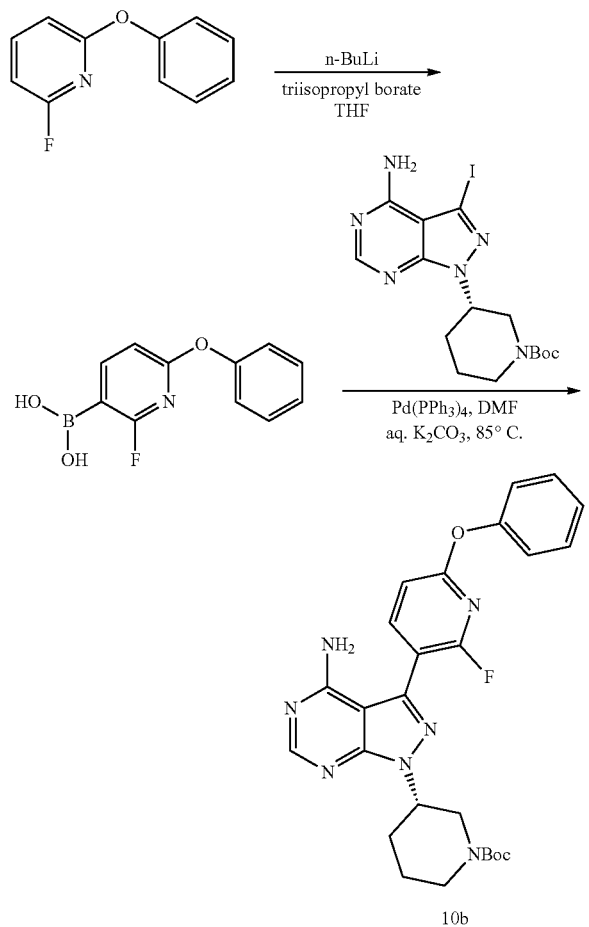

Operation Steps:

Step 1: The Compound 5a (3 mmol) was dissolved in dried THF and cooled to −78° C. in an Ar atmosphere, and then n-butyllithium (3 mmol) was gradually added dropwise. The reaction system was further continued for 1 hour at this temperature while stirring, and then triisopropyl borate (3.94 mmol) was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product of the previous step was added to 70 mL of DMF which had just been bubbled with Ar, the Compound 1b (1.73 mmol) and tetrakis(triphenylphosphine)palladium (0.078 mmol) were stirred in an Ar atmosphere, and then 2N aq. $K_2CO_3$ aqueous solution (2.6 mL) was added. The reaction system was heated to 85° C. in an Ar atmosphere for keeping reaction overnight until the reaction was complete under the tracking of TLC. The reaction system was cooled to room temperature, filtering was carried out with kieselguhr, and rinsing with ethyl acetate was carried out for several times. Rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent, thus obtaining a white solid product 10b ($R_1$=H), with a yield of 28% (two steps), LC-ESI-MS: 506 [M+H].

Example 14: Preparation of Intermediate 11

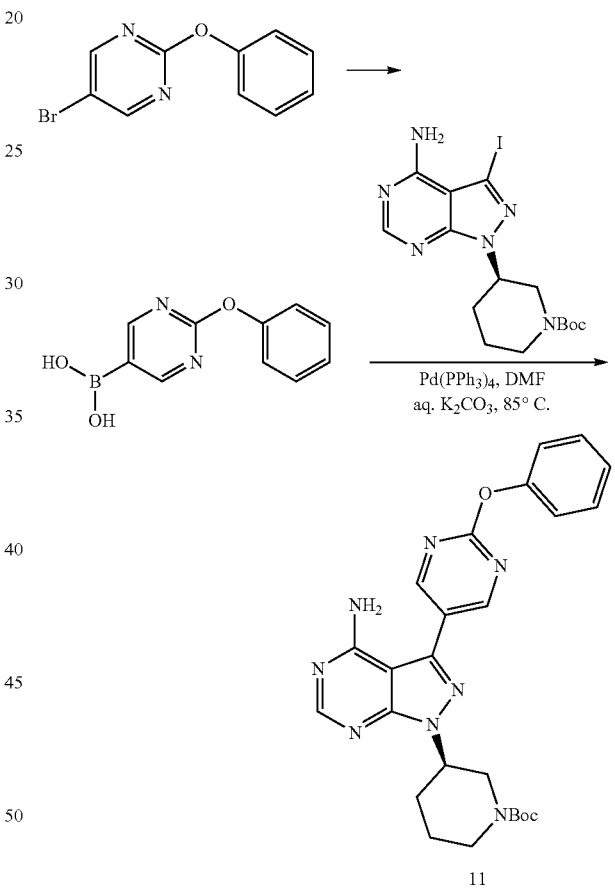

Operation Steps:

Step 1: The Compound 6 (3 mmol) was dissolved in 15 mL of dried THF and cooled to −78° C. in an Ar atmosphere, and then n-butyllithium (1.3 mL, 3.3 mmol, 2.5M in THF) was gradually added dropwise.

The reaction system was further continued for 1 hour at this temperature while stirring, and then triisopropyl borate (0.74 g, 3.94 mmol) was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product (2.3 mmol) of the previous step was added to 7 mL of DMF which had just been bubbled with Ar, the Compound 1a (1.73 mmol) and tetrakis (triphenylphosphine)palladium (0.078 mmol) were stirred in an Ar atmosphere, and then 2.6 mL of 2N aq. $K_2CO_3$ aqueous solution was added. The reaction system was heated to 85° C. in an Ar atmosphere for keeping reaction overnight until the reaction was complete under the tracking of TLC.

The reaction system was cooled to room temperature, filtering was carried out with kieselguhr, and rinsing with EA was carried out for several times. Extraction was then carried out with EA, rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent, thus obtaining a white solid product 11, with a yield of 25%, $^1$H NMR (400 MHz, $CDCl_3$): δ 8.90 (s, 2H), 8.38 (s, 1H), 7.46 (dd, J=10.8, 5.1 Hz, 2H), 7.29 (dd, J=10.1, 4.7 Hz, 1H), 7.26-7.18 (m, 2H), 5.91 (brs, 2H), 4.94-4.77 (m, 1H), 4.29 (brs, 1H), 4.18-4.04 (m, 1H), 3.53-3.22 (m, 1H), 2.88 (t, J=11.7 Hz, 1H), 2.33-2.13 (m, 2H), 1.97-1.84 (m, 1H), 1.77-1.64 (m, 1H), 1.44 (s, 9H). LC-ESI-MS: 489 [M+H].

Example 15 Preparation of Intermediate 12

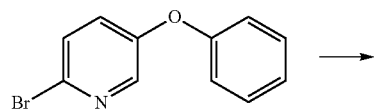

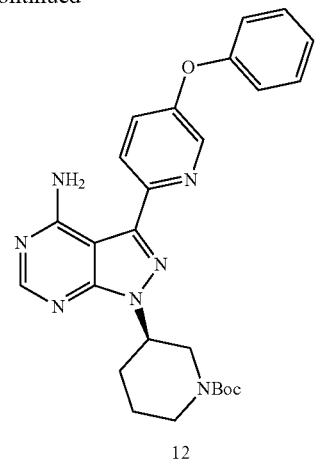

12

Operation Steps:

Step 1: The Compound 7 (3 mmol) was dissolved in 15 mL of dried THF and cooled to −78° C. in an Ar atmosphere, and then n-butyllithium (1.3 mL, 3.3 mmol, 2.5M in THF) was gradually added dropwise.

The reaction system was further continued for 1 hour at this temperature while stirring, and then triisopropyl borate (0.74 g, 3.94 mmol) was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product (1.5 mmol) of the previous step was added to 5 mL of DMF which had just been bubbled with Ar, the Compound 1a (1.1 mmol) and tetrakis (triphenylphosphine)palladium (0.06 mmol) were stirred in an Ar atmosphere, and then 1.5 mL of 2N aq. $K_2CO_3$ aqueous solution was added. The reaction system was heated to 85° C. in an Ar atmosphere for keeping reaction overnight until the reaction was complete under the tracking of TLC. The reaction system was cooled to room temperature, filtering was carried out with kieselguhr, and rinsing with EA was carried out for several times. Extraction with EA was then carried out, rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent, thus obtaining a white solid product 12, with a yield of 15%, LC-ESI-MS: 488 [M+H].

Example 16: Preparation of Intermediates 13a-13d

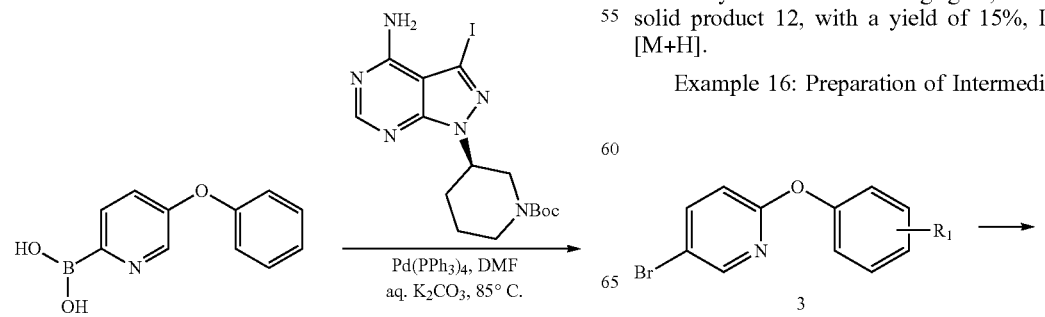

3

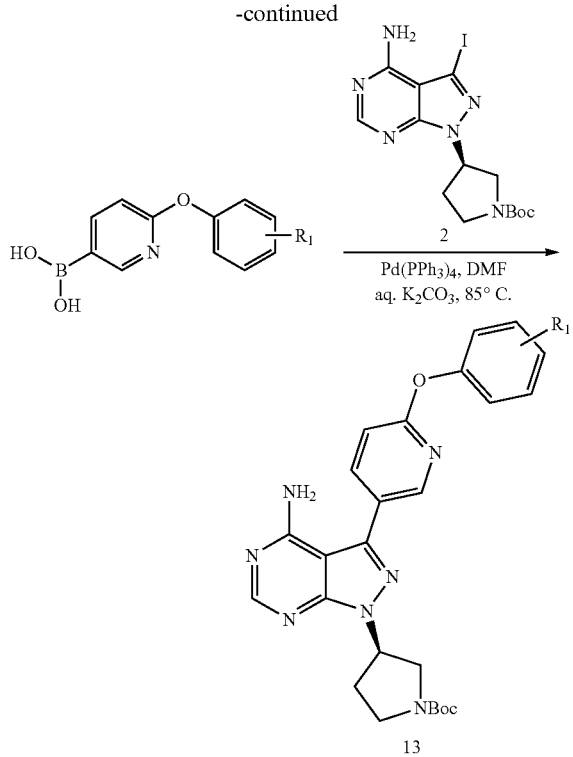

Chemical Reagents and Data Characterization:

Intermediate 13a ($R_1$=H), reagent: Compound 3a (3 mmol), n-butyllithium (3.33 mmol), triisopropyl borate (3.94 mmol), Compound 2a (3 mmol), tetrakis(triphenylphosphine)palladium (0.15 mmol), 2N aq. $K_2CO_3$ (4.5 mL); product: white solid, yield: 40% (two steps), LC-ESI-MS: 474 [M+H].

Intermediate 13b ($R_1$=2-fluoro), reagent: Compound 3d (3 mmol), n-butyllithium (3.33 mmol), triisopropyl borate (3.94 mmol), Compound 2a (3 mmol), tetrakis(triphenylphosphine)palladium (0.15 mmol), 2N aq. $K_2CO_3$ (4.5 mL); product: white solid, yield: 52% (two steps), LC-ESI-MS: 492 [M+H].

Intermediate 13c ($R_1$=2,6-difluoro), reagent: Compound 3g (3 mmol), n-butyllithium (3.33 mmol), triisopropyl borate (3.94 mmol), Compound 2a (3 mmol), tetrakis(triphenylphosphine)palladium (0.15 mmol), 2N aq. $K_2CO_3$ (4.5 mL); product: white solid, yield: 43% (two steps), LC-ESI-MS: 510 [M+H].

Intermediate 13d ($R_1$=2,3-difluoro), reagent: Compound 3h (3 mmol), n-butyllithium (3.33 mmol), triisopropyl borate (3.94 mmol), Compound 2a (3 mmol), tetrakis(triphenylphosphine)palladium (0.15 mmol), 2N aq. $K_2CO_3$ (4.5 mL); product: white solid, yield: 48% (two steps), LC-ESI-MS: 510 [M+H].

Example 17: Preparation of Intermediate 13e

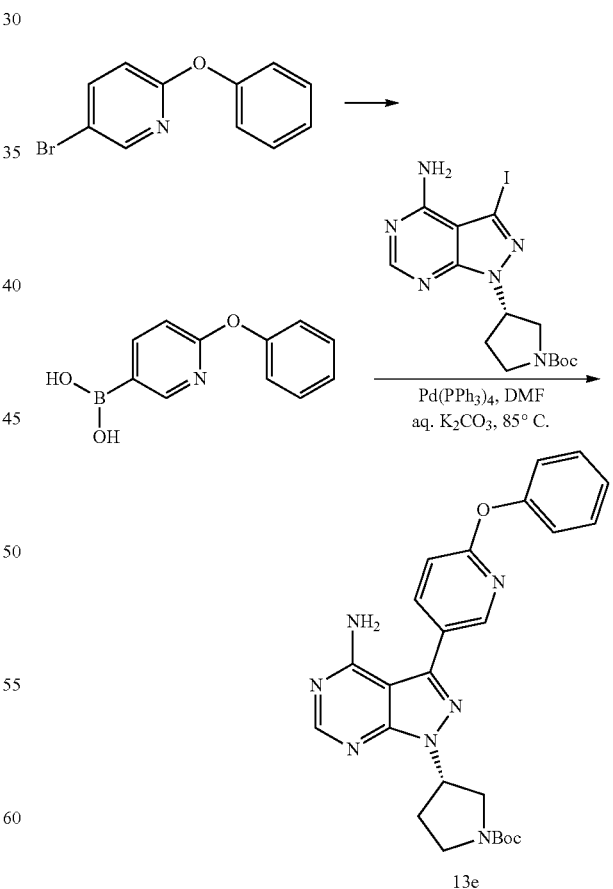

Operation Steps:

Step 1: The Compound 3a, the Compound 3d, the Compound 3g or the Compound 3h (3 mmol) was dissolved in 15 mL of dried THF and cooled to −78° C. in an Ar atmosphere, and then n-butyllithium (1.3 mL, 3.3 mmol, 2.5M in THF) was gradually added dropwise. The reaction system was further continued for 1 hour at this temperature while stirring, and then triisopropyl borate (0.74 g, 3.94 mmol) was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product (4.2 mmol) of the previous step was added to 15 mL of DMF which had just been bubbled with Ar, the Compound 2a (3 mmol) and tetrakis(triphenylphosphine)palladium (0.15 mmol) were stirred in an Ar atmosphere, and then 4.5 mL of 2N aq. $K_2CO_3$ aqueous solution was added. The reaction system was heated to 85° C. in an Ar atmosphere for keeping reaction overnight until the reaction was complete under the tracking of TLC. The reaction system was cooled to room temperature, filtering was carried out with kieselguhr, and rinsing with EA was carried out for several times. Extraction with EA was then carried out, rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent, thus obtaining a white solid product.

Operation Steps:

Step 1: The Compound 3a (3 mmol) was dissolved in 15 mL of dried THF and cooled to −78° C. in an Ar atmosphere, and then n-butyllithium (1.3 mL, 3.3 mmol, 2.5M in THF) was gradually added dropwise. The reaction system was further continued for 1 hour at this temperature while stirring, and then triisopropyl borate (0.74 g, 3.94 mmol) was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product (4.2 mmol) of the previous step was added to 15 mL of DMF which had just been bubbled with Ar, the Compound 2b (3 mmol) and tetrakis (triphenylphosphine)palladium (0.15 mmol) were stirred in an Ar atmosphere, and then 4.5 mL of 2N aq. $K_2CO_3$ aqueous solution was added. The reaction system was heated to 85° C. in an Ar atmosphere for keeping reaction overnight until the reaction was complete under the tracking of TLC. The reaction system was cooled to room temperature, filtering was carried out with kieselguhr, and rinsing with EA was carried out for several times. Extraction with EA was then carried out, rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent, thus obtaining a white solid product 13e, with a yield of 39% (two steps), LC-ESI-MS: 474 [M+H].

Example 18: Preparation of Intermediates 14a and 14c-14e

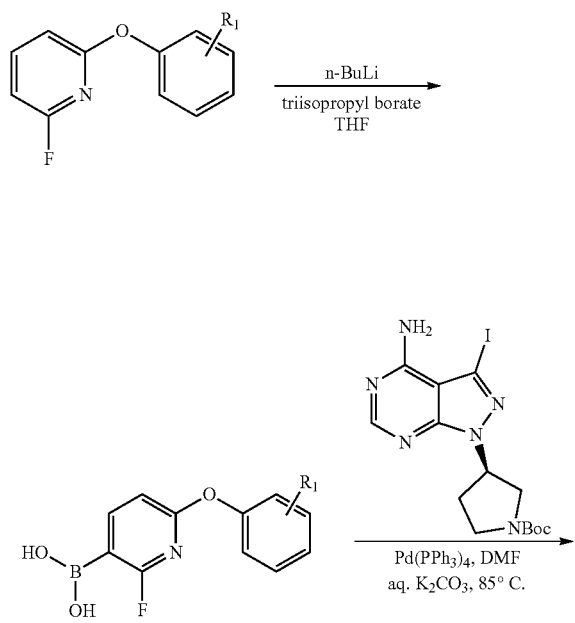

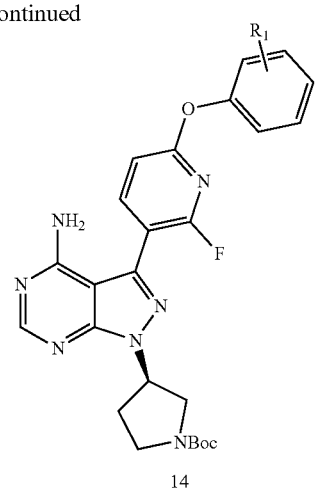

14

Operation Steps:

Step 1: The Compound 5a, the Compound 5b, the Compound 5g or the Compound 5h was dissolved in dried THF and cooled to −78° C. in an Ar atmosphere, and then n-butyllithium was gradually added dropwise. The reaction system was further continued for 1 hour at this temperature while stirring, and then triisopropyl borate was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product of the previous step was added to 70 mL of DMF which had just been bubbled with Ar, the Compound 2a and tetrakis(triphenylphosphine)palladium were stirred in an Ar atmosphere, and then 2N aq. $K_2CO_3$ aqueous solution was added. The reaction system was heated to 85° C. in an Ar atmosphere for keeping reaction overnight until the reaction was complete under the tracking of TLC. The reaction system was cooled to room temperature, filtering was carried out with kieselguhr, and rinsing with ethyl acetate was carried out for several times. Rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent, thus obtaining a white solid product.

Chemical Reagents and Data Characterization:

Intermediate 14a ($R_1$=H): reagent: Compound 5a (3 mmol), n-butyllithium (3.33 mmol), triisopropyl borate (3.94 mmol), Compound 2a (3 mmol), tetrakis(triphenylphosphine)palladium (0.15 mmol), 2N aq. $K_2CO_3$ (4.5 mL); product: white solid, yield: 24% (two steps), LC-ESI-MS: 492 [M+H].

Intermediate 14c ($R_1$=2-fluoro): reagent: Compound 5b (3 mmol), n-butyllithium (3.33 mmol), triisopropyl borate (3.94 mmol), Compound 2a (3 mmol), tetrakis(triphenylphosphine)palladium (0.15 mmol), 2N aq. $K_2CO_3$ (4.5 mL); product: white solid, yield: 21% (two steps), LC-ESI-MS: 510 [M+H].

Intermediate 14d (R$_1$=2,6-difluoro): reagent: Compound 5g (3 mmol), n-butyllithium (3.33 mmol), triisopropyl borate (3.94 mmol), Compound 2a (3 mmol), tetrakis(triphenylphosphine)palladium (0.15 mmol), 2N aq. K$_2$CO$_3$ (4.5 mL); product: white solid, yield: 19% (two steps), LC-ESI-MS: 528 [M+H].

Intermediate 14e (R$_1$=2,3-difluoro), reagent: Compound 5h (3 mmol), n-butyllithium (3.33 mmol), triisopropyl borate (3.94 mmol), Compound 2a (3 mmol), tetrakis(triphenylphosphine)palladium (0.15 mmol), 2N aq. K$_2$CO$_3$ (4.5 mL); product: white solid, yield: 19% (two steps), LC-ESI-MS: 528 [M+H].

Example 19: Preparation of Intermediate 14b

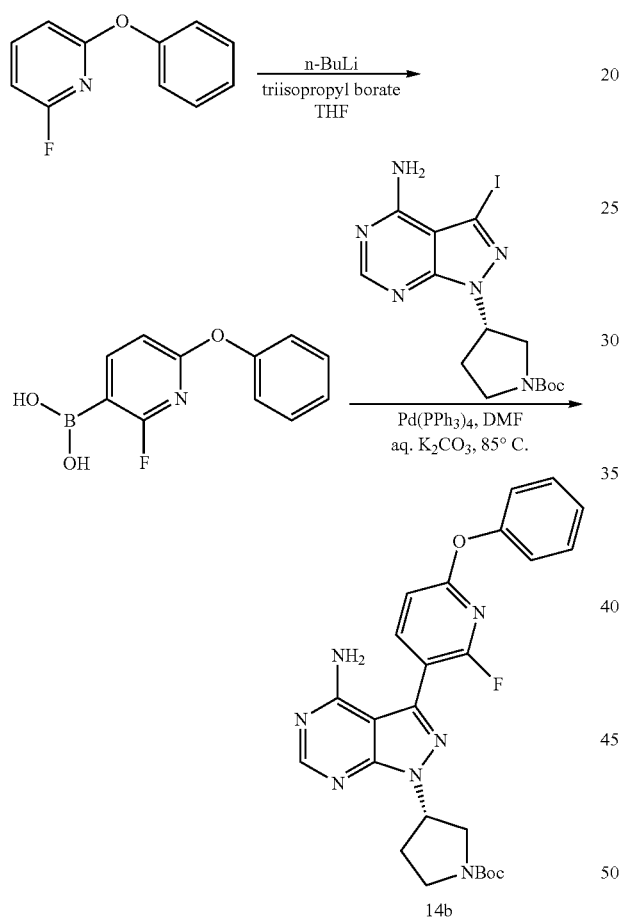

14b

Operation Steps:

Step 1: The Compound 5a (3 mmol) was dissolved in dried THF and cooled to −78° C. in an Ar atmosphere, and then n-butyllithium (3 mmol) was gradually added dropwise. The reaction system was further continued for 1 hour at this temperature while stirring, and then triisopropyl borate (3.94 mmol) was added. Then, the reaction was carried out at −78° C. for 1 hour, then the reaction system was slowly increased to room temperature, and the reaction was quenched with an aqueous solution of ammonium chloride. Extraction with ethyl acetate was carried out three times, the organic phases were combined, rinsed with water and a saturated NaCl solution and then dried over anhydrous sodium sulfate, and then filtering and reduced-pressure concentration were carried out. Recrystallization was carried out with ethyl acetate and petroleum ether, thus obtaining a white solid boric acid product which was directly used in the next step.

Step 2: The boric acid product of the previous step was added to 70 mL of DMF which had just been bubbled with Ar, the Compound 2b (3 mmol) and tetrakis(triphenylphosphine)palladium (0.15 mmol) were stirred in an Ar atmosphere, and then 2N aq. K$_2$CO$_3$ aqueous solution (4.5 mL) was added. The reaction system was heated to 85° C. in an Ar atmosphere for keeping reaction overnight until the reaction was complete under the tracking of TLC. The reaction system was cooled to room temperature, filtering was carried out with kieselguhr, and rinsing with ethyl acetate was carried out for several times. Rinsing with water was carried out three times, and then rinsing with a saturated NaCl solution was carried out; then, drying, filtering, and reduced-pressure concentration were carried out; and purification was carried out by silica gel column chromatograph with petroleum ether-ethyl acetate as an eluting agent, thus obtaining a white solid product 14b, with a yield of 22% (two steps), LC-ESI-MS: 492 [M+H].

Example 20: Preparation of Target Compounds 15a-15k

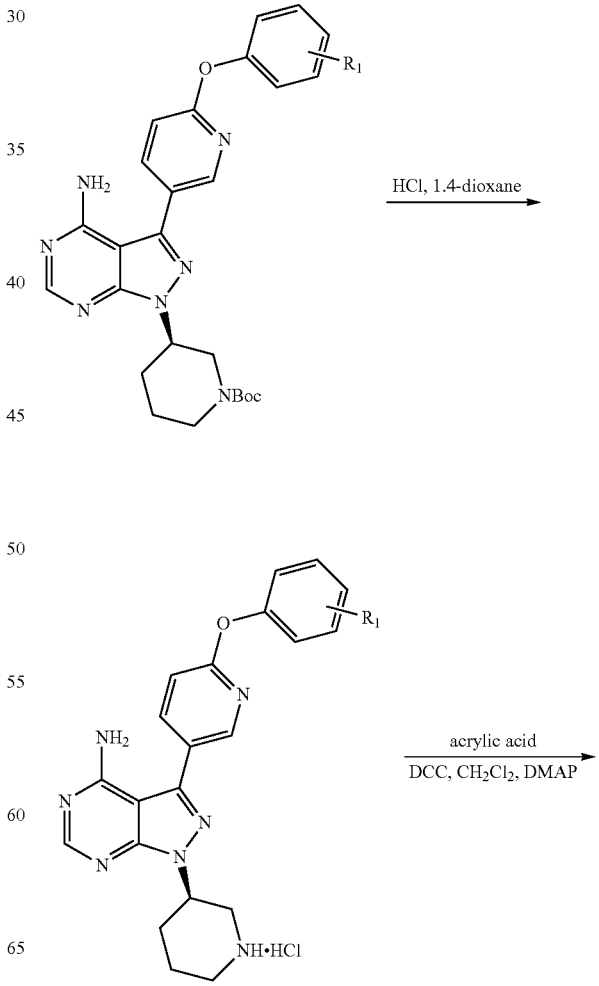

-continued

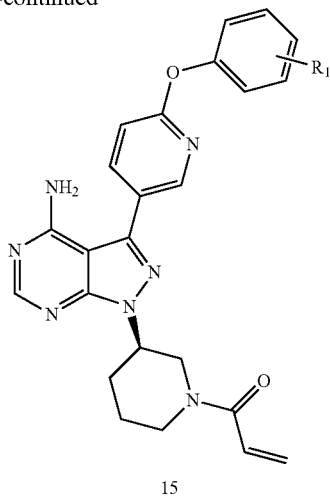

15

Operation Steps:

1) Corresponding compounds in Compounds 8a-8k (1.3 mmol) were dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a target compound.

Chemical Reagents and Data Characterization:

Target compound 15a ($R_1$=H): reagent: Compound 8a (1.33 mmol), acrylic acid (1.3 mmol), DCC (1.3 mmol), DMAP (0.065 mmol); product: white solid, yield: 60% (two steps). $^1$H NMR (500 MHz, $CDCl_3$): δ 8.50 (d, J=2.3 Hz, 1H), 8.36 (d, J=11.2 Hz, 1H), 8.03 (dd, J=8.5, 2.2 Hz, 1H), 7.44 (t, J=7.9 Hz, 2H), 7.24 (d, J=7.4 Hz, 1H), 7.21-7.15 (m, 2H), 7.08 (d, J=8.4 Hz, 1H), 6.68-6.48 (m, 1H), 6.28 (t, J=15.9 Hz, 1H), 5.90-5.70 (brs, 2H), 5.68 (dd, J=36.6, 10.3 Hz, 1H), 4.93-4.82 (m, 1.5H), 4.56 (d, J=12.7 Hz, 0.5H), 4.18 (d, J=12.4 Hz, 0.5H), 4.03 (d, J=13.4 Hz, 0.5H), 3.75 (t, J=11.6 Hz, 0.5H), 3.38 (t, J=11.3 Hz, 0.5H), 3.20 (t, J=12.2 Hz, 0.5H), 2.93 (t, J=11.6 Hz, 0.5H), 2.45-2.28 (m, 1H), 2.27-2.22 (m, 1H), 2.04-1.96 (m, 1H), 1.78-1.66 (m, 1H). LC-ESI-MS: 442 [M+H].

Target compound 15b ($R_1$=4-fluoro): reagent: Compound 8b (1.3 mmol), acrylic acid (1.3 mmol), DCC (1.3 mmol), DMAP (0.065 mmol); product: white solid, yield: 52% (two steps). LC-ESI-MS: 460-[M+H].

Target compound 15c ($R_1$=3-fluoro): reagent: Compound 8c (1.3 mmol), acrylic acid (1.3 mmol), DCC (1.3 mmol), DMAP (0.065 mmol); product: white solid, yield: 63% (two steps). LC-ESI-MS: 460 [M+H].

Target compound 15d ($R_1$=2-fluoro): reagent: Compound 8d (1.3 mmol), acrylic acid (1.3 mmol), DCC (1.3 mmol), DMAP (0.065 mmol); product: white solid, yield: 49% (two steps). $^1$H NMR (500 MHz, $CDCl_3$) δ 8.44 (d, J=2.2 Hz, 1H), 8.37 (s, 1H), 8.05 (d, J=8.4 Hz, 1H), 7.37-7.12 (m, 5H), 6.64-6.51 (m, 1H), 6.35-6.23 (m, 1H), 6.03-5.79 (brs, 2H), 5.75-5.63 (m, 1H), 4.94-4.78 (m, 1H, 0.5H), 4.59-4.50 (m, 0.5H), 4.23-4.14 (m, 0.5H), 4.08-3.98 (m, 0.5H), 3.78-3.68 (m, 0.5H), 3.43-3.34 (m, 0.5H), 3.27-3.15 (m, 0.5H), 2.97-2.88 (m, 0.5H), 2.43-2.22 (m, 2H), 2.05-1.97 (m, 1H), 1.79-1.68 (m, 1H). LC-ESI-MS: 460 [M+H].

Target compound 15e ($R_1$=4-fluoro): reagent: Compound 8e (1.3 mmol), acrylic acid (1.3 mmol), DCC (1.3 mmol), DMAP (0.065 mmol); product: white solid, yield: 41% (two steps). LC-ESI-MS: 476 [M+H].

Target compound 15f ($R_1$=3,4-difluoro): reagent: Compound 8f (1.3 mmol), acrylic acid (1.3 mmol), DCC (1.3 mmol), DMAP (0.065 mmol); product: white solid, yield: 60% (two steps). LC-ESI-MS: 478 [M+H].

Target compound 15g ($R_1$=2,6-difluoro): reagent: Compound 8g (1.3 mmol), acrylic acid (1.3 mmol), DCC (1.3 mmol), DMAP (0.065 mmol); product: white solid, yield: 39% (two steps). $^1$H NMR (500 MHz, $CDCl_3$) δ 8.42 (d, J=1.5 Hz, 1H), 8.33 (d, J=13.2 Hz, 1H), 8.08 (d, J=8.2 Hz, 1H), 7.32-7.24 (m, 1H), 7.20 (dd, J=13.0, 7.0 Hz, 1H), 7.04 (t, J=8.0 Hz, 2H), 6.67-6.48 (m, 1H), 6.35-6.22 (m, 1H), 6.16-5.87 (m, 3H), 4.98-4.71 (m, 1H, 0.5H), 4.62-4.51 (m, 0.5H), 4.22-4.13 (m, 0.5H), 4.08-3.96 (m, 0.5H), 3.78-3.64 (m, 0.5H), 3.39-3.31 (m, 0.5H), 3.23-3.13 (m, 0.5H), 2.96-2.86 (m, 0.5H), 2.42-2.19 (m, 2H), 2.05-1.96 (m, 1H), 1.80-1.65 (m, 1H). LC-ESI-MS: 478 [M+H].

Target compound 15h ($R_1$=2,3-difluoro): reagent: Compound 8h (1.3 mmol), acrylic acid (1.3 mmol), DCC (1.3 mmol), DMAP (0.065 mmol); product: white solid, yield: 40% (two steps). $^1$H NMR (500 MHz, $CDCl_3$) δ 8.36 (d, J=2.0 Hz, 1H), 8.29 (s, 1H), 8.01 (d, J=8.5 Hz, 1H), 7.11-7.02 (m, 2H), 7.02-6.96 (m, 1H), 6.58-6.43 (m, 1H), 6.27-6.17 (brs, 2H), 5.66-5.53 (m, 1H), 4.88-4.71 (m, 1H, 0.5H), 4.55-4.48 (m, 0.5H), 4.17-4.06 (m, 0.5H), 4.00-3.91 (m, 0.5H), 3.72-3.61 (m, 0.5H), 3.37-3.28 (m, 0.5H), 3.20-3.08 (m, 0.5H), 2.91-2.83 (m, 0.5H), 2.37-2.12 (m, 2H), 1.98-1.89 (m, 1H), 1.74-1.60 (m, 1H). LC-ESI-MS: 478 [M+H].

Target compound 15i ($R_1$=4-methyl): reagent: Compound 8i (1.3 mmol), acrylic acid (1.3 mmol), DCC (1.3 mmol), DMAP (0.065 mmol); product: white solid, yield: 59% (two steps). LC-ESI-MS: 456 [M+H].

Target compound 15j ($R_1$=4-methoxy): reagent: Compound 8j (1.3 mmol), acrylic acid (1.3 mmol), DCC (1.3 mmol), DMAP (0.065 mmol); product: white solid, yield: 65% (two steps). $^1$H NMR (400 MHz, $CDCl_3$): δ 8.51 (d, J=2.2 Hz, 1H), 8.35 (d, J=11.2 Hz, 1H), 8.02 (dd, J=8.5, 2.2 Hz, 1H), 7.12-7.05 (m, 3H), 6.95-6.80 (m, 2H), 6.66-6.47 (m, 1H), 6.26 (t, J=15.8 Hz, 1H), 5.92-5.75 (brs, 1H), 5.66 (dd, J=36.3, 10.3 Hz, 1H), 4.95-4.86 (m, 1H), 4.85-4.80 (m, 0.5H), 4.58-4.51 (m, 0.5H), 4.20-4.16 (m, 0.5H), 4.04-3.99 (m, 0.5H), 3.82 (s, 3H), 3.76 (t, J=11.5 Hz, 0.5H), 3.38 (t, J=11.3 Hz, 0.5H), 3.22-3.17 (m, 0.5H), 2.93-2.88 (m, 0.5H), 2.45-2.28 (m, 1H), 2.27-2.22 (m, 1H), 2.04-1.96 (m, 1H), 1.78-1.66 (m, 1H). LC-ESI-MS: 472 [M+H].

Target compound 15k ($R_1$=4-trifluoromethyl): reagent: Compound 8k (1.3 mmol), acrylic acid (1.3 mmol), DCC (1.3 mmol), DMAP (0.065 mmol); product: white solid, yield: 58% (two steps). LC-ESI-MS: 509 [M+H].

Example 21: Preparation of Target Compounds 16a-16d

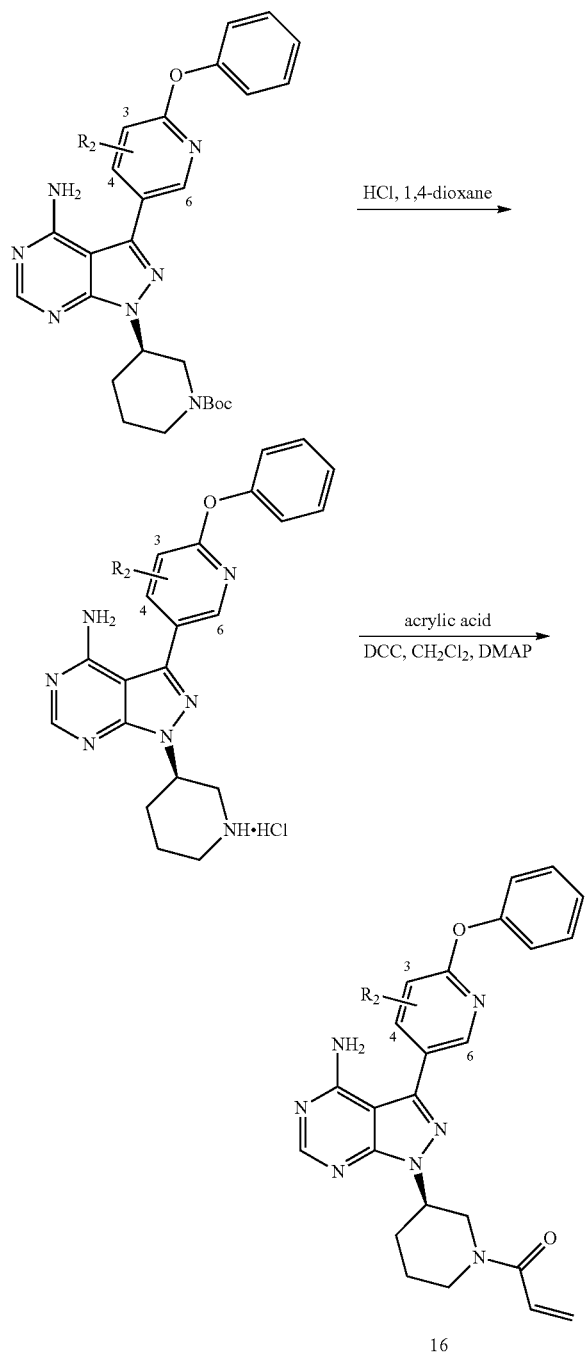

Operation Steps:

1) Corresponding compounds in Compounds 9a-9d (1.3 mmol) were dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a target compound.

Chemical Reagents and Data Characterization:

Target compound 16a ($R_2$=4-fluoro): reagent: Compound 9a (1.3 mmol), acrylic acid (1.3 mmol), DCC (1.3 mmol), DMAP (0.065 mmol); product: white solid, yield: 39% (two steps). LC-ESI-MS: 460 [M+H].

Target compound 16b ($R_2$=3-fluoro): reagent: Compound 9b (1.3 mmol), acrylic acid (1.3 mmol), DCC (1.3 mmol), DMAP (0.065 mmol); product: white solid, yield: 48% (two steps). LC-ESI-MS: 460 [M+H].

Target compound 16c ($R_2$=4-methyl): reagent: Compound 9c (1.3 mmol), acrylic acid (1.3 mmol), DCC (1.3 mmol), DMAP (0.065 mmol); product: white solid, yield: 51% (two steps). LC-ESI-MS: 456 [M+H].

Target compound 16d ($R_2$=6-methyl): reagent: Compound 9d (1.3 mmol), acrylic acid (1.3 mmol), DCC (1.3 mmol), DMAP (0.065 mmol); product: white solid, yield: 46% (two steps). $^1$H NMR (400 MHz, $CDCl_3$): δ 8.51 (d, J=2.2 Hz, 1H), 8.35 (d, J=10.9 Hz, 1H), 7.45 (t, J=7.7 Hz, 2H), 7.23 (d, J=7.4 Hz, 1H), 7.22-7.15 (m, 2H), 7.09-7.03 (d, J=8.4 Hz, 1H), 6.68-6.46 (m, 1H), 6.25 (t, J=15.8 Hz, 1H), 5.95-5.79 (brs, 2H), 5.68 (dd, J=36.1, 10.3 Hz, 1H), 4.97-4.89 (m, 1H), 4.85-4.81 (m, 0.5H), 4.60-4.51 (m, 0.5H), 4.21-4.16 (m, 0.5H), 4.07-3.99 (m, 0.5H), 3.80-3.74 (t, J=11.5 Hz, 0.5H), 3.36-3.30 (t, J=11.3 Hz, 0.5H), 3.21-3.16 (m, 0.5H), 2.93-2.88 (m, 0.5H), 2.55 (s, 3H), 2.47-2.30 (m, 1H), 2.27-2.22 (m, 1H), 2.04-1.93 (m, 1H), 1.80-1.65 (m, 1H). LC-ESI-MS: 456 [M+H].

Example 22: Preparation of Target Compounds 17a and 17c-17i

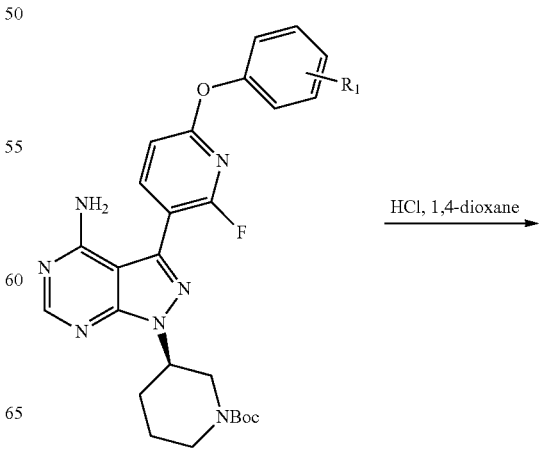

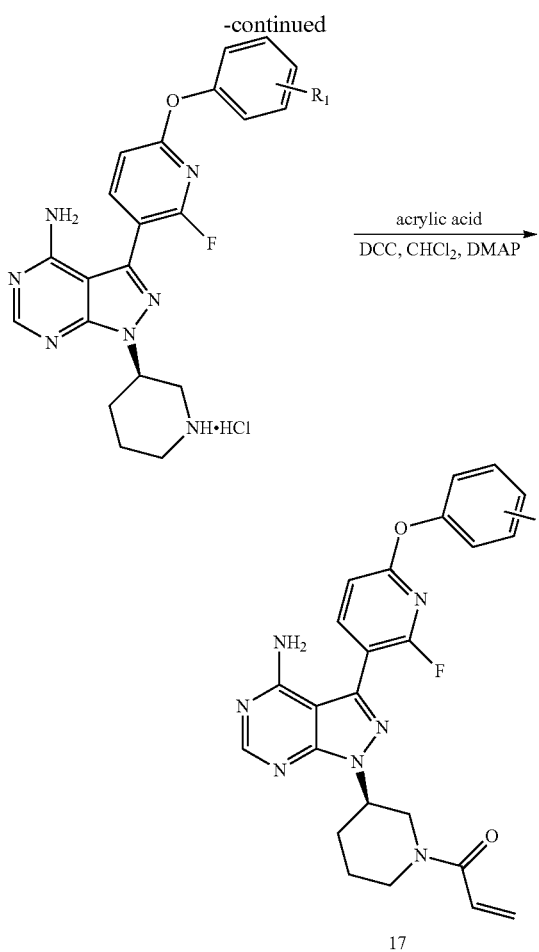

Operation Steps:
1) Corresponding compounds in Compounds 10a and 10c-10i (1.3 mmol) were dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product.

Target compound 17a ($R_1$=H): reagent: Compound 10a (1.3 mmol), acrylic acid (1.3 mmol), DCC (1.3 mmol), DMAP (0.065 mmol); product: white solid, yield: 48%. $^1$HNMR (400 MHz, CDCl$_3$) δ 8.35 (s, 1H), 8.03 (t, J=8.8 Hz, 1H), 7.45 (t, J=7.8 Hz, 2H), 7.35-7.24 (m, 1H), 7.24-7.14 (m, 2H), 6.93 (d, J=7.8 Hz, 1H), 6.70-6.44 (m, 1H), 6.28 (t, J=15.8 Hz, 1H), 5.78-5.45 (m, 3H), 4.96-4.77 (m, 1H, 0.5H), 4.58-4.43 (m, 0.5H), 4.25-4.10 (m, 0.5H), 4.08-3.96 (m, 0.5H), 3.77-3.68 (m, 0.5H), 3.45-3.33 (m, 0.5H), 3.24-3.13 (m, 0.5H), 3.02-2.92 (m, 0.5H), 2.42-2.19 (m, 2H), 2.04-1.96 (m, 1H), 1.78-1.66 (m, 1H). LC-ESI-MS: 460 [M+H].

Target compound 17c ($R_1$=2-fluoro): reagent: Compound 10c (1.3 mmol), acrylic acid (1.3 mmol), DCC (1.3 mmol), DMAP (0.065 mmol); product: white solid, yield: 42%. LC-ESI-MS: 478 [M+H].

Target compound 17d ($R_1$=3-fluoro): reagent: Compound 10d (1.3 mmol), acrylic acid (1.3 mmol), DCC (1.3 mmol), DMAP (0.065 mmol); product: white solid, yield: 47%. LC-ESI-MS: 478 [M+H].

Target compound 17e ($R_1$=4-chloro): reagent: Compound 10e (1.3 mmol), acrylic acid (1.3 mmol), DCC (1.3 mmol), DMAP (0.065 mmol); product: white solid, yield: 39%. LC-ESI-MS: 494 [M+H].

Target compound 17f ($R_1$=4-methyl): reagent: Compound 10f (1.3 mmol), acrylic acid (1.3 mmol), DCC (1.3 mmol), DMAP (0.065 mmol); product: white solid, yield: 35%. LC-ESI-MS: 474 [M+H].

Target compound 17g ($R_1$=4-methoxy): reagent: Compound 10g (1.3 mmol), acrylic acid (1.3 mmol), DCC (1.3 mmol), DMAP (0.065 mmol); product: white solid, yield: 32%. LC-ESI-MS: 490 [M+H].

Target compound 17h ($R_1$=2,6-difluoro): reagent: Compound 10h (1.3 mmol), acrylic acid (1.3 mmol), DCC (1.3 mmol), DMAP (0.065 mmol); product: white solid, yield: 20%. LC-ESI-MS: 496 [M+H].

Target compound 17i ($R_1$=2,3-difluoro): reagent: Compound 10i (1.3 mmol), acrylic acid (1.3 mmol), DCC (1.3 mmol), DMAP (0.065 mmol); product: white solid, yield: 26%. $^1$H NMR (400 MHz, CDCl$_3$) δ 8.38 (s, 1H), 7.86 (q, J=7.9 Hz, 1H), 7.38 (t, J=7.0 Hz, 1H), 7.20 (t, J=7.2 Hz, 1H), 6.96 (d, J=7.8 Hz, 1H), 6.70 (d, J=7.5 Hz, 1H), 6.67-6.48 (m, 1H), 6.37-6.23 (m, 1H), 5.90-5.58 (m, 3H), 4.98-4.82 (m, 1H, 0.5H), 4.63-4.59 (m, 0.5H), 4.24-4.17 (m, 0.5H), 4.06-3.99 (m, 0.5H), 3.80-3.68 (m, 0.5H), 3.43-3.33 (m, 0.5H), 3.25-3.13 (m, 0.5H), 2.93-2.84 (m, 0.5H), 2.46-2.21 (m, 2H), 2.05-1.98 (m, 1H), 1.81-1.67 (m, 1H). LC-ESI-MS: 496 [M+H].

Example 23: Preparation of Target Compound 17b

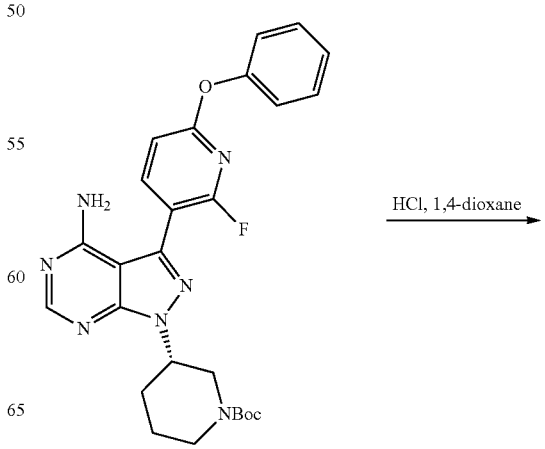

-continued

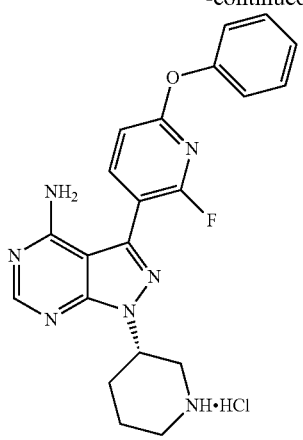
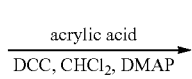

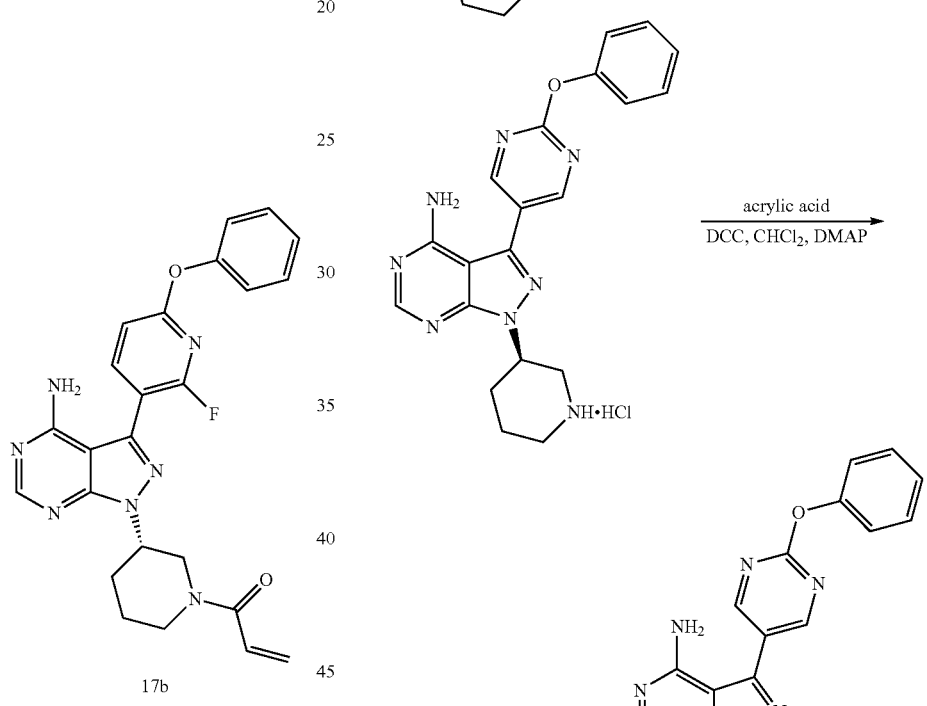

17b

Example 24: Preparation of Target Compound 18

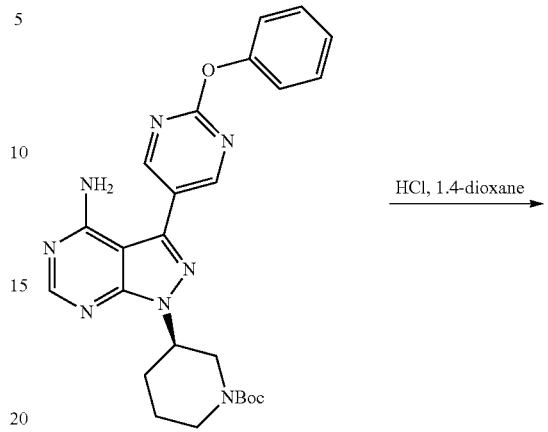

18

Operation Steps:

1) Compound 10b (1.3 mmol) was dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of CH₂Cl₂, and then acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product 17b, with a yield of 45%. LC-ESI-MS: 460 [M+H].

Operation Steps:

1) Compound 11 (1.3 mmol) was dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of CH₂Cl₂, and then acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product, with a yield of 26%. $^1$H NMR (400 MHz, CDCl$_3$): δ 8.89 (s, 2H), 8.39 (d, J=6.8 Hz, 1H), 7.50-7.42 (m, 2H), 7.33-7.29 (m, 1H), 7.24 (d, J=7.6 Hz, 2H), 6.55-6.05 (m, 2H), 5.89-5.77 (m, 1H), 5.71-5.58 (brs, 2H), 4.93-4.48 (m, 2H), 4.32-4.15 (m, 1H), 3.78-3.56 (m, 1H), 3.33-3.08 (m, 1H), 2.83-2.65 (m, 1H), 2.37-2.22 (m, 1H), 2.08-1.69 (m, 2H). LC-ESI-MS: 443 [M+H].

Example 25: Preparation of Target Compound 19

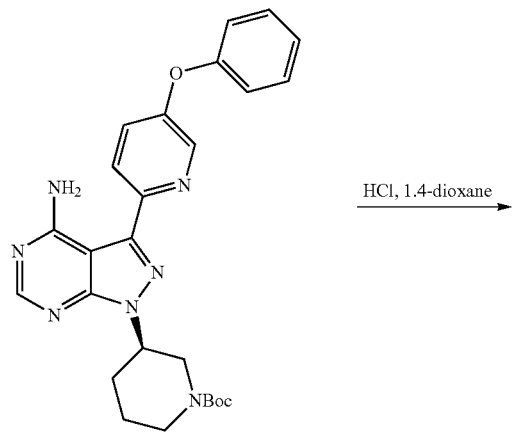

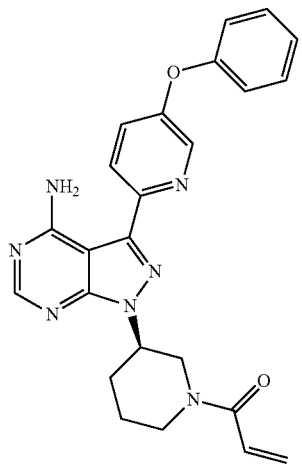

Operation Steps:

1) Compound 12 (1.3 mmol) was dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of CH$_2$Cl$_2$, and then acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product, with a yield of 38%. LC-ESI-MS: 442 [M+H].

Example 26: Preparation of Target Compounds 20a-20c

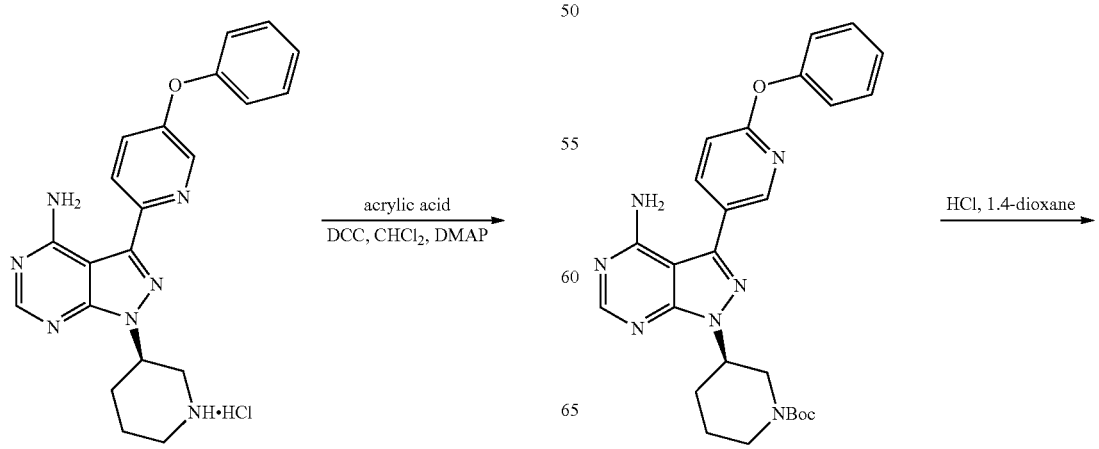

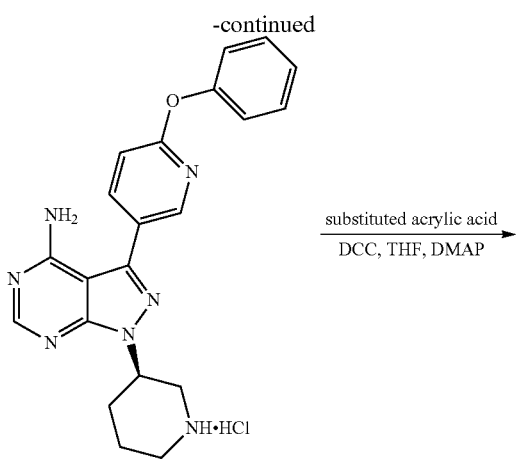

substituted acrylic acid
DCC, THF, DMAP

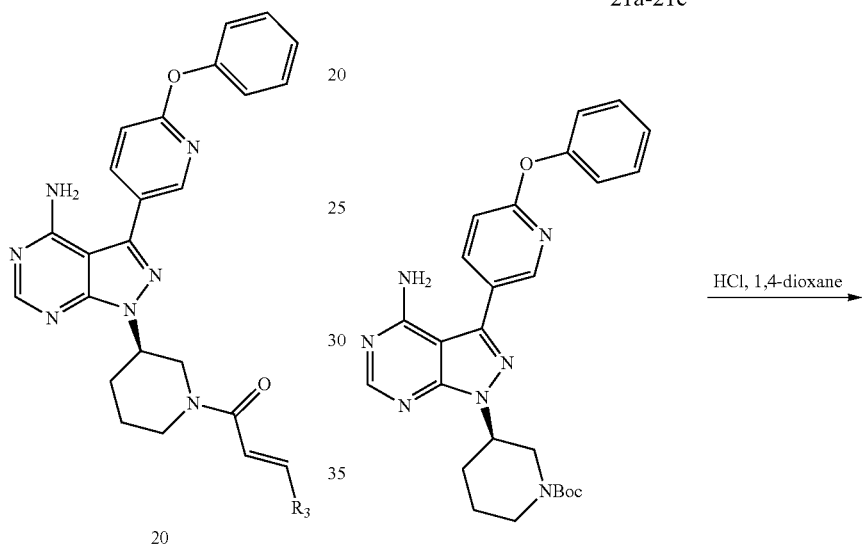

20

Operation Steps:

1) Compound 8a (1.3 mmol) was dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then substituted acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product.

Chemical Reagents and Data Characterization:

Target compound 20a ($R_3$=$CH_2CH_3$), Compound 8a (1.3 mmol), (E)-pent-2-enoic acid (1.3 mmol), DCC (1.3 mmol), DMAP (0.065 mmol); product: white solid, yield: 53% (two steps). LC-ESI-MS: 470 [M+H].

Target compound 20b ($R_3$=$CH_2N(CH_3)_2$), Compound 8a (1.3 mmol), (E)-4-(dimethylamino)-but-2-enoic acid (1.3 mmol), DCC (1.3 mmol), DMAP (0.065 mmol); product: white solid, yield: 42% (two steps). LC-ESI-MS: 499 [M+H].

Target compound 20c ($R_3$=$CH_2CH_2OH$), Compound 8a (1.3 mmol), (E)-5-hydroxypent-2-enoic acid (1.3 mmol), DCC (1.3 mmol), DMAP (0.065 mmol); product: white solid, yield: 21% (two steps). $^1$H NMR (400 MHz, $CDCl_3$): δ 8.51 (d, J=2.2 Hz, 1H), 8.36 (d, J=11.1 Hz, 1H), 8.04 (dd, J=8.5, 2.2 Hz, 1H), 7.44 (t, J=7.7 Hz, 2H), 7.24 (d, J=7.5 Hz, 1H), 7.22-7.15 (m, 2H), 7.07 (d, J=8.4 Hz, 1H), 6.71-6.50 (m, 1H), 6.21-6.10 (m, 1H), 5.92-5.78 (brs, 2H), 4.91-4.85 (m, 1H), 4.77-4.72 (m, 0.5H), 4.55-4.42 (m, 0.5H), 4.19-4.12 (m, 0.5H), 4.04-3.97 (m, 0.5H), 3.78-3.50 (m, 3H), 3.42-3.19 (m, 2H), 3.17-3.09 (m, 0.5H), 2.94-2.85 (m, 0.5H), 2.43-2.27 (m, 2H), 2.25-2.15 (m, 1H), 2.02-1.91 (m, 1H), 1.80-1.71 (m, 1H). LC-ESI-MS: 486 [M+H].

Example 27: Preparation of Target Compounds 21a-21c

HCl, 1,4-dioxane

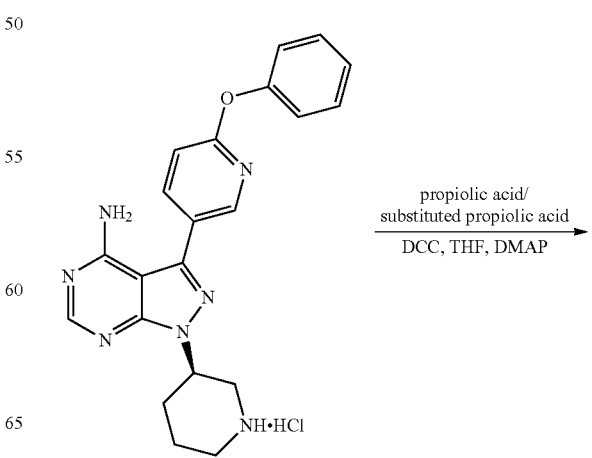

propiolic acid/
substituted propiolic acid
DCC, THF, DMAP

-continued

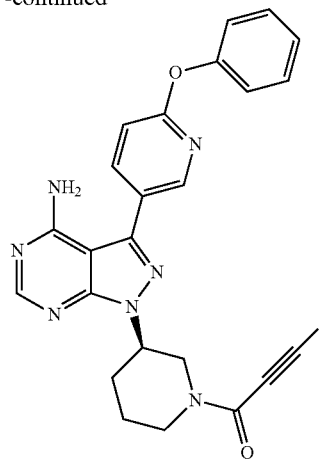

21

Operation Steps:

1) Compound 8a (1.3 mmol) was dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then substituted propiolic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product.

Target compound 21a ($R_3$=$CH_3$), Compound 8a (1.3 mmol), but-2-acetylenic acid (1.3 mmol), DCC (1.3 mmol), DMAP (0.065 mmol); product: white solid, yield: 53% (two steps). $^1$H NMR (400 MHz, CDCl$_3$): δ 8.51 (dd, J=8.7, 2.2 Hz, 1H), 8.32 (d, J=22.4 Hz, 1H), 8.08-8.02 (m, 1H), 7.46-7.37 (m, 2H), 7.24-7.20 (m, 1H), 7.20-7.14 (m, 2H), 7.08 (t, J=8.0 Hz, 1H), 6.16 (brs, 2H), 4.91-4.73 (m, 1H), 4.73 (dd, J=12.8, 4.2 Hz, 0.5H), 4.53 (dd, J=13.0, 4.0 Hz, 0.5H), 4.41 (t, J=14.3 Hz, 1H), 3.86-3.80 (m, 0.5H), 3.41 (dd, J=12.6, 10.8 Hz, 0.5H), 3.30-3.17 (m, 0.5H), 3.01-2.90 (m, 0.5H), 2.46-2.40 (d, J=11.3 Hz, 0.5H), 2.36-2.17 (m, 2H), 2.06-1.97 (m, 3H), 1.81-1.60 (m, 1H). LC-ESI-MS: 454 [M+H].

Target compound 21b ($R_3$=$CH_2N(CH_3)_2$), reagent: Compound 8a (1.3 mmol), 4-(dimethylamino)-but-2-acetylenic acid (1.3 mmol), DCC (1.3 mmol), DMAP (0.065 mmol); product: white solid, yield: 62% (two steps). LC-ESI-MS: 497 [M+H].

Target compound 21c ($R_3$=$CH_2CH_2OH$), reagent: Compound 8a (1.3 mmol), 5-hydroxy-pent-2-acetylenic acid (1.3 mmol), DCC (1.3 mmol), DMAP (0.065 mmol); product: white solid, yield: 29% (two steps). LC-ESI-MS: 484 [M+H].

Example 28: Preparation of Target Compound 22

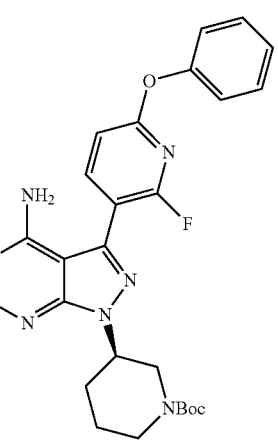

HCl, 1,4-dioxane →

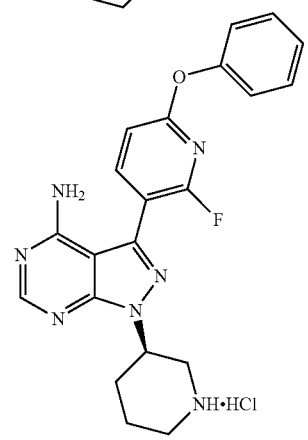

butynoic acid
DCC, THF, DMAP →

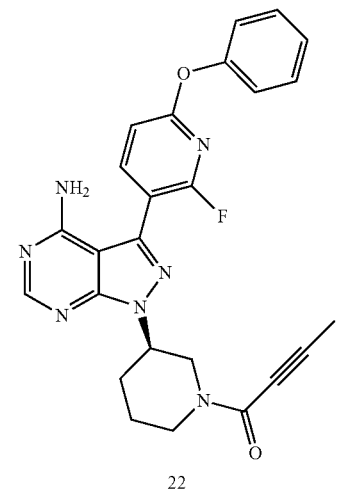

22

Operation Steps:

1) Compound 10a (1.3 mmol) was dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then but-2-acetylene acid (1.3 mmol), dicyclohexylcarbodiimide (DCC, 1.3 mmol), DMAP (0.065 mmol)

were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product, with a yield of 55%. LC-ESI-MS: 472 [M+H].

Example 29: Preparation of Target Compounds 23a-23d

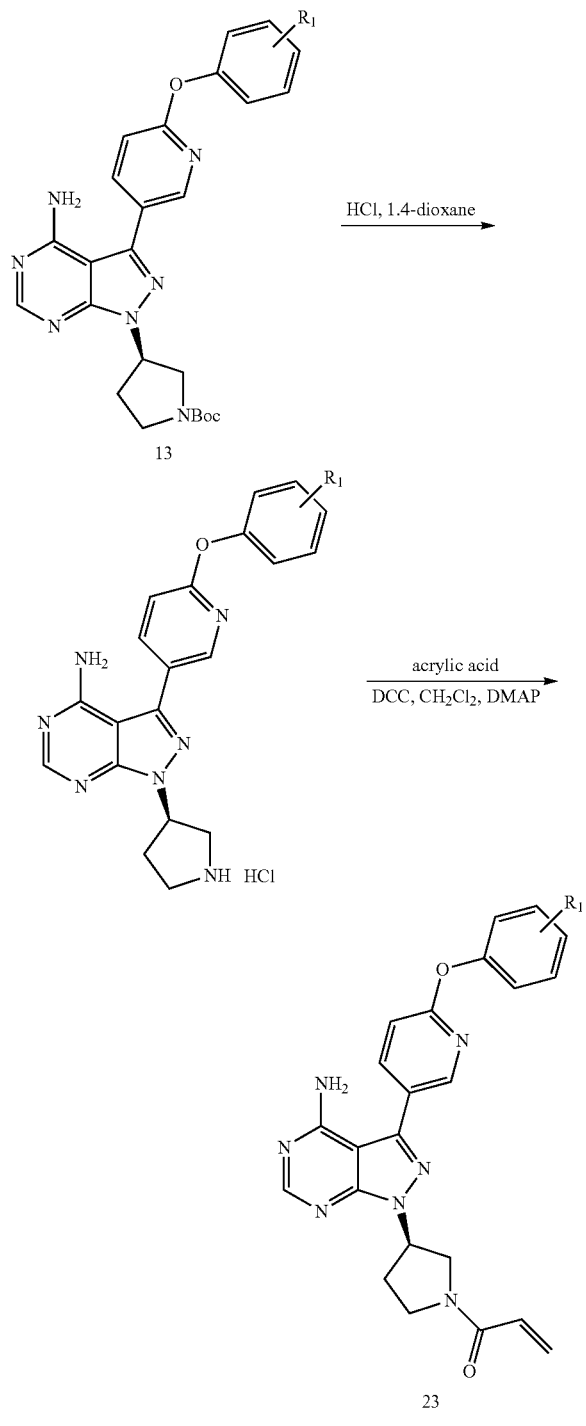

Operation Steps:

1) Corresponding compounds in Compounds 13a-13d (1.3 mmol) were dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product.

Chemical Reagents and Data Characterization:

Target compound 23a ($R_1$=H): reagent: Compound 13a (1.3 mmol), acrylic acid (1.3 mmol), DCC (1.3 mmol), DMAP (0.065 mmol); product: white solid, yield: 49% (two steps). $^1$H NMR (400 MHz, $CDCl_3$) δ 8.49 (s, 1H), 8.38 (d, J=1.8 Hz, 1H), 8.02 (td, J=8.4, 2.4 Hz, 1H), 7.44 (t, J=7.9 Hz, 2H), 7.24 (d, J=7.4 Hz, 1H), 7.19 (d, J=7.6 Hz, 2H), 7.08 (dd, J=8.5, 4.6 Hz, 1H), 6.55-6.34 (m, 2H), 5.74-5.53 (m, 4H), 4.17-3.95 (m, 3H), 3.83-3.72 (m, 1H), 2.72-2.61 (m, 1H), 2.60-2.39 (m, 1H). LC-ESI-MS: 428 [M+H].

Target compound 23b ($R_1$=2-fluoro): reagent: Compound 13b (1.3 mmol), acrylic acid (1.3 mmol), DCC (1.3 mmol), DMAP (0.065 mmol); product: white solid, yield: 45% (two steps). $^1$H NMR (500 MHz, $CDCl_3$) δ 8.43 (s, 1H), 8.37 (d, J=3.3 Hz, 1H), 8.04 (t, J=9.0 Hz, 1H), 7.31-7.13 (m, 5H), 6.53-6.35 (m, 2H), 5.83-5.66 (m, 3H), 5.63-5.52 (m, 1H), 4.18-3.92 (m, 3H), 3.86-3.65 (m, 1H), 2.78-2.61 (m, 1H), 2.60-2.41 (m, 1H). LC-ESI-MS: 446 [M+H].

Target compound 23c ($R_1$=2,6-difluoro): reagent: Compound 13c (1.3 mmol), acrylic acid (1.3 mmol), DCC (1.3 mmol), DMAP (0.065 mmol); product: white solid, yield: 42% (two steps). $^1$H NMR (500 MHz, $CDCl_3$) δ8.40 (d, J=2.8 Hz, 1H), 8.38 (d, J=3.9 Hz, 1H), 8.06 (t, J=9.0 Hz, 1H), 7.33-7.24 (m, 1H), 7.21 (t, J=6.9 Hz, 1H), 7.04 (t, J=8.0 Hz, 2H), 6.54-6.35 (m, 2H), 5.87-5.66 (m, 3H), 5.60-5.53 (m, 1H), 4.16-3.91 (m, 3H), 3.84-3.64 (m, 1H), 2.73-2.60 (m, 1H), 2.59-2.41 (m, 1H). LC-ESI-MS: 464 [M+H].

Target compound 23d ($R_1$=2,3-difluoro): reagent: Compound 13d (1.3 mmol), acrylic acid (1.3 mmol), DCC (1.3 mmol), DMAP (0.065 mmol); product: white solid, yield: 43% (two steps). 1H NMR (500 MHz, $CDCl_3$) δ 8.35 (d, J=1.9 Hz, 1H), 8.30 (s, 1H), 8.02 (d, J=8.4 Hz, 1H), 7.16 (d, J=8.3 Hz, 1H), 7.13-7.02 (m, 2H), 7.01-6.93 (m, 1H), 6.55-6.28 (m, 2H), 5.90-5.71 (m, 3H), 5.66-5.53 (m, 1H), 4.20-3.97 (m, 3H), 3.87-3.69 (m, 1H), 2.78-2.63 (m, 1H), 2.61-2.42 (m, 1H). LC-ESI-MS: 464 [M+H].

Example 30: Preparation of Target Compounds 24a and 24c-24e

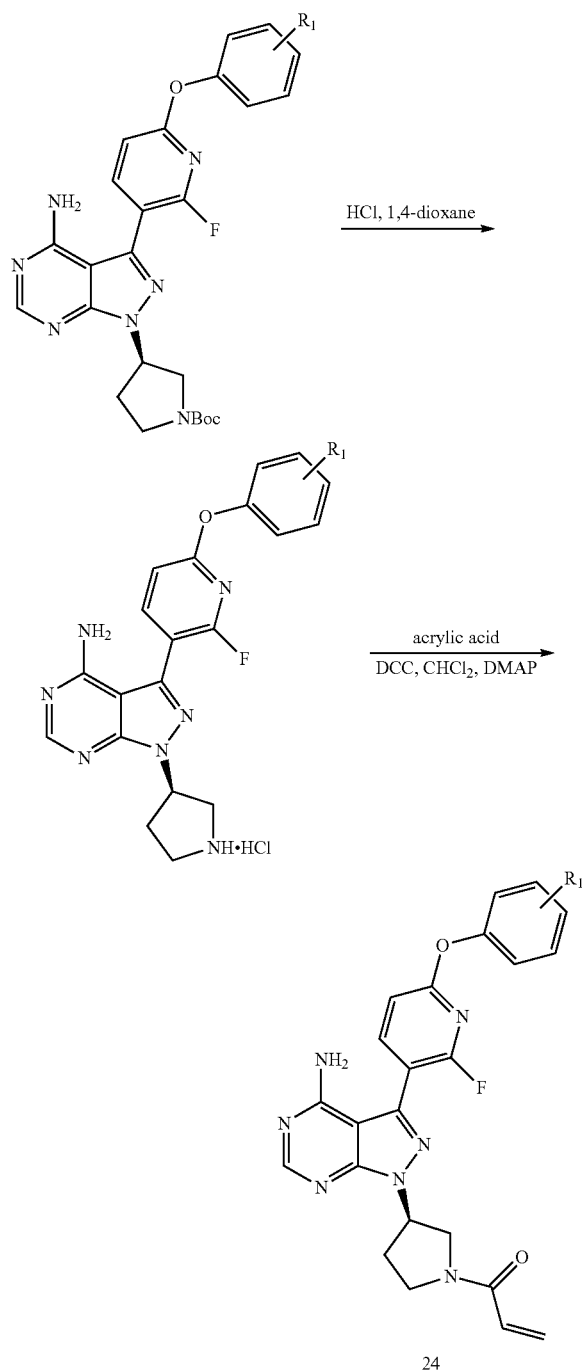

1) Corresponding compounds in Compounds 14a and 14c-14e (1.3 mmol) were dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product.

Chemical Reagents and Data Characterization:

Target compound 24a ($R_1$=H): reagent: Compound 14a (1.3 mmol), acrylic acid (1.3 mmol), DCC (1.3 mmol), DMAP (0.065 mmol); product: white solid, yield: 35% (two steps). $^1$H NMR (500 MHz, $CDCl_3$) δ 8.31 (d, J=2.4 Hz, 1H), 8.05-7.93 (m, 1H), 7.45 (t, J=7.9 Hz, 2H), 7.31-7.24 (m, 1H), 7.19 (d, J=8.2 Hz, 2H), 6.92 (dd, J=12.4, 4.8 Hz, 1H), 6.52-6.34 (m, 2H), 5.90-5.67 (m, 3H), 5.65-5.53 (m, 1H), 4.19-3.94 (m, 3H), 3.83-3.68 (m, 1H), 2.76-2.62 (m, 1H), 2.60-2.42 (m, 1H). LC-ESI-MS: 446 [M+H].

Target compound 24c ($R_1$=2-fluoro): reagent: Compound 14c (1.3 mmol), acrylic acid (1.3 mmol), DCC (1.3 mmol), DMAP (0.065 mmol); product: white solid, yield: 30% (two steps). LC-ESI-MS: 464 [M+H].

Target compound 24d ($R_1$=2,6-difluoro): reagent: Compound 14d (1.3 mmol), acrylic acid (1.3 mmol), DCC (1.3 mmol), DMAP (0.065 mmol); product: white solid, yield: 25% (two steps). LC-ESI-MS: 482 [M+H].

Target compound 24e ($R_1$=2,3-difluoro): reagent: Compound 14b (1.3 mmol), acrylic acid (1.3 mmol), DCC (1.3 mmol), DMAP (0.065 mmol); product: white solid, yield: 28% (two steps). $^1$H NMR (400 MHz, $CDCl_3$) δ 8.39 (d, J=2.2 Hz, 1H), 7.86 (q, J=7.8 Hz, 1H), 7.43-7.31 (m, 1H), 7.24-7.16 (m, 1H), 6.96 (d, J=7.9 Hz, 1H), 6.70 (dd, J=7.9, 2.3 Hz, 1H), 6.57-6.33 (m, 2H), 5.88-5.66 (m, 3H), 5.65-5.55 (m, 1H), 4.19-3.94 (m, 3H), 3.88-3.69 (m, 1H), 2.77-2.61 (m, 1H), 2.60-2.43 (m, 1H). LC-ESI-MS: 482 [M+H].

Example 31: Preparation of Target Compound 24b

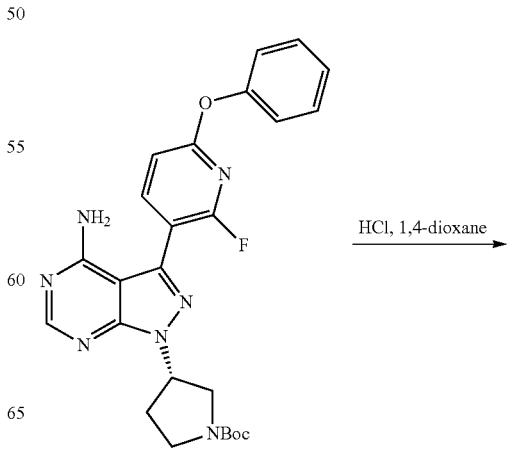

77

-continued

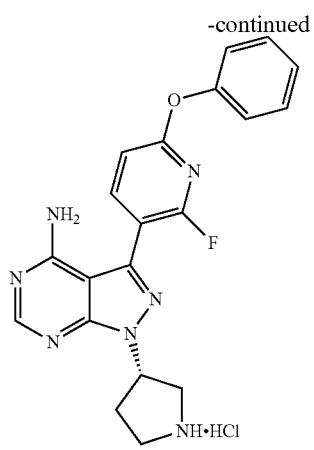

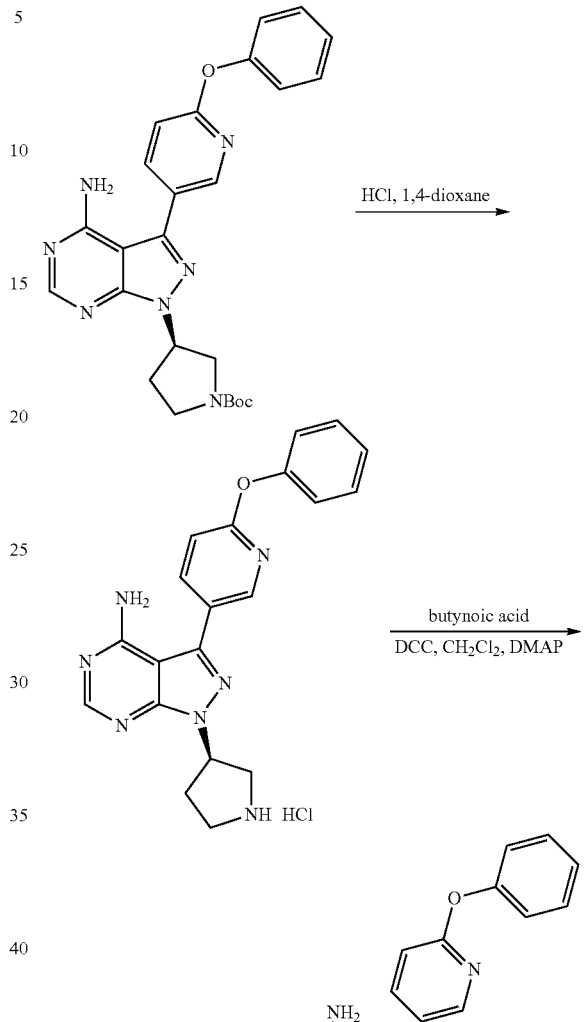

1) Compound 14b (1.3 mmol) was dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then acrylic acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product 24b, with a yield of 32%. LC-ESI-MS: 446 [M+H].

78

Example 32: Preparation of Target Compound 25a

Operation Steps:

1) Compound 13a (1.3 mmol) was dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then but-2-acetylene acid (1.3 mmol), dicyclohexylcarbodiimide (DCC, 1.3 mmol), DMAP (0.065 mmol)

were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product 25a, with a yield of 52%. LC-ESI-MS: 440 [M+H].

Example 33: Preparation of Target Compound 25b

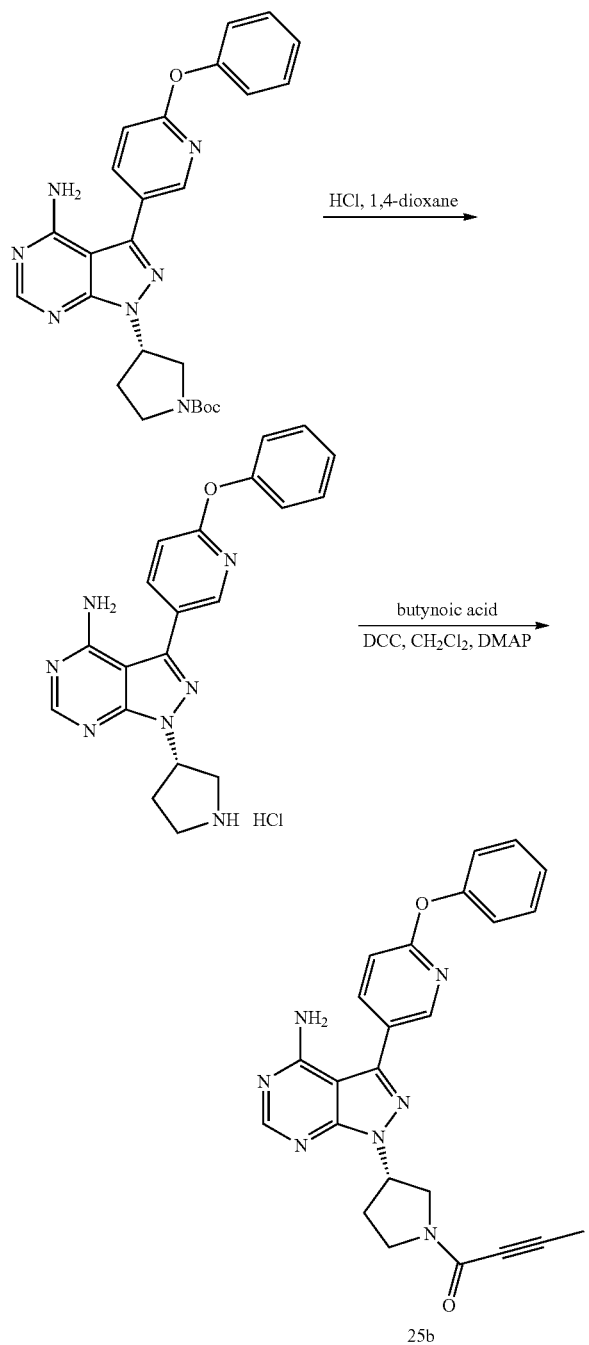

Operation Steps:

1) Compound 13e (1.3 mmol) was dissolved in 15 mL of 1,4-dioxane, 5 mL of 2N HCl was then added dropwise under an ice bath condition, and the solution was stirred at room temperature overnight. The crude product obtained after the solvent was recycled under a reduced pressure was recrystallized with methanol to obtain a white solid product which was directly used in the next step.

2) The obtained solid product was dissolved in 10 mL of $CH_2Cl_2$, and then but-2-acetylene acid (1.3 mmol), dicyclohexylcarbodiimide (DCC, 1.3 mmol), DMAP (0.065 mmol) were added to carry out a reaction for 12 hours. After the reaction was completed under the tracking of TLC, suction filtration was carried out, and filtrate was then concentrated, and column chromatography isolation was carried out with petroleum ether-ethyl acetate as an eluting agent, thus obtaining a white solid product 25b, with a yield of 49%. LC-ESI-MS: 440 [M+H].

Example 34: Test on In-Vitro Btk Kinase Inhibitory Activity and In-Vitro Antitumor Activity In-Vitro Btk Kinase Inhibitory Activity Assay for Compounds of the Present Invention:

The drug was dissolved in DMSO to make a 10 mM (mmol/L) stock solution, and the stock solution was then diluted to a drug solution with 50× test concentrations for later use, wherein the test concentrations were reached through dilution at a 3-fold gradient and were 25 nM (nmol/L), 8.33 nM, 2.78 nM, 0.93 nM, 0.31 nM, 0.10 nM, respectively. 10 μL of the 50× drug stock solution was added to a 96-well plate and then 90 μL of a 1× Kinase Buffer was added and the 96-well plate was shaken for 10 minutes on a shaker. From each well of the 96-well plate, 5 μL of the drug solution was taken and then transferred to a 384-well plate which was provided with 2 duplicate wells.

Kinase Reaction:

Preparation of a 2.5× Kinase Buffer: an enzyme was added to the 1× kinase base buffer.

Prepare a 2.5× oligopeptide solution: FAM-labeled oligopeptide and ATP were added to the 1× kinase base buffer. 10 μL of the 2.5× Kinase Buffer was added to the 384-well plate loaded with 5 μL of the drug solution and incubation was then carried out for 10 minutes at room temperature. 10 μL of the 2.5× oligopeptide solution was added to the 384-well plate and incubation was then carried out for 1 hour at 28° C. The reaction was stopped by adding 25 μL of a stop buffer. The readings were recorded and the inhibition rate of the compound on the enzyme was calculated. The $IC_{50}$ of BTK kinase was calculated by fitting. The test results were shown in Table 1.

The in-vitro antitumor activity assay was carried out on the synthesized compound by using different solid tumors and leukemia cell lines:

Cell lines: human lung cancer cell (A549), human mantle cell lymphoma (MINO), diffuse giant B-cell lymphoma (OCI-LY10), and human diffuse large B lymphoma (TMD-8).

Medium: A549: RPMI 1640+fetal bovine serum
MINO: RPMI 1640+fetal bovine serum
OCI-LY10: IMDM+fetal calf serum
TMD-8: MEM+fetal bovine serum Preparation method of the drug: the drug was dissolved in DMSO to make a 10 mM stock solution, and then the stock solution was diluted in a certain ratio to obtain 5 different concentrations (test concentration 100×). In-vitro culture of tumor cells:

The selected four tumor cells A549, MINO, OCI-LY10, and TMD-8 were incubated in a 37° C., 5% $CO_2$ cell incubator and then were passaged for later experiments when the cell density reaches 70-90% (passage was carried out after adherent cells were digested with Duck's EDTA).

The tumor cells A549, MINO, OCI-LY10, and TMD-8 were seeded in a 96-well plate at 4000 cells/200 μL/well and then incubated overnight at 37° C. in a 5% $CO_2$ cell culture incubator. 2 μL of the compound was added to each well to final concentrations of 50 μM, 10 μM, 2 μM, 0.4 μM, and 0.08 μM and then incubated for 72 hours at 37° C. in a 5% $CO_2$ cell incubator, with DMSO (2%) as a control group. After 72 hours, 20 μL of a CCK-8 solution was added and then the 96-well plate was placed in a 37° C., 5% $CO_2$ cell incubator for incubation for 4 hours. Wells loaded with the corresponding amount of cell culture fluid the and CCK-8 solution but no cells were considered as blank controls. The absorbance (OD value) was measured at 450 nm using a microplate reader, and the obtained data was used to calculate $IC_{50}$. The test results were shown in Table 2.

The cell inhibition rate was calculated as: cell inhibition rate %=[(control group OD value−blank group OD value)−(treatment group OD value−blank group OD value)]/(control cell OD value−blank group OD value)×100%, the half inhibitory concentration ($IC_{50}$) was calculated by CalcuSyn software.

TABLE 1

Inhibitory activities of some compounds against BTK Kinase

| Compound | BTK ($IC_{50}$, nM) |
| --- | --- |
| Ibrutinib | 2.1 |
| I | 2.2 |
| II | 14 |
| 15a | 3.2 |
| 15b | 9.5 |
| 15c | 8.6 |
| 15d | 7.5 |
| 15e | 10.5 |
| 15f | 25.3 |
| 15g | 7.8 |
| 15h | 3.2 |
| 15i | 6.5 |
| 15j | 32.5 |
| 15k | 18.2 |
| 16a | 8.9 |
| 16b | 8.6 |
| 16c | 6.6 |
| 16d | 7.2 |
| 17a | 1.2 |
| 17i | 1.2 |
| 18 | 10.3 |
| 19 | 5.3 |
| 20a | 18.6 |
| 23a | 4.4 |
| 23b | 9.6 |
| 23c | 9.7 |
| 23d | 7.4 |
| 24a | 2.5 |
| 24e | 1.8 |
| 25a | 25.1 |

Compounds I and II were representative compounds reported in the prior patents (Patent Application Nos.: 201510242552.8 and 201610286399.3) published by the inventors (for the specific structures of the compounds I and II, see the background of the present invention).

The data in Table 1 shows that all the compounds obtained by the present invention have significant inhibitory activity against BTK, and the activity of Compound 17a was superior to that of the positive control ibrutinib and was equivalent to that of Compound I (Patent Application No.: 201510242552.8), indicating that introduction of nitrogen atom in the aromatic ring does not affect the inhibitory activity against BTK, and further, the inhibitory activity of Compound 17a was 11.7 times stronger than that of Compound II (Patent Application No.: 201610286399.3). Other derivatives also show potent BTK inhibitory activity with $IC_{50}$ ranging from 1.2 to 32.5, which has further application prospects.

TABLE 2

In-vitro tumor cell proliferation inhibitory activity of some compounds

| | Tumor cell proliferation inhibitory activity ($IC_{50}$, μM) | | Tumor cell proliferation inhibitory activity ($IC_{50}$, nM) | |
| --- | --- | --- | --- | --- |
| Compound | A549 | MINO | OCI-LY10 | TMD-8 |
| Ibrutinib | 9.64 | 3.02 | 1.97 | 2.57 |
| 15a | 1.56 | 6.17 | 2.50 | 8.16 |
| 15b | 2.88 | 8.19 | 3.58 | 2.37 |
| 15c | 2.06 | 6.23 | 2.23 | 4.12 |
| 15d | 5.12 | 9.15 | 5.12 | 3.83 |
| 15i | 8.21 | 8.35 | 3.19 | 4.99 |
| 17a | 1.67 | 8.62 | 1.41 | 5.57 |
| 17i | 1.02 | 7.65 | 2.04 | 3.80 |
| 18 | 19.5 | 20.3 | 32.1 | 8.14 |
| 19 | 4.52 | 7.12 | 13.6 | 10.2 |
| 20a | 7.7 | 8.92 | 12.5 | 15.2 |
| 23a | 2.83 | 9.19 | 6.91 | 28.30 |
| 24a | 2.11 | 9.46 | 2.17 | 16.94 |
| 24e | 1.93 | 8.98 | 4.02 | 7.13 |
| 25a | 5.3 | 6.50 | 5.13 | 5.18 |

The results show that at the cellular level, most of the compounds tested exhibit significant tumor cell proliferation inhibitory activities against tumors, including hematomas and solid tumors. Therefore, the compounds involved in the present invention and used as BTK inhibitors have broad anti-tumor application prospects.

Example 35. hERG Potassium Channel Inhibitory Activity Experiment

1. Cell Culture

The cells used in this experiment were CHO cell lines transfected with HergCdna and stably expressing Herg channels (supplied by Sophion Bioscience, Denmark). The cells were cultured in a medium containing the following components (all from Invitrogen): Ham's F12 medium, 10% (v/v) inactivated fetal bovine serum, 100 μg/ml hygromycin B, 100 μg/ml Geneticin. 2.1.2 CHO Herg cells grow in culture dishes containing the above culture liquid and cultured in a 37° C., 5% $CO_2$ incubator. 24 to 48 hours before an electrophysiological experiment, CHO Herg cells were transferred to circular slides placed in the culture dishes and grow with the same culture liquid under the same culture conditions as above. The density of CHO Herg cells on each circular slide was required to reach such a value that most cells were independent and stand alone.

2. Treatment and Dilution of a Compound

In order to obtain the $IC_{50}$ of the compound, the following concentrations (30, 10, 3, 1, 0.3 and 0.1 Mm) were selected for test. Before the test, the compound was first diluted with DMSO at gradient to make stock solutions with concentrations of 10, 3, 1, 0.3 and 0.1 Mm and the stock solutions were then diluted with extracellular fluid to a final Mm test concentration. Except that the DMSO concentration in the 30 Mm compound test solution was 0.3%, the final concentration of DMSO in each of the compound solutions with other concentrations was 0.1%. The test concentration of a positive control Cisapridewas 0.1 Mm. All compound solutions were conventionally sonicated and shaken for 5 to 10 minutes to ensure complete dissolution of the compound.

3. Electrophysiological Recording System and Data Analysis

This experiment uses a manual patch clamp system (HEKA EPC-10 signal amplifier and digital conversion system, purchased from HEKA Electronics, Germany) for the recording of whole cell currents. The circular slides with CHO Herg cells growing on the surfaces were placed in an electrophysiological recording slot under an inverted microscope. The extracellular fluid was used for continuous perfusion in the recording slot (approximately 1ml per minute). The experimental procedure uses a conventional whole-cell patch clamp current recording technique. Unless otherwise stated, the experiment was carried out at regular room temperature (~25° C.). The cells were clamped at a voltage of −80 Mv. The cell clamp voltage was depolarized to +20 Mv to activate the Herg potassium channel, and 5 seconds later, it was clamped to −50 Mv to eliminate inactivation and generate tail current. The peak of the tail current was used as the value of the Herg current. After the hERG potassium current recorded in the above step was stabilized under the continuous extracellular fluid perfusion in the recording slot, the drug to be tested can be superimposed to the perfusion until the inhibitory effect of the drug on the hERG current reaches a steady state. Generally, the criterion for determine whether or not the stable state was reached was that the recent three consecutive current recording lines were coincident. After the steady state was reached, extracellular fluid perfusion was carried out for flushing until the hERG current returns to the magnitude before the drug was added. One cell may be used for testing one or more drugs, or multiple concentrations of the same drug, and flushing with extracellular fluid was carried out between tests of different drugs. Cisapride (purchased from Sigma) was used in the experiment as a positive control to ensure that the cells used were of normal quality. The test data was analyzed by data analysis software provided by HEKA Patchmaster, Microsoft Excel and Graphpad Prism. The test results were shown in Table 3.

TABLE 3 hERG potassium channel blocking activity of some compounds

| Name of Compound | hERG $IC_{50}$ (µM) |
| --- | --- |
| Ibrutinib | 3.51 |
| I | 0.91 |
| II | 5.19 |
| 15a | 15.48 |
| 15b | 11.6 |
| 15i | 13.5 |
| 15j | 17.5 |
| 16a | 6.9 |
| 17a | 7.8 |
| 19 | 10.6 |
| 20a | 14.8 |
| 21c | 25.2 |
| 23a | 18.2 |
| 24a | 7.66 |
| 25a | 13.6 |

Compounds I and II were representative compounds reported in the prior patents (Patent Application Nos.: 201510242552.8 and 201610286399.3) published by the inventors (for the specific structures of the compounds I and II, see the background of the present invention).

The test results of Table 3 indicate that the hERG channel blocking effects of the compounds of the present invention were markedly weak. For example, the $IC_{50}$ of Compound 15a was 15.48 µM, 4.41 times that of ibutinib. Compared with Compound II in the BTK patent document (Patent Application No.: 201610286399.3), the $IC_{50}$ of Compound 15a was 2.98 times that of Compound II. Since hERG channel blocking effect was associated with the risk of cardiotoxicity of the drug. Therefore, the low hERGpotassium channel blocking activity of this class of compounds was beneficial to reducing the risk of toxic side effects and improving their druggability.

Example 36. Kinase Selectivity Experiment

A 1× kinase base buffer and a reaction stop buffer for respective kinases in the experiment were prepared as required.

Preparation of Compounds to be Tested:

1) Using DMSO to prepare 50× compound stock solutions (same as the stock solution in Example 34) for later use;

2) diluting each compound at a 5-fold concentration gradient in a 96-well plate to 6 to 7 concentrations and ensuring that the drug volume in each well was 10 µl; and at the same time adding 100 µl of DMSO to prepare a blank control group and also preparing a negative control group without the enzyme substrate; and 3) preparing another 96-well plate, adding 10 µl of each of the above compounds to 90 µl of the 1× kinase base buffer and mixing for 10 minutes to be uniform.

Preparation of the Plate to be Tested:

1) 5 µl of the mixed solution prepared as above in the 96-well plate was taken and transferred to a 384-well plate, with two replicate wells for each compound.

Kinase Reaction:

1) Preparing a 2.5× kinase solution and adding a corresponding 1× kinase base buffer;

2) preparing a 2.5× polypeptide solution and adding FAM-labeled polypeptide and ATP in the 1× kinase base buffer; and 3) adding 10 µl of 2.5× kinase solution to a 384-well plate to be tested, placing in a room-temperature environment for 10 minutes, and then adding 10 µl of the 2.5× polypeptide solution, reacting at 28° C. for 1 hour, and then adding 25 µl of a reaction stop buffer.

The Caliper program reads the plate and uses the data to obtain the $IC_{50}$ values of the corresponding compounds against kinases. The test results are shown in Table 4.

TABLE 4

Inhibitory activities of some compounds against various kinases ($IC_{50}$, nM)

| Kinase | Ibrutinib | I | 15a | 17a | 24a |
| --- | --- | --- | --- | --- | --- |
| ITK | 186 | 428 | >1000 | >1000 | >1000 |
| BLK | 0.58 | 1.6 | 30 | 11 | 5.4 |
| CSK | 37 | 180 | >1000 | >1000 | >1000 |
| FGR | 8.0 | 27 | >1000 | >1000 | >1000 |
| HCK | 179 | >1000 | >1000 | >1000 | >1000 |
| JAK3 | 105 | 901 | >1000 | >1000 | >1000 |
| FLT3 | 231 | 350 | >1000 | >1000 | >1000 |

Compound I was a representative compound reported in the prior patent (Patent Application No.: 201510242552.8) published by the inventors (for the specific structure of the compound I, see the background of the present invention).

The test results of Table 4 show that the compounds designed by the present invention have obvious selectivity advantages for kinases, and with Compound 15a as an example, and its inhibitory activity against kinases such as ITK, CSK, FGR, HCK, JAK3, and FLT3 was very weak, and the activities of most of the kinases were greater than 1000 nM; therefore, its kinase selectivity for BTK was significantly better than that of Ibutinib and Compound I, and thus, such compounds will have significant advantages in side effects caused by poor selectivity.

Example 37: Oral Pharmacokinetic Experiment of Drug

Experimental Method

SD rats were used as experimental animals and were subjected to intragastric administration in a dose of 10 mg/kg and tail-vein intravenous injection in a dose of 2 mg/kg. The tail-vein blood sampling time points in the intragastric administration were 0.17, 0.33, 0.5, 1, 1.5, 2, 4, 6, 8, 12, and 24 hours; the blood sampling time points in the intravenous administration were 0.05, 0.1, 0.17, 0.5, 1, 2, 4, 6, 8, 12, and 24 hours. 0.3 ml of whole blood was taken, and 0.1 ml of plasma after centrifugation was taken and analyzed by LC-MS.

TABLE 5

Summary of main pharmacokinetic parameters of SD rats after oral administration

| Parameter (Mean, n = 3) | Ibrutinib | 15a | 24a | 24e |
|---|---|---|---|---|
| Dose (mg/kg) | 10.0 | 10.0 | 10.0 | 10.0 |
| $C_{max}$ (ng/mL) | 254 | 292 | 548 | 1440 |
| $T_{max}$(h) | 0.250 | 0.333 | 0.750 | 0.250 |
| $T_{1/2}$(h) | 3.09 | 6.17 | 1.70 | 3.57 |
| $AUC_{0-t}$ (ng/h/mL) | 544 | 624 | 2085 | 1600 |
| $AUC_{0-C}$(ng/h/mL) | 550 | 698 | 2136 | 1625 |
| F(%) | 12.5 | 20.9 | 57.8 | 46.1 |

The pharmacokinetic properties of Compounds 15a, 24a and 24e in rats were examined by using ibrutinib as a reference. The test results of Tables 5 and 6 show that the oral bioavailability of Compounds 15a, 24a and 24b were obviously improved and were 1.67, 4.62 and 3.69 times of that of ibrutinib, respectively. Therefore, the compounds of the present invention can be administered by oral absorption for the treatment of diseases.

Example 38: In-Vivo Pharmacodynamic Study of Compounds 15a, 17a, 24a and 24e on Mino Subcutaneous Xenograft Tumor Models Experimental Method In CB17 SCID mice, 0.2 mL of cell suspension containing 5×10^6 Mino cells was subcutaneously inoculated into the right back of each mouse, and when the mean tumor volume reaches approximately 139.94 mm3 (day 26 after inoculation), group administration was started (intragastric administration, twice a day, 14 days in total). Animals were monitored daily for health and mortality, and tumor diameters were measured twice a week using vernier calipers to see if tumor growth could be inhibited, delayed, or cured. The efficacy in tumor volume was evaluated by TGI, TGI (%)=(1−(TV$_{Control-Dn}$−TV$_{Control-D0}$)/(TV$_{treatment-Dn}$−TV$_{treatment-D0}$)/×100%, TV$_{Control}$ refers to the tumor volume of the control group, TV$_{Treatment}$ refers to the tumor volume of the treatment group. If TGI≥58%, the drug was considered effective. The efficacy in tumor weight was evaluated by TGI %, tumor weight inhibition rate (TGI) %=(TW$_C$−TW$_T$)/TW$_C$×100%, TW$_C$: tumor weight of the control group, TW$_T$: tumor weight of the treatment group. According to the NIH guidelines, if TGI≥58%, the drug was considered effective.

TABLE 6

In-vivo pharmacodynamic treatment results of the Mino subcutaneous xenograft tumor models

| Group | TGI*(14 days) (%) | TGI**(14 days) (%) |
|---|---|---|
| Blank group | — | — |
| II | 59.14 | 58.29 |
| 15a | 65.01 | 61.00 |
| 17a | 82.54 | 74.05 |
| 24a | 73.80 | 65.19 |
| 24e | 68.04 | 62.16 |

Note:
TGI*: calculated on the basis of tumor volume;
TGI**: calculated on the basis of tumor weight. Compound IIwas a representative compound reported in the prior patent (Patent Application No.: 201610286399.3) published by the inventors (for the specific structure of the compound II, see the background of the present invention).

Test results: During the administration period, all the mice show good performance in body weight. At the end of the last administration, tumors were taken and weighed, and the tumor weight TGI evaluation shows that the TGIs of all the mice were greater than 58% (see Table 6), showing a good tumor inhibitory effect. The compounds of the present invention have certain advantages in in-vivo tumor activity as compared with Compound II.

Example 39: Treatment of Rheumatoid Arthritis with Compounds 15a, 17a, 24a and 24e In Balb/c mice, arthritis was induced by administration of anti-collagen antibodies and lipopolysaccharides (Nandakumar et al., Am. J. Pathol. 2003, 163: 1827-1837).

The specific method was as follows: On Day 0, female Balb/c mice were intravenously injected with anti-type II collagen ChemicomAb mixture in a dose of 100 mg/kg, and on Day 1, lipopolysaccharide was intraperitoneally injected in a dose of 1.25 mg/kg. From Day 2 to Day 12, Compounds 15a, 17a, 24a and 24e were orally administered once a day in a dose of 10 mg/kg. On Day 13 after abdominal anesthesia, 4 ml of blood was taken from the femoral artery and centrifuged at 3000 r/min for 20 minutes, serum was taken to detect IL-1β with a test kit, and related tissue samples were observed. The IL-1β test results were shown in Table 7.

TABLE 7

IL-1β test results

| Group | IL-1β(ng/L) |
|---|---|
| Blank group | 15.32 ± 5.6 |
| Model group | 35.55 ± 9.2 |
| 15a | 18.72 ± 6.6 |
| 17a | 17.25 ± 3.9 |
| 24a | 19.32 ± 4.2 |
| 24e | 20.45 ± 5.1 |

The results show that Compounds 15a, 17a, 24a and 24e all can significantly reduce the level of IL-1β in serum and have in-vivo anti-rheumatoid arthritis effect. Furthermore, the phenomena such as inflammatory cell infiltration, synovial hyperplasia, inflammatory granulation tissue formation, and necrotic tissue appearing in the model group were significantly improved after treatment with Compounds 15a, 17a, 24a and 24e.

The invention claimed is:

1. A compound, having a structure of Formula II or Formula II':

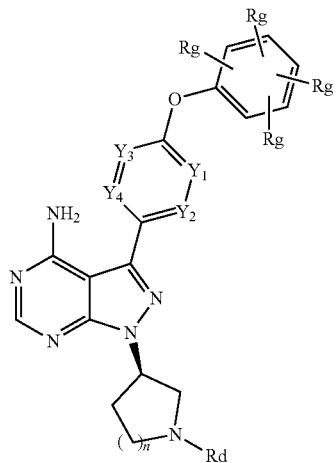

II

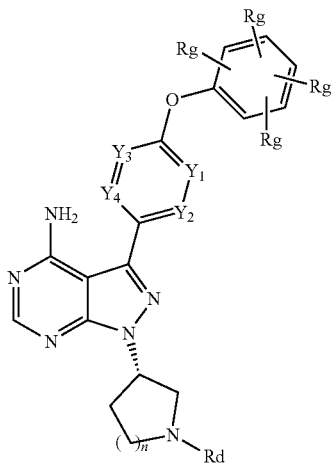

II' or their optical isomers, or pharmaceutically acceptable salts or solvates;

where each Rg is independently H, halogen, —CF$_2$H, —CF$_3$, —CN, C1-C3 alkyl, or C1-C3 alkoxy;

n is selected from 0, 1 and 2;

Rd is selected from

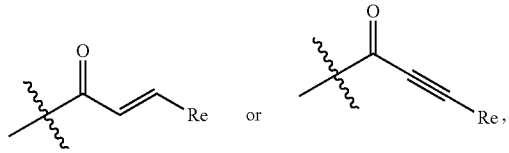

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl are further substituted with amino, hydroxyl, and C1-C3 alkyl;

Y$_1$, Y$_2$, Y$_3$ and Y$_4$ are independently selected from C(Rf) and N, and at least one of Y$_1$, Y$_2$, Y$_3$ and Y$_4$ is N, wherein Rf is selected from H, halogen, C1-C3 alkyl, —CF$_3$, and —CF$_2$H.

2. A compound according to claim 1, having a structure of Formula III or Formula III' or Formula III":

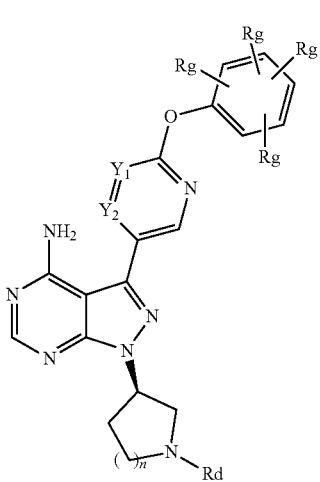

III

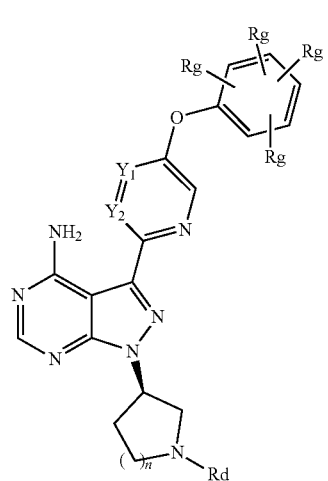

III'

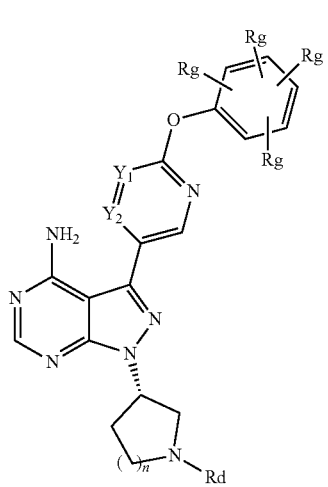

III"

and their optical isomers, or pharmaceutically acceptable salts or solvates;

where each Rg is independently H, halogen, —CF$_2$H, —CF$_3$, C1-C3 alkyl, or C1-C3 alkoxy;

n is selected from 0, 1 and 2;

Rd is selected from

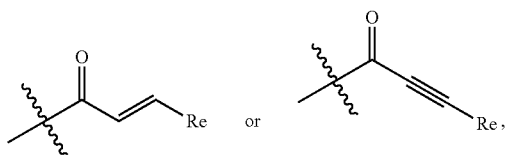

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl are further substituted with amino, hydroxyl, and C1-C3 alkyl;

Y$_1$ and Y$_2$ are independently selected from C(Rf) and N, wherein Rf is selected from H, halogen, C1-C3 alkyl, —CF$_3$, and —CF$_2$H.

3. A compound according to claim 2, having a structure of Formula IV or Formula IV' or Formula IV'':

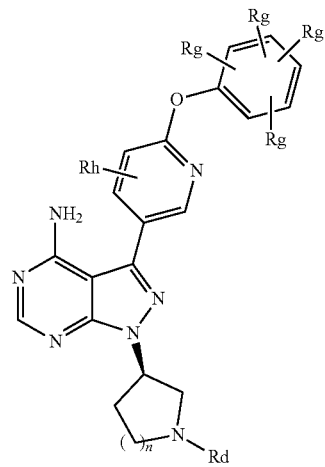

IV

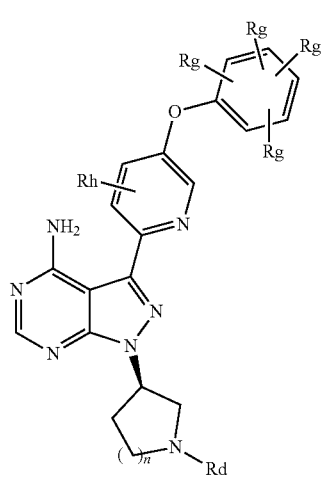

IV'

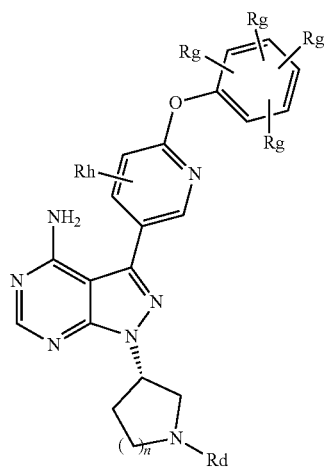

IV'' and their optical isomers, or pharmaceutically acceptable salts or solvates;

where each Rg is independently H, halogen, —CF$_2$H, —CF$_3$, C1-C3 alkyl, or C1-C3 alkoxy;

n is selected from 0, 1 and 2;

Rd is selected from

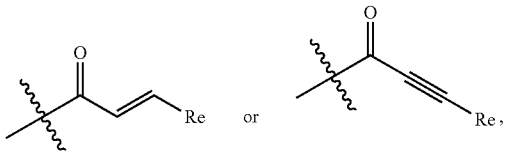

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl are further substituted with amino, hydroxyl, and C1-C3 alkyl;

Rh is independently selected from H, halogen, C1-C3 alkyl, —CF$_3$, and —CF$_2$H.

4. A compound according to claim 3, having a structure of Formula V or Formula V' or Formula V'':

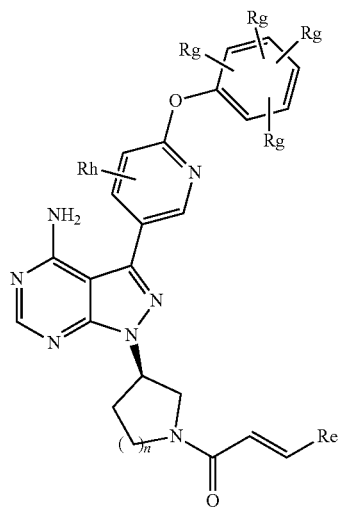

V

-continued

V'

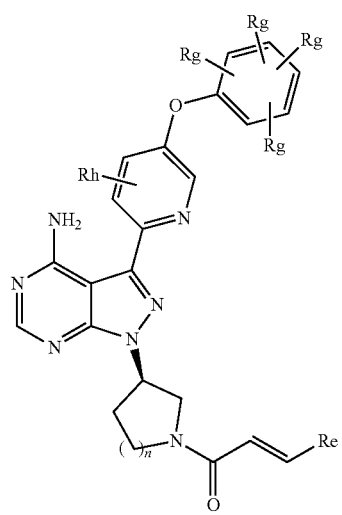

V"

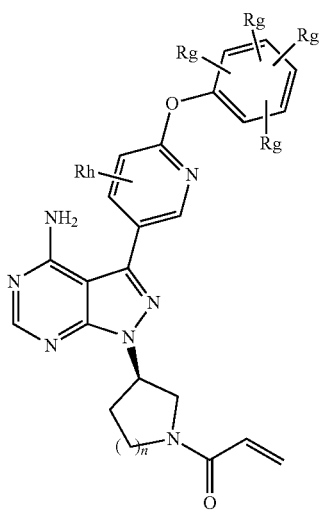

and their optical isomers, or pharmaceutically acceptable salts or solvates;

where each Rg is independently H, halogen, —CF$_2$H, —CF$_3$, C1-C3 alkyl, or C1-C3 alkoxy;

n is selected from 0, 1 and 2;

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl are further substituted with amino, hydroxyl, and C1-C3 alkyl;

Rh is selected from H, halogen, C1-C3 alkyl, —CF$_3$, and —CF$_2$H.

5. A compound according to claim 4, having a structure of Formula VI or Formula VI' or Formula VI":

VI

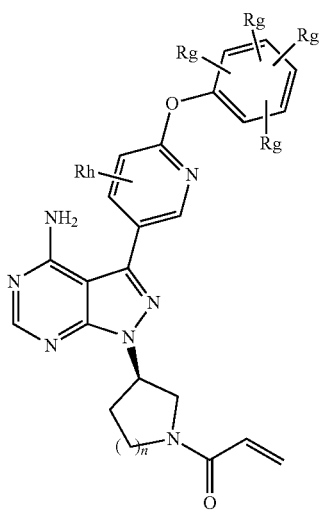

VI'

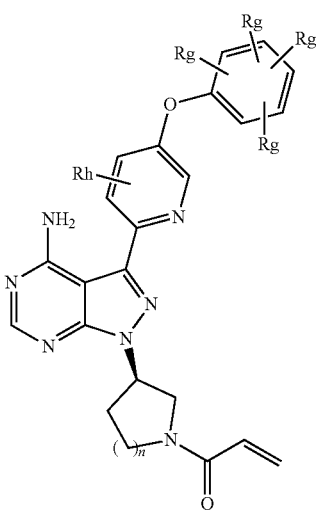

VI"

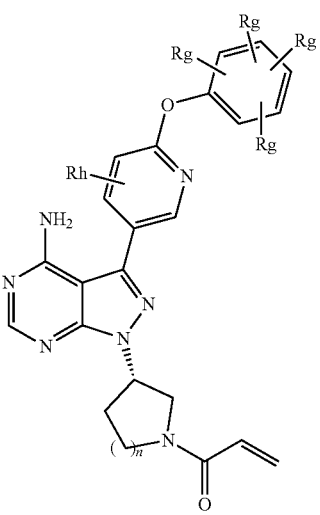

and their optical isomers, or pharmaceutically acceptable salts or solvates;

where each Rg is independently H, halogen, —CF$_2$H, —CF$_3$, C1-C3 alkyl, or C1-C3 alkoxy;

n is selected from 0, 1 and 2;

Rh is independently selected from H, halogen, C1-C3 alkyl, —CF$_3$, and —CF$_2$H.

6. A compound according to claim 5, having a structure of Formula VI-a or Formula VI-a' or Formula VI-a":

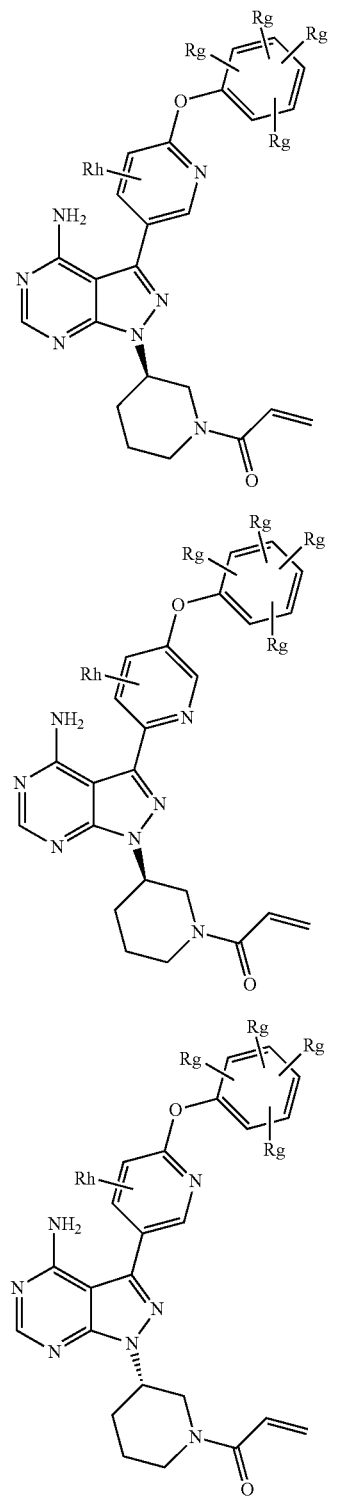

and their optical isomers, or pharmaceutically acceptable salts or solvates;

where each Rg is independently H, halogen, —CF$_2$H, —CF$_3$, C1-C3 alkyl, or C1-C3 alkoxy;

Rh is independently selected from H, halogen, C1-C3 alkyl, —CF$_3$, and —CF$_2$H.

7. A compound according to claim 6, having a structure of Formula VI-a-1 or Formula VI-a-2':

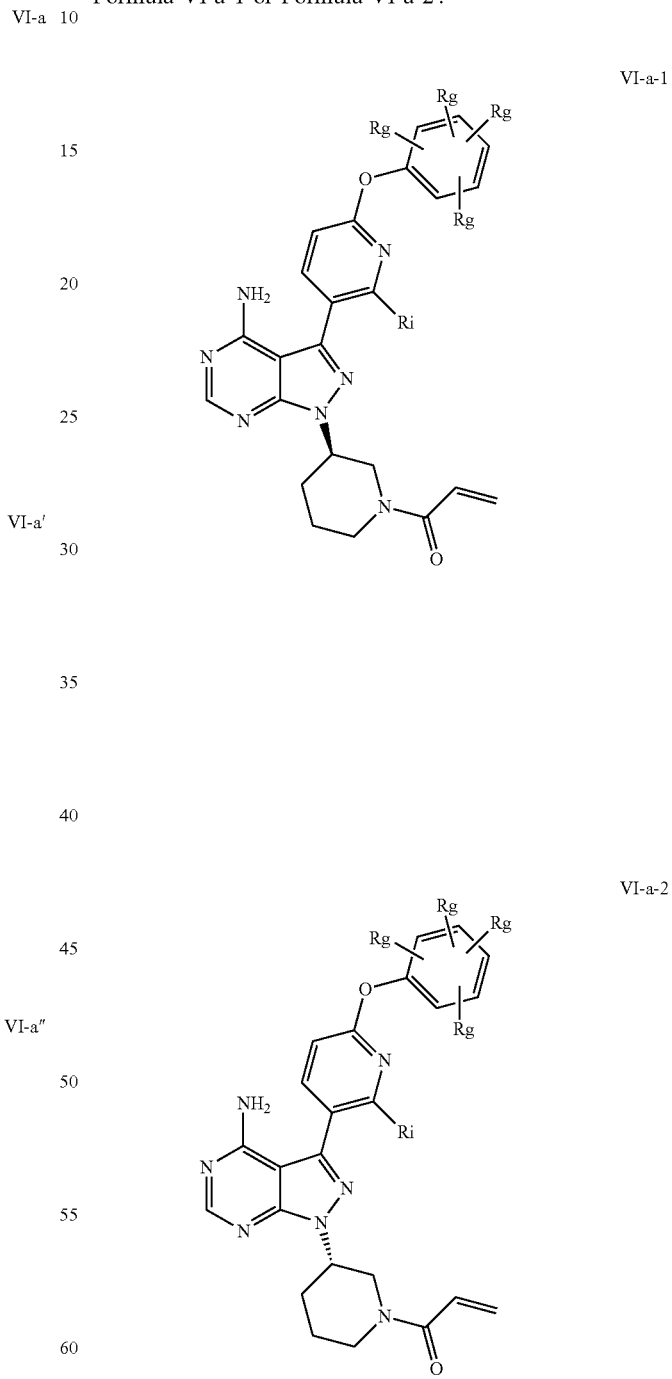

where each Rg is independently H, halogen, —CF$_2$H, —CF$_3$, C1-C3 alkyl, or C1-C3 alkoxy;

Ri is independently selected from H, halogen, C1-C3 alkyl, —CF$_3$, and —CF$_2$H.

8. A compound according to claim 3, having a structure of Formula VII or Formula VII' or Formula VII":

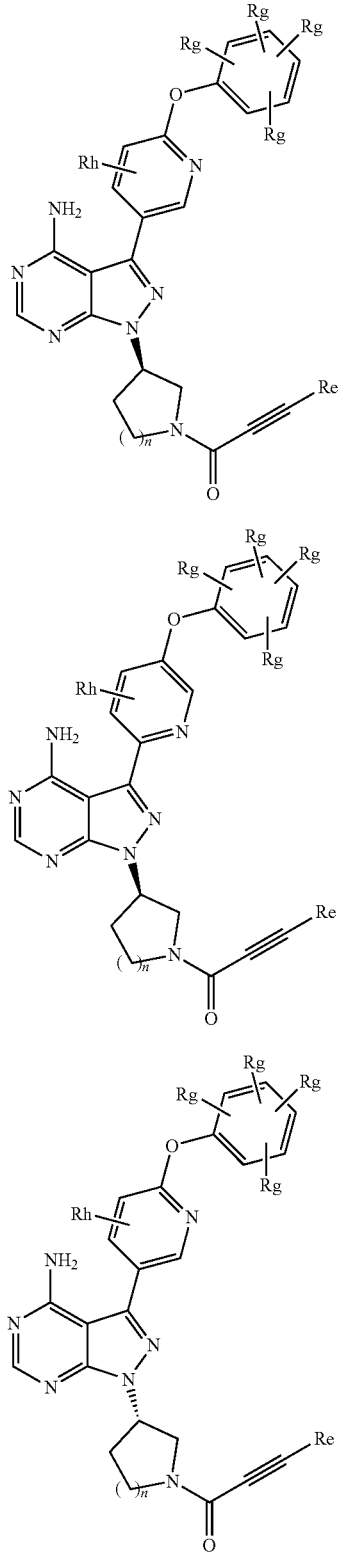

and their optical isomers, or pharmaceutically acceptable salts or solvates;

where each Rg is independently H, halogen, —CF$_2$H, —CF$_3$, C1-C3 alkyl, or C1-C3 alkoxy;

n is selected from 0, 1 and 2;

Re is selected from H, CH$_3$, C2-C6 alkyl, C1-C6 azaalkyl, and C1-C6 oxaalkyl, wherein CH$_3$, C2-C6 alkyl, C1-C6 azaalkyl and C1-C6 oxaalkyl may be further substituted with amino, hydroxyl, and C1-C3 alkyl;

Rh is independently selected from H, halogen, C1-C3 alkyl, —CF$_3$, and —CF$_2$H.

9. A compound according to claim 8, having a structure of Formula VIII or Formula VIII' or Formula VIII":

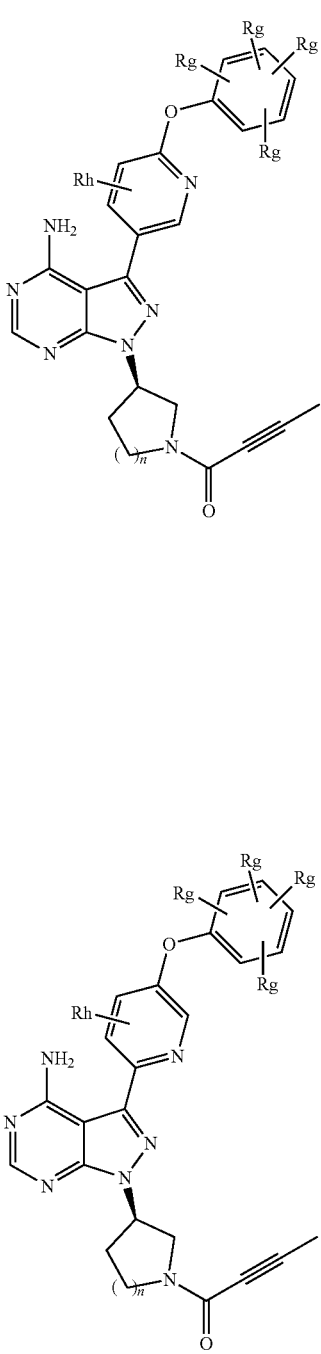

-continued
VIII″
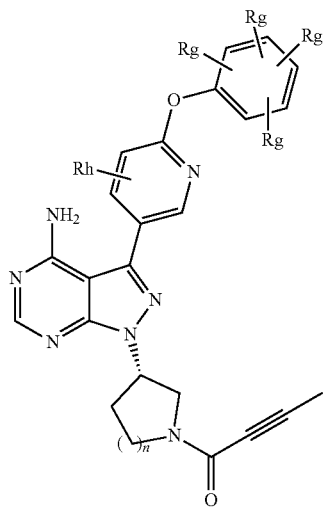
and their optical isomers, or pharmaceutically acceptable salts or solvates;
where each Rg is independently H, halogen, —CF$_2$H, —CF$_3$, C1-C3 alkyl, or C1-C3 alkoxy;
n is selected from 0, 1 and 2;
Rh is independently selected from H, halogen, C1-C3 alkyl, —CF$_3$, and —CF$_2$H.
10. A compound according to claim 1, having a structure of one of the following formulas:
15a
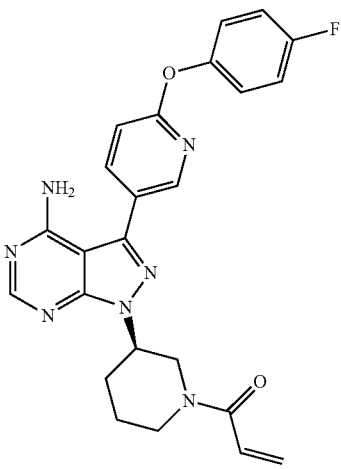
-continued
15b
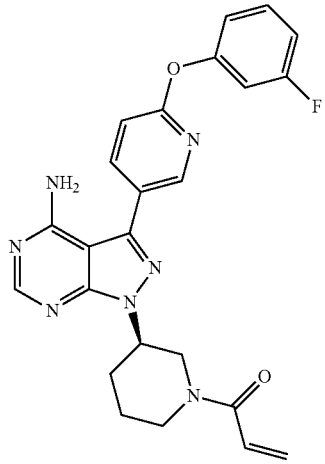
15c
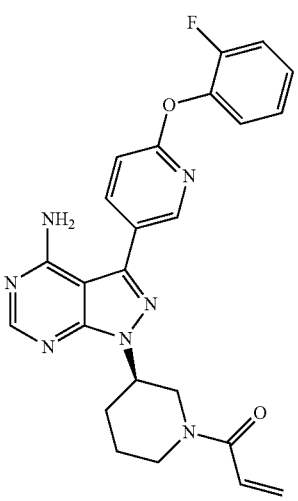
15d 15e
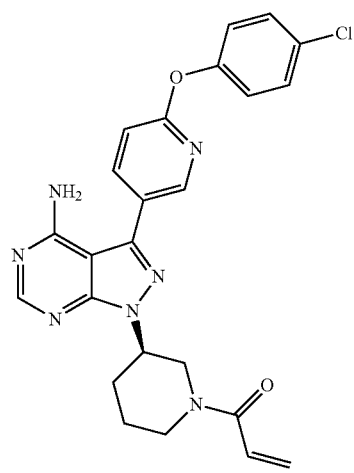
15f
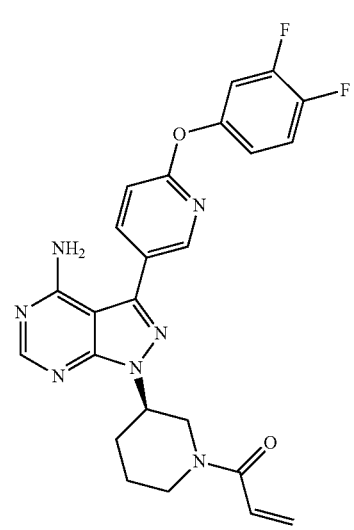
15g
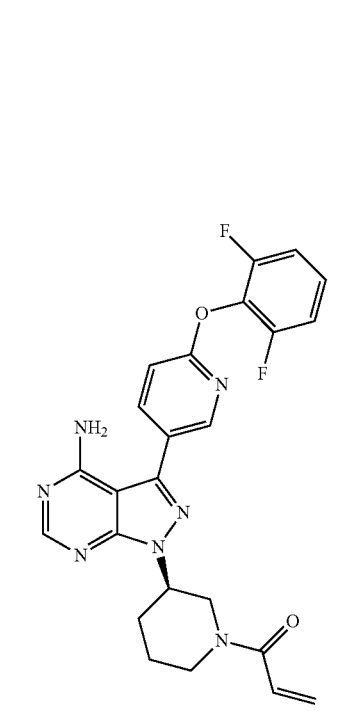
15h
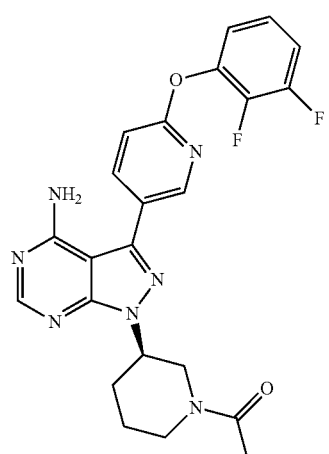
15i
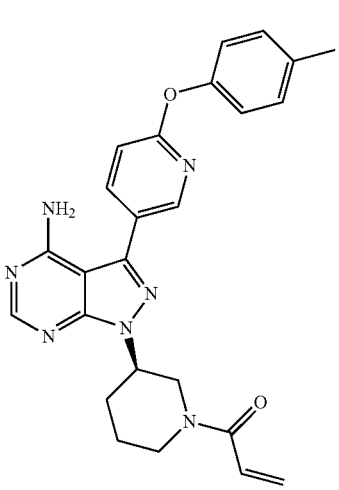
15j
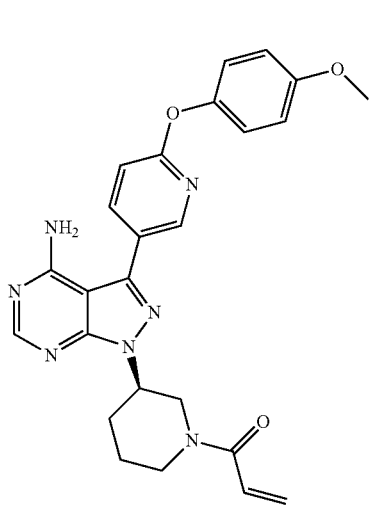

15k
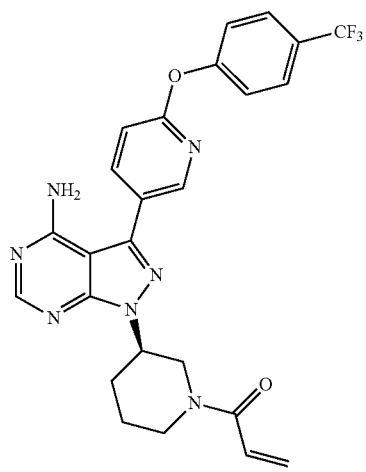
16a
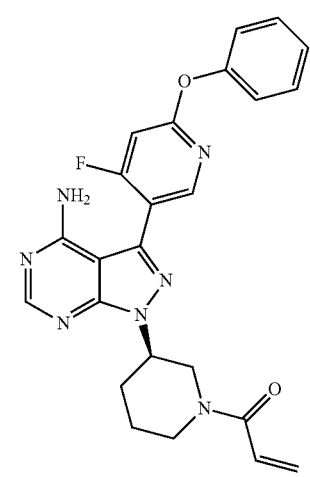
16b
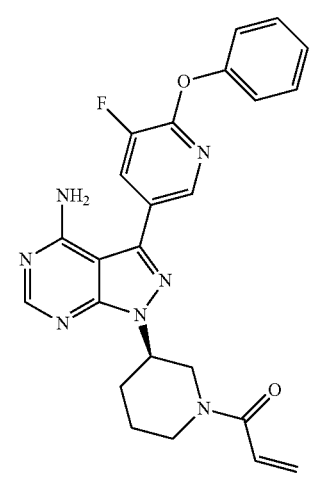
16c
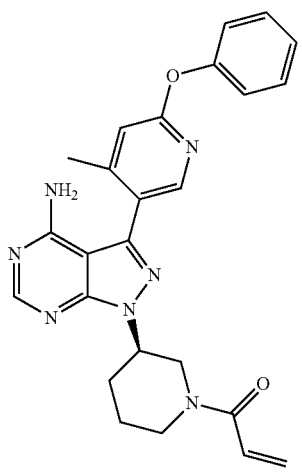
16d
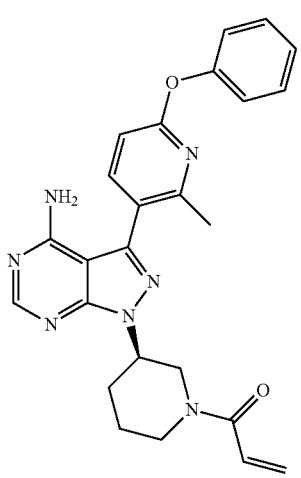
17a
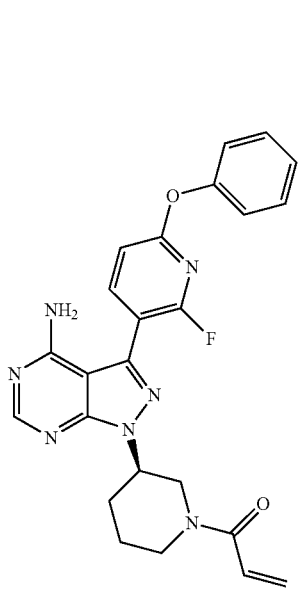

17b
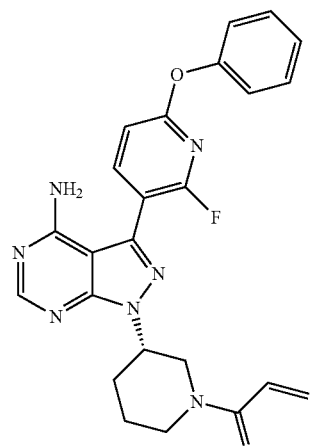
17c
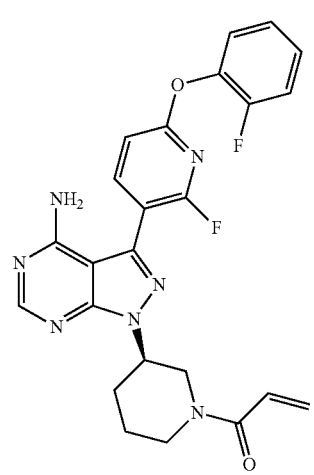
17d
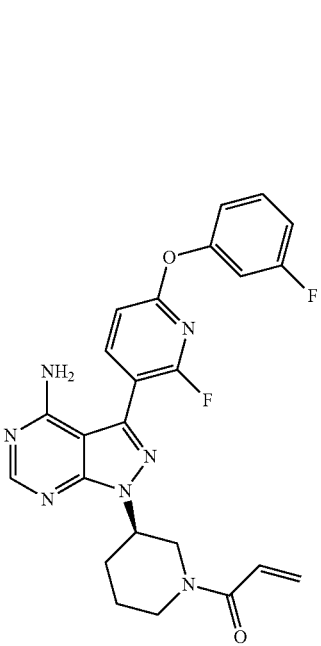
17e
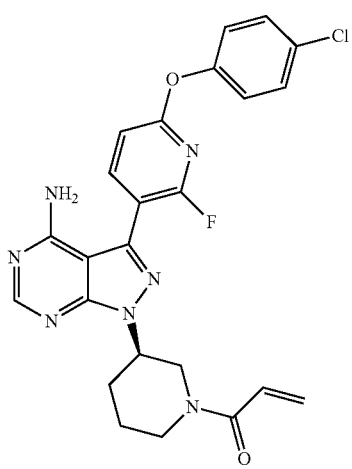
17f
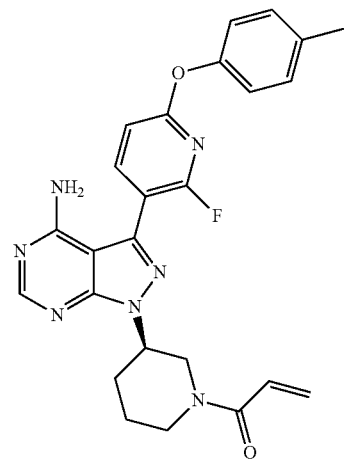
17g
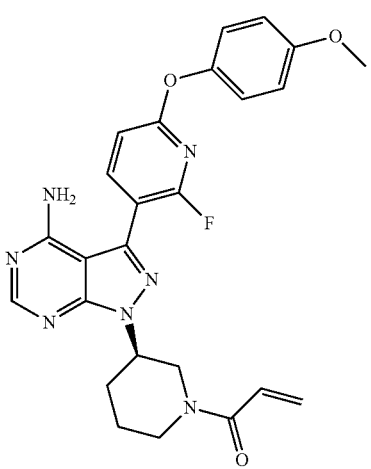

17h
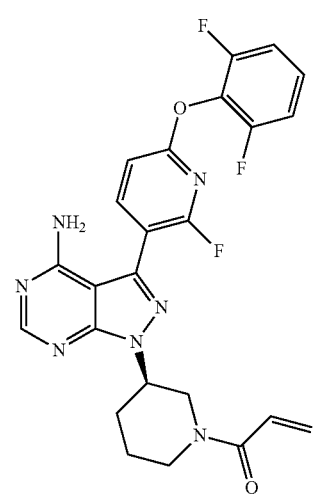
17i
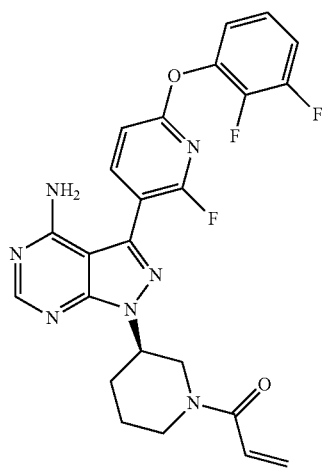
18
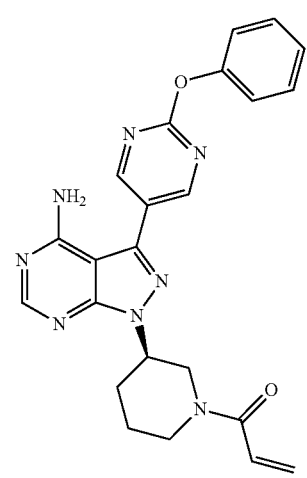
19
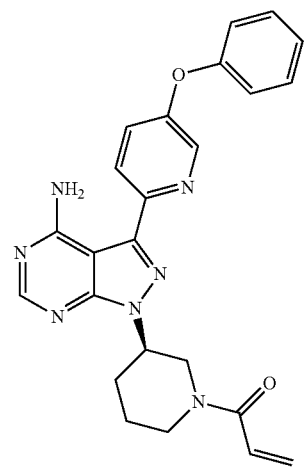
20a
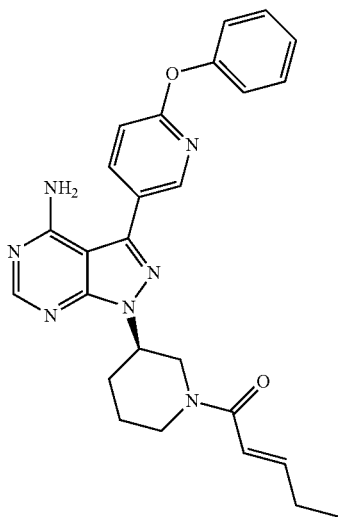
20b
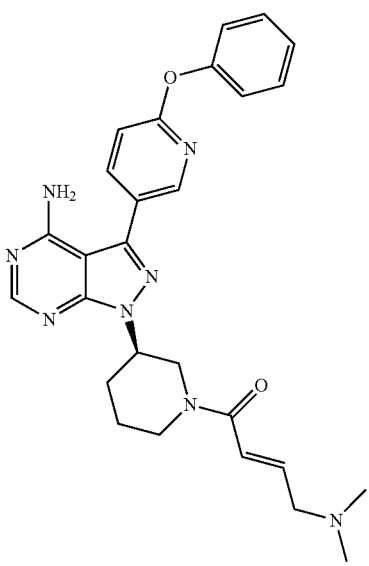

20c
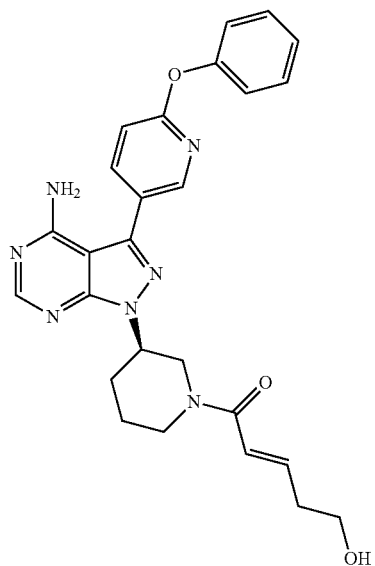
21a
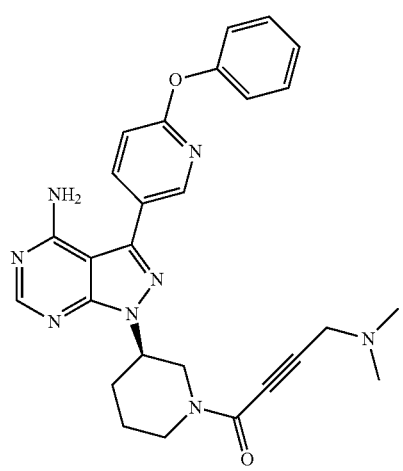
21b
21c
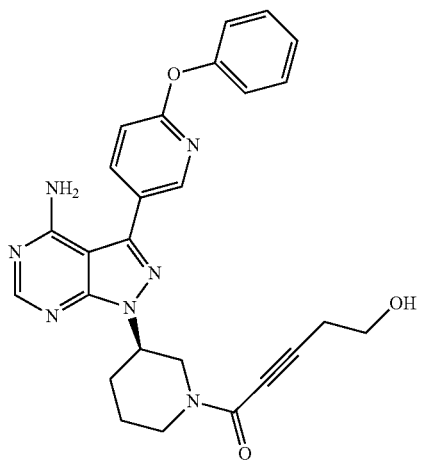
22
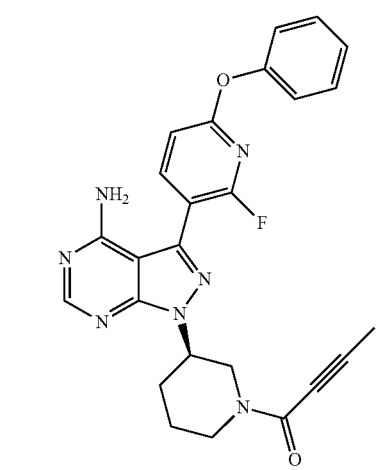
23a
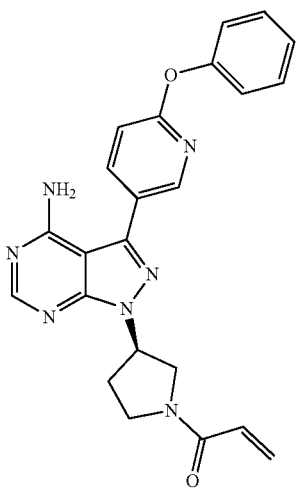

23b
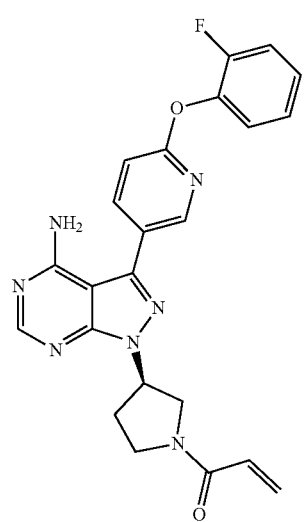
23c
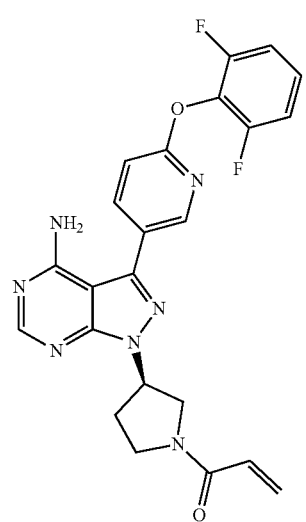
23d
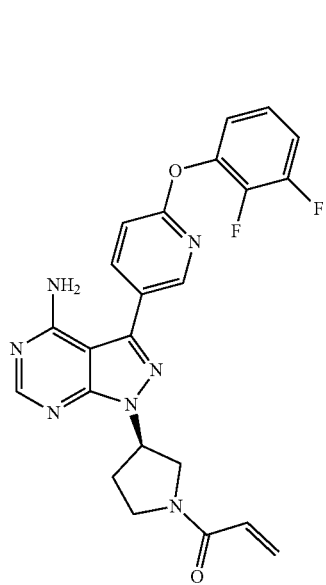
24a
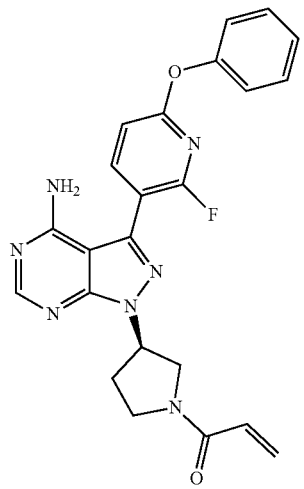
24b
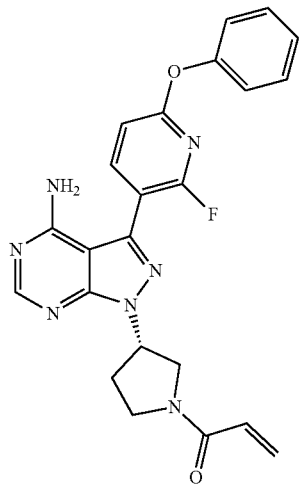
24c
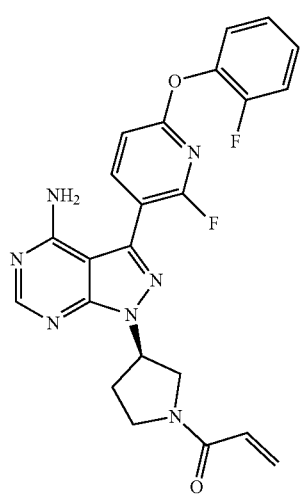

-continued

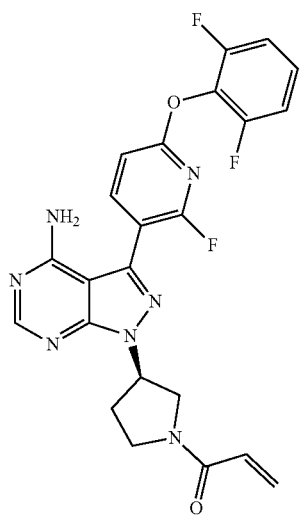
24d

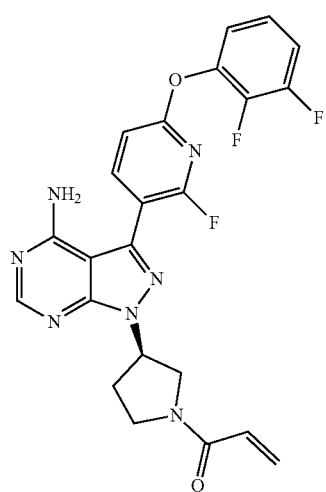
24e

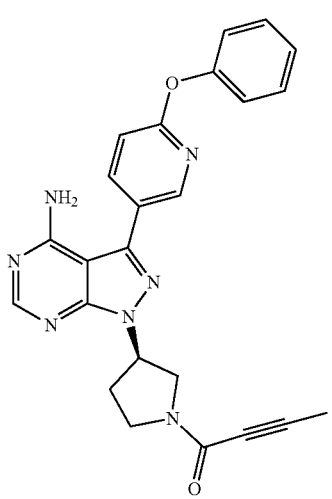
25a

-continued

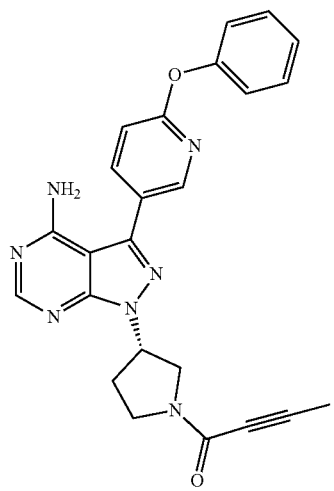
25b and their optical isomers, or pharmaceutically acceptable salts or solvates.

11. A compound of claim 1, wherein the azaalkyl refers to that one or more carbon atoms of C1-C6 alkyl are substituted by nitrogen atoms; the oxaalkyl refers to that one or more carbon atoms of C1-C6 alkyl are substituted by oxygen atoms.

12. A pharmaceutical composition, comprising one or more of the compounds of claim 1.

13. A pharmaceutical preparation, comprising at least one active component, wherein the active component(s) is/are one or more of the compounds of claim 1.

14. A pharmaceutical composition, comprising one or more of the compounds of claim 10.

15. A method of inhibiting Bruton's tyrosine kinase activity, comprising the step of administering a subject the compound of claim 1.

16. A method of treating B-cell proliferation related diseases, selected from the group consisting of diffuse large B cell lymphoma, follicular lymphoma, chronic lymphocytic leukemia, B cell lymphocytic leukemia, Precursor B-cell lymphoblastic leukemia, lymphatic lymphoma/Waldenström macroglobulinemia, splenic marginal lymphoma, plasma cell myeloma, plasmacytoma, extranodal marginal zone B-cell lymphoma, lymph node marginal zone B cell lymphoma, mantle cell lymphoma, mediastinum (thymus) large B-cell lymphoma, intravascular large B-cell lymphoma, primary exudative lymphoma, Burkitt lymphoma/leukemia and lymphomatoid granulomatous disease, comprising the step of administering a subject the compound of claim 1 alone or in combination with other drugs.

17. A method of treating autoimmune diseases, selected from the group consisting of inflammatory bowel disease, arthritis, lupus, rheumatoidarthritis, psoriatic arthritis, osteoarthritis, Still's disease, juvenile arthritis, diabetes, myasthenia gravis, Hashimoto's thyroiditis, Ord's thyroiditis, Graves'disease, Sjögren's syndrome, multiple sclerosis, Guillain-Barré syndrome, acute disseminated encephalomyelitis, Addison's disease, visual ocular palsymyoclonusSyndrome, mandatory spondylitis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal-arteritis, warm autoimmune hemolytic anemia, Wegener's granulomatosis, psoriasis, generalized hairremoval, Behçet's disease, chronic fatigue, familial dysautonomia, endometriosis, interstitial cystitis, neuromuscular rigidity, scleroderma or vulvar pain, and chronic graft-versus-host disease, comprising the step of administering a subject the compound of claim 1 alone or in combination with other drugs.

18. A method of treating rheumatoid arthritis and lupus erythematosus, comprising the step of administering a subject the compound of claim 1 alone or in combination with other drugs.

19. A method of inhibiting Bruton's tyrosine kinase activity, comprising the step of administering a subject the compound of claim 10.

\* \* \* \* \*